United States Patent
Alokaili

(10) Patent No.: US 9,364,208 B2
(45) Date of Patent: Jun. 14, 2016

(54) MEDICAL MATERIAL DELIVERY DEVICE

(71) Applicants: KING ABDULLAH INTERNATIONAL MEDICAL RESEARCH CENTER, Riyadh (SA); KING SAUD BIN ABDULAZIZ UNIVERSITY FOR HEALTH SCIENCES, Riyadh (SA); NATIONAL GUARD HEALTH AFFAIRS

(72) Inventor: Riyadh Nasser Alokaili, Riyadh (SA)

(73) Assignees: KING ABDULLAH INTERNATIONAL MEDICAL RESEARCH CENTER, Riyadh (SA); KING SAUD BIN ABDULAZIZ UNIVERSITY FOR HEALTH SCIENCES, Riyadh (SA); NATIONAL GUARD HEALTH AFFAIRS, Riyadh (SA)

( * ) Notice: Subject to any disclaimer, the term of this patent is extended or adjusted under 35 U.S.C. 154(b) by 0 days.

(21) Appl. No.: 14/218,344

(22) Filed: Mar. 18, 2014

(65) Prior Publication Data
US 2015/0265261 A1    Sep. 24, 2015

(51) Int. Cl.
*A61B 17/00* (2006.01)
*A61B 17/12* (2006.01)
(Continued)

(52) U.S. Cl.
CPC ....... *A61B 17/0057* (2013.01); *A61B 17/12031* (2013.01); *A61B 17/12113* (2013.01); *A61B 17/7061* (2013.01); *A61B 17/8811* (2013.01); *A61B 2017/0065* (2013.01); *A61B 2017/00557* (2013.01); *A61B 2017/00641* (2013.01);
(Continued)

(58) Field of Classification Search
CPC ............ A61B 2017/0065; A61B 2017/00575; A61B 2017/00654; A61B 2017/00676; A61B 2017/00637; A61B 2018/0025; A61B 2018/0063; A61M 2025/1052; A61M 2025/1054; A61M 2025/105; A61M 2025/107
See application file for complete search history.

(56) References Cited

U.S. PATENT DOCUMENTS 4,755,170 A * 7/1988 Golden ......................... 604/513
5,391,183 A    2/1995 Janzen et al.
(Continued)

OTHER PUBLICATIONS

Break—Definition from the Free Merriam-Webster online Dictionary (Feb. 19, 2010, accessed Jul. 9, 2015).*
(Continued)

*Primary Examiner* — Bhisma Mehta
*Assistant Examiner* — James D Ponton
(74) *Attorney, Agent, or Firm* — Richard C. Litman

(57) ABSTRACT

A medical material delivery device includes a shaft having a lumen that receives a therapeutic agent, and can include a guide having a channel for receiving a medical instrument adapted for positioning in conjunction with a bodily part. An expandable member positioned in conjunction with the guide is adapted for communication with the bodily part and is arranged to burst open when the expandable member is disrupted by a disrupting mechanism to deliver the therapeutic agent to the bodily part. Further embodiments include a medical instrument and an expandable member in conjunction with the medical instrument to burst or leak to deliver a therapeutic agent. The medical material delivery device can include a bodily fluid locator attached with the device, as well as can include a second expandable member to inflate and deflate to localize a bodily part, with a first expandable member bursting to deliver a therapeutic agent.

7 Claims, 54 Drawing Sheets

(51) Int. Cl.
*A61B 17/70* (2006.01)
*A61B 17/88* (2006.01)
*A61M 25/10* (2013.01)
*A61M 37/00* (2006.01)

(52) U.S. Cl.
CPC ............ *A61B2017/00654* (2013.01); *A61B 2017/00672* (2013.01); *A61M 25/10* (2013.01); *A61M 37/00* (2013.01); *A61M 2202/0007* (2013.01); *A61M 2202/0427* (2013.01); *A61M 2202/07* (2013.01)

(56) References Cited

U.S. PATENT DOCUMENTS

| | | | |
|---|---|---|---|
| 5,431,639 A * | 7/1995 | Shaw | 604/264 |
| 5,437,292 A | 8/1995 | Kipshidze et al. | |
| 5,443,481 A | 8/1995 | Lee | |
| 5,486,195 A | 1/1996 | Myers et al. | |
| 5,591,205 A | 1/1997 | Fowler | |
| 5,620,461 A | 4/1997 | Muijs Van De Moer et al. | |
| 5,653,730 A | 8/1997 | Hammerslag | |
| 5,665,106 A | 9/1997 | Hammerslag | |
| 5,716,375 A | 2/1998 | Fowler | |
| 5,725,498 A | 3/1998 | Janzen et al. | |
| 5,728,134 A | 3/1998 | Barak | |
| 5,746,755 A | 5/1998 | Wood et al. | |
| 5,792,173 A | 8/1998 | Breen et al. | |
| 5,795,331 A | 8/1998 | Cragg et al. | |
| 6,071,300 A | 6/2000 | Brenneman et al. | |
| 7,488,340 B2 | 2/2009 | Kauphusman et al. | |
| 8,333,787 B2 | 12/2012 | Pipenhagen et al. | |
| 8,382,794 B2 | 2/2013 | Belhe et al. | |
| 2003/0130620 A1 | 7/2003 | Alokaili | |
| 2007/0112306 A1 * | 5/2007 | Agnew | 604/164.13 |
| 2008/0027411 A1 * | 1/2008 | Von Oepen | A61M 25/0029 604/508 |
| 2008/0086109 A1 * | 4/2008 | Shabty et al. | 604/508 |
| 2009/0005757 A1 * | 1/2009 | Taber | A61M 25/0082 604/523 |
| 2010/0168767 A1 * | 7/2010 | Yassinzadeh et al. | 606/139 |
| 2010/0249749 A1 * | 9/2010 | Cheng | A61L 29/085 604/509 |
| 2011/0166595 A1 | 7/2011 | Vidlund et al. | |
| 2012/0109276 A1 * | 5/2012 | Diener | A61M 25/1027 623/1.11 |
| 2013/0281787 A1 * | 10/2013 | Avneri | A61M 25/0133 600/208 |

OTHER PUBLICATIONS

Burst—Definition from the Free Merriam-Webster online Dictionary (Jun. 3, 2006, accessed Jul. 9, 2015).*

Gulmez, I., O. Ekmekcioglu, and M. Karacagil. "A Comparison of Various Methods to Burst Foley Catheter Balloons and the Risk of Free-fragment Formation." BJU International BJU Int 77.5 (1996): 716-18. Web.*

* cited by examiner

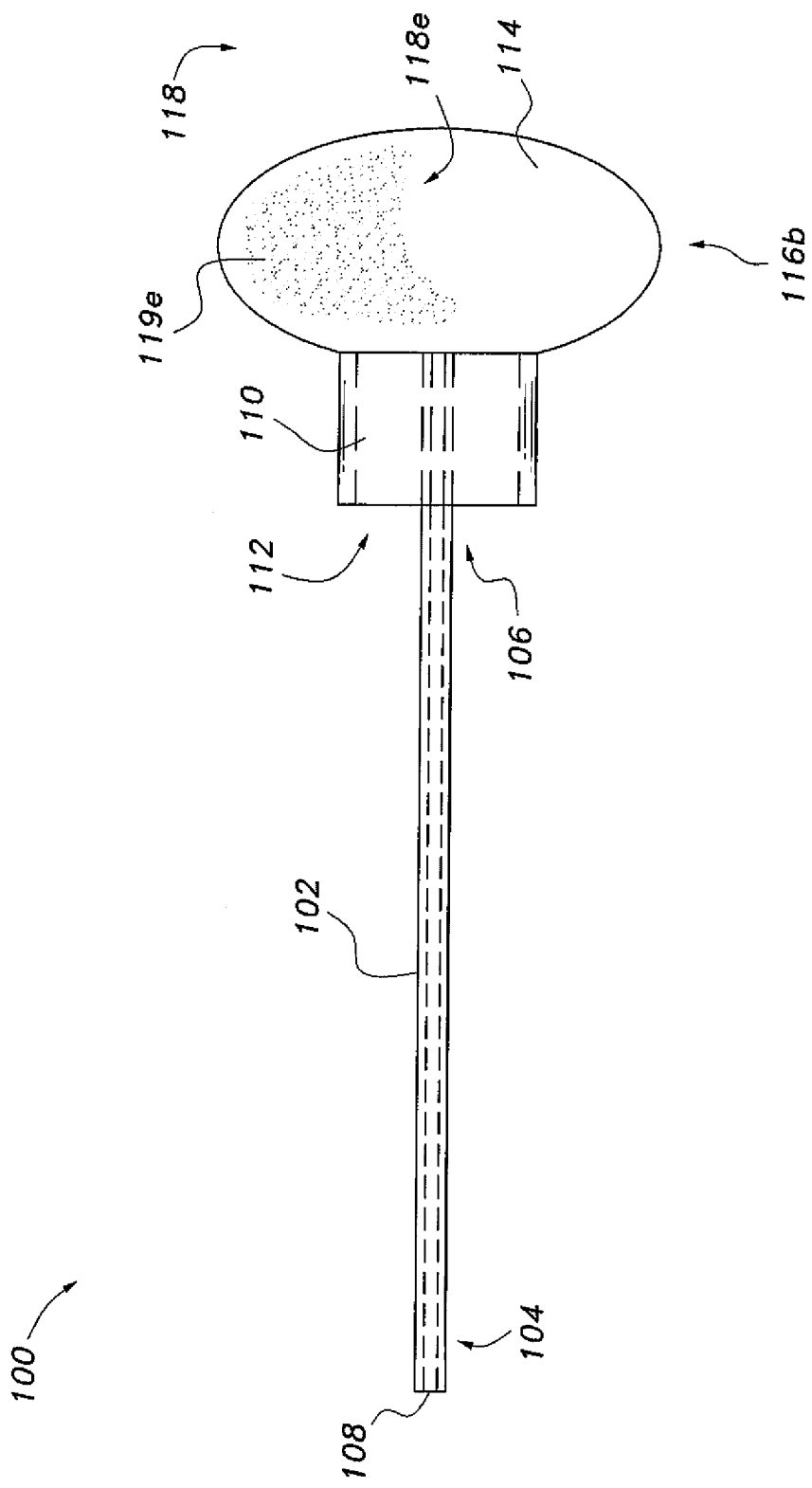

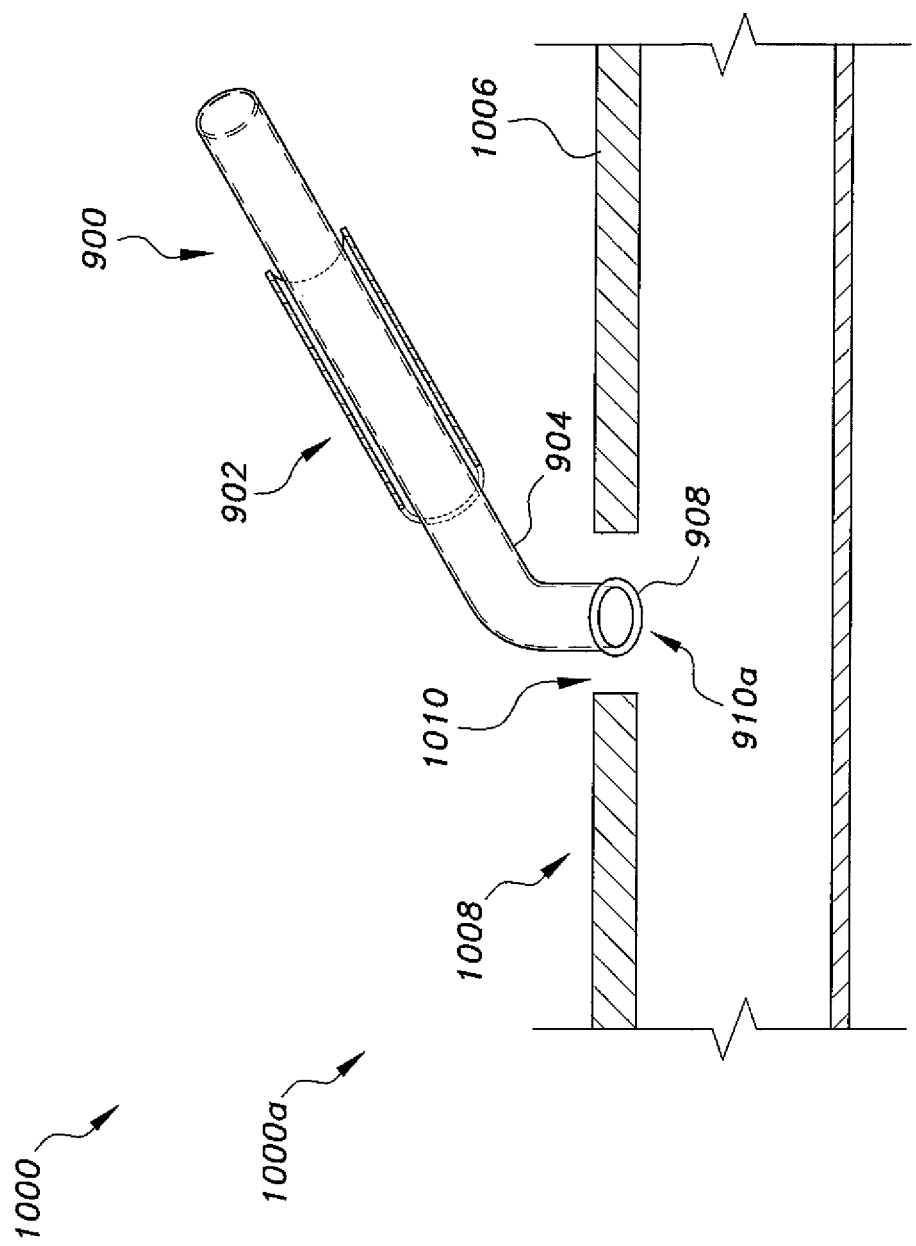

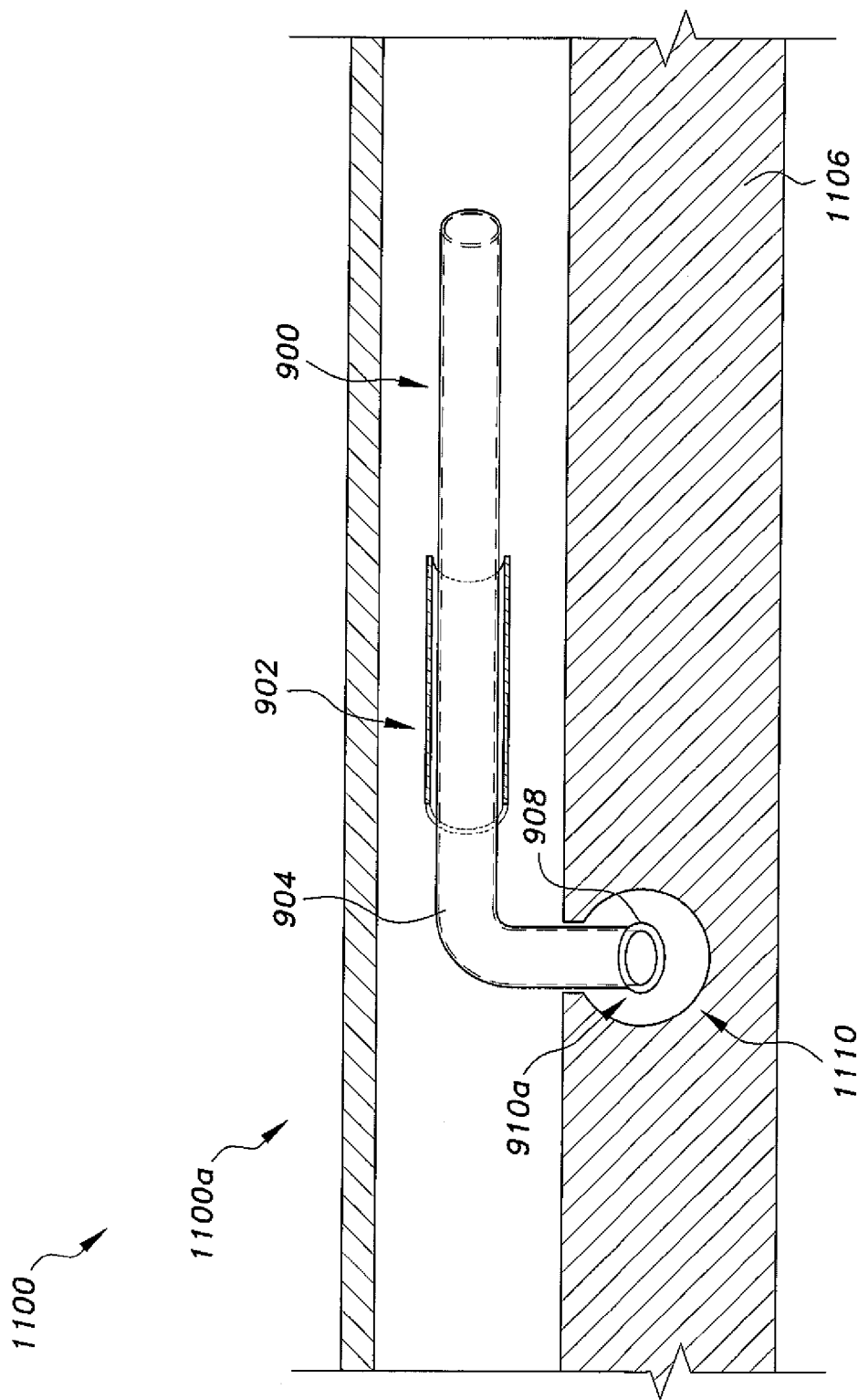

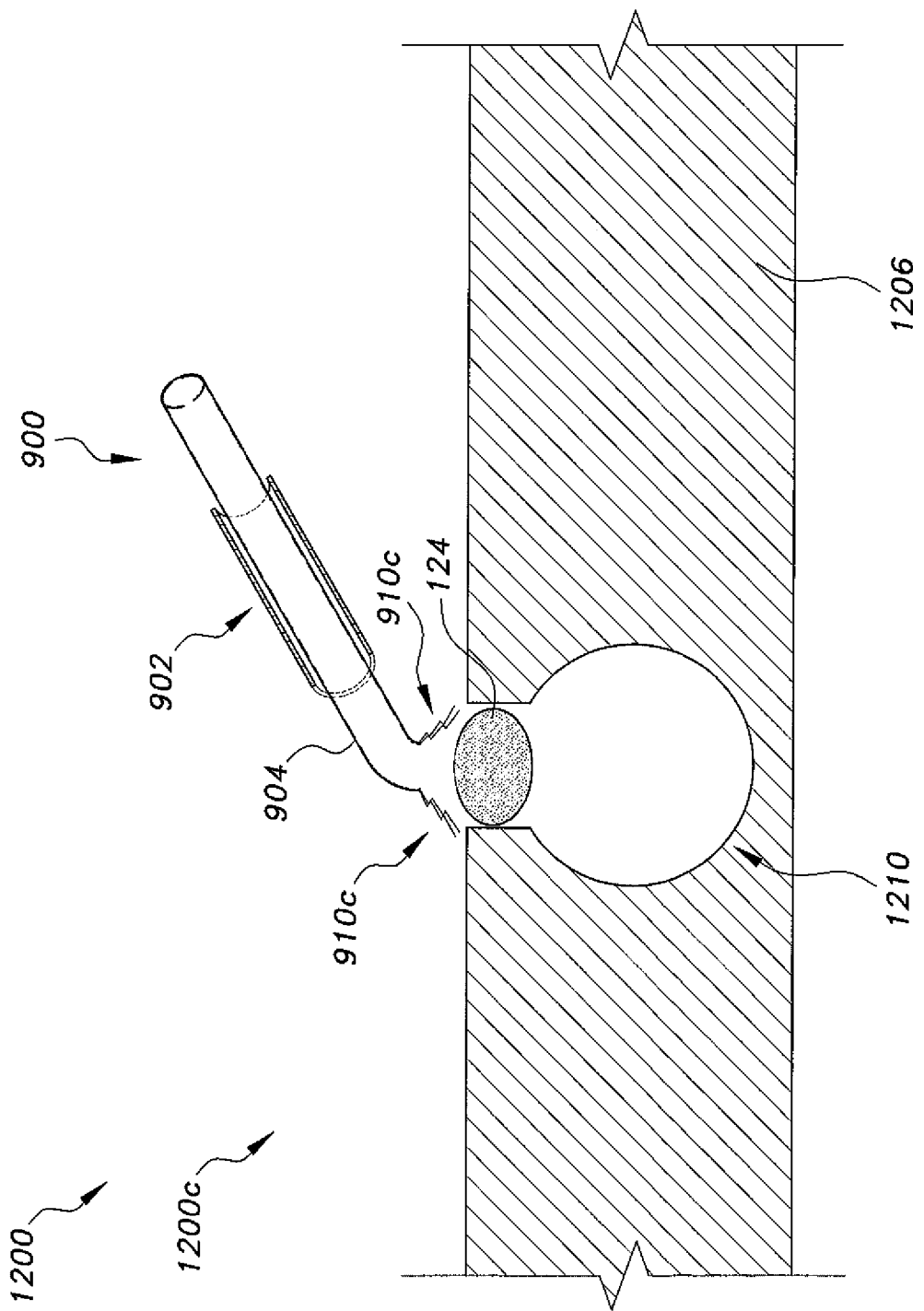

MEDICAL MATERIAL DELIVERY DEVICE

BACKGROUND OF THE INVENTION

1. Field of the Invention

The present invention relates to surgical instruments, and particularly to a medical material delivery device.

2. Description of the Related Art

Medical material can be delivered to subjects in numerous ways, such as application on the surfaces of a subject's skin, oral ingestion, or administration to the subject through a needle or catheter, for example. These numerous methods can have advantages and disadvantages; therefore medical practice continues to seek new methods of material delivery to compliment the numerous other methods of material delivery.

In one particular area of medical practice, procedures involving the insertion of medical instruments into blood vessels or tissues or other bodily parts are common procedures in the medical field today. Even though they are common, closing of the openings caused by these procedures can be problematic. A current approach for sealing a puncture caused by a medical procedure as, for example, a procedure involving the puncturing of a blood vessel to perform an angiographic procedure, is to seal the puncture by using manual pressure. In this approach, manual pressure is applied directly to the skin above the access puncture for a time period until the natural clotting process of the body seals the puncture. A drawback of this approach is that it can be uncomfortable for the patient while the pressure is applied and it can be time consuming, including taking up the time of the medical staff assisting the patient.

Another approach to seal a puncture employs the use of absorbable intra-vessel anchors in conjunction with extra-vessel collagen sponges. Under this approach, the anchor and collagen sponge are held together by a self-tightening suture loop and slip knot, which, when tightened, sandwiches the puncture hole between the anchor and the collagen sponge. Although these devices can be effective in sealing punctures, in certain situations, for example punctures in the femoral artery, these devices may not work successfully. Other factors as can prohibit using these devices include the presence of peripheral vascular disease, a poor needle stick location by either having too high of a puncture or too low of a puncture, or relatively smaller blood vessel sizes which can interfere with anchor placement and prevent proper seating of the anchor against the blood vessel wall.

In an effort to overcome some of these problems, another device for sealing a puncture is a plug that is deposited outside the blood vessel at the puncture site with no component inside the blood vessel. This approach generally requires a consistent placement of the plug near the blood vessel wall. This consistent placement can be problematic, for example, when trying to seal a punctured artery pressure exerted on the plug as the blood pressure generated by the beating heart can cause the plug to move away from the puncture site in the arterial wall. This can result in a hematoma or other complications at the puncture site. Further, the plug may not seal the puncture site sufficiently enough to prevent leakage from the blood vessel.

Therefore, it is desirable for a device that can deliver a medical material for medical procedures to be able to do so in an easy, quick, less painful and secure manner.

Thus, a medical material delivery device addressing the aforementioned problems, that can include a method of delivery complimenting other methods of delivery, is desired.

SUMMARY OF THE INVENTION

Embodiments of a medical material delivery device are provided. An embodiment of the medical material delivery device includes a shaft having a proximal end and a distal end and also, a lumen that receives a therapeutic agent. A guide positioned at the distal end of the shaft is adapted for positioning in conjunction with a blood vessel or other bodily part. The guide further includes a channel that can receive a medical instrument. An expandable member is positioned in conjunction with the guide and communicates with the lumen of the shaft for expansion by the therapeutic agent. The expandable member is adapted for communication with the blood vessel or other bodily part and is arranged to at least one of burst, leak or become broken when the expandable member is disrupted by a disrupting mechanism to deliver the therapeutic agent to the blood vessel or other bodily part.

In embodiments of a medical material delivery device, the disrupting mechanism can include, for example, at least one of or one or more of one or more longitudinal breakage lines included in the expandable member, at least one generally circumferential breakage line included in the expandable member, a string attached to the expandable member, a needle positioned in communication with the expandable member and a chemical disrupting mechanism. Also, in embodiments of a medical material delivery device, the chemical disrupting mechanism can also include a solvent, such as a chemical solvent, to react with the expandable member, for example.

A further embodiment of the medical material delivery device includes an outer shaft, the outer shaft having a first lumen, the outer shaft adapted for positioning in conjunction with a bodily part. The medical material delivery device also includes a first expandable member, the first expandable member positioned to an exterior of the outer shaft for expansion by a therapeutic agent, the first expandable member adapted for communication with a bodily part, the first expandable member arranged to at least one of burst, leak or become broken when disrupted by a disrupting mechanism to deliver a therapeutic agent to an exterior area of the bodily part in communication with the first expandable member.

The medical material delivery device further includes a first delivery member, the first delivery member positioned in association with the outer shaft in communication with the first expandable member to deliver the therapeutic agent to the first expandable member. Also, the medical material delivery device includes an inner shaft, the inner shaft positioned within the first lumen of the outer shaft, the inner shaft having a second lumen adapted to receive a medical instrument, the inner shaft adapted for insertion within the bodily part.

Additionally, the medical material delivery device includes a second expandable member, the second expandable member positioned to an exterior of the inner shaft for expansion, the second expandable member adapted for communication with an interior of the bodily part, the second expandable member arranged to selectively inflate and deflate, and includes a second delivery member, the second delivery member positioned in association with the inner shaft in communication with the second expandable member to assist the second expandable member to one or more of inflate or deflate. For example, the second expandable member can be arranged to contact the inner vascular wall to prevent further withdrawal of the medical material delivery device and localize an arteriotomy.

Another embodiment of the medical material delivery device includes a medical instrument, the medical instrument including a lumen adapted for receiving a therapeutic agent, the medical instrument adapted for communication with a blood vessel or other bodily part, and also includes an expandable member, the expandable member positioned in conjunction with the medical instrument for expansion by the therapeutic agent when delivered in conjunction with the medical instrument, the expandable member adapted for communication with the blood vessel or other bodily part, the expandable member arranged to at least one of burst, leak or become broken when disrupted by a disrupting mechanism to deliver the therapeutic agent to an area of the blood vessel or other bodily part in communication with the expandable member. The medical instrument can include, for example, a trocar, a needle, a cannula, and a guide wire, a sheath, a scalpel or a catheter. Also, the medical material delivery device can include a bodily fluid locator, such as a vascular locator, to indicate communication of the medical material delivery device with the blood vessel or other bodily part by a presence of blood or other bodily fluid within the bodily fluid locator.

These and other features of the present invention, such as those including but not limited to medical applications, will become readily apparent upon further review of the following specification and drawings.

BRIEF DESCRIPTION OF THE DRAWINGS

FIG. 2E is a top view of an embodiment of a disrupting mechanism having a chemical solvent susceptible part of the expandable member of embodiments of a medical material delivery device having a generally ring shape guide according to the present invention.

FIG. 10A is an environmental view of an embodiment of a first step of a method for correcting a fistula in a blood vessel using the embodiments of the medical material delivery device of FIGS. 9A-9B according to the present invention.

FIG. 11A is an environmental cross section view of an embodiment of a first step of a method for correcting an aneurysm using the embodiments of the medical material delivery device of FIGS. 9A-9B according to the present invention.

FIG. 12C is an environmental cross section view of an embodiment of a third step of a method for correcting a hernia using the embodiments of the medical material delivery device of FIGS. 9A-9B according to the present invention.

Unless otherwise indicated, similar reference characters denote corresponding features consistently throughout the attached drawings.

DETAILED DESCRIPTION OF THE PREFERRED EMBODIMENTS

Figure 1A:
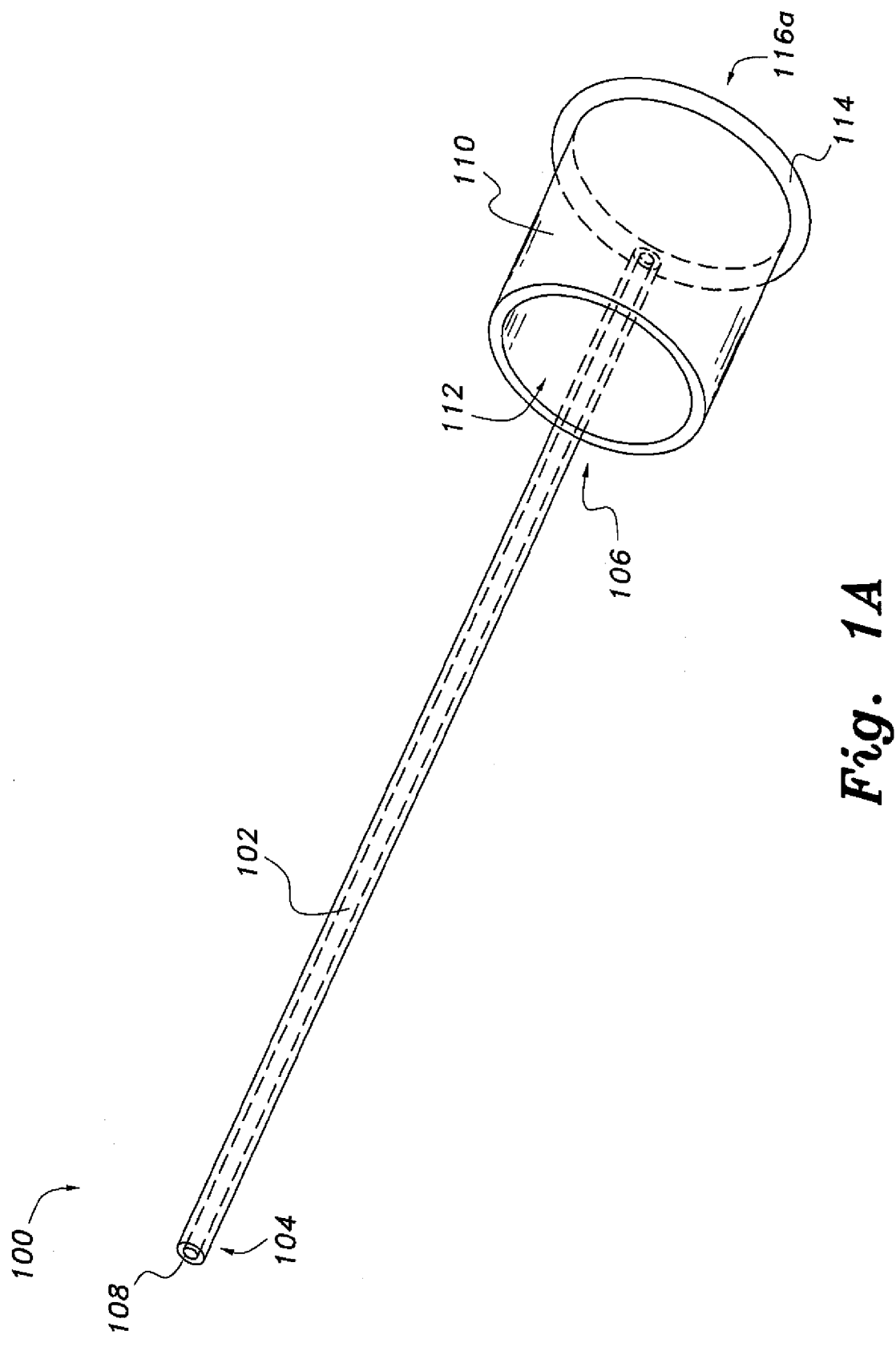
FIG. 1A is a perspective view of an embodiment of a medical material delivery device having a generally ring shape guide according to the present invention.

Referring to FIGS. 1A-2E, a medical material delivery device 100 is shown. The medical material delivery device 100 includes a shaft 102 that has a proximal end 104 that is situated towards a user and a distal end 106 that is at the other end of the shaft 102 away from the proximal end 104 and is situated towards a patient that is having or has had a medical procedure performed. The user, generally a health care practitioner, can control the medical material delivery device 100 by gripping directly the shaft 102 or, depending on the user's needs, the user can grasp a handle or similar structure that is secured to the proximal end 104 that can allow for the advancement and positioning of the medical material delivery device 100.

The shaft 102 of the medical material delivery device 100 also includes a lumen 108 within the interior of the shaft 102 that traverses the length of the shaft. The lumen 108 is an open ended pathway with one open end of the lumen 108 at the proximal end 104 of the shaft 102 and the other open end of the lumen 108 is at the distal end 106 of the shaft 102. This other open end of the lumen 108 that is located at the distal end 106 will insert and empty into an expandable member 114. The expandable member 114 is positioned in conjunction with a guide 110 and expands by manual filling when the user places a therapeutic agent 124, shown in FIGS. 7E-7F, into the open end of the lumen 108 located at the proximal end 104 of the shaft 102.

The type of therapeutic agent that is placed within the lumen 108 of the shaft 102 that fills the expandable member 114 typically depends on the particular needs and the medical procedure performed on a bodily part. Examples of bodily parts to which embodiments of a medical material delivery device, as described herein, can include vascular and non-vascular bodily parts, such as blood vessels, trachea, bronchial tree, vascular tree, elementary tract, biliary tree, bones or other bodily compartments, spaces or cavities and, therefore, such bodily parts should not be construed in a limiting sense.

For example, if an angiographic procedure is performed, the medical procedure would typically involve the use of a medical instrument to puncture a blood vessel, such as an artery. Therefore, based on this procedure and a need to close the blood vessel, the user could select a therapeutic agent 124, such as the patient's own clotted blood, thrombin, fibrin, a liquid embolic material, a lipid based sealing material, or any other common coagulation and embolization material. Other possible choices for a therapeutic agent 124 can include drugs that provide local or systemic therapeutic effects in the body, a phase changeable material, such as acrylic bone cement for procedures involving a vertebroplasty or kyphoplasty, collagen, coils, or any other common implantable medical material, such as to deposit a relatively small collagen plug, suture or coil adjacent to a puncture site.

Figure 7A:
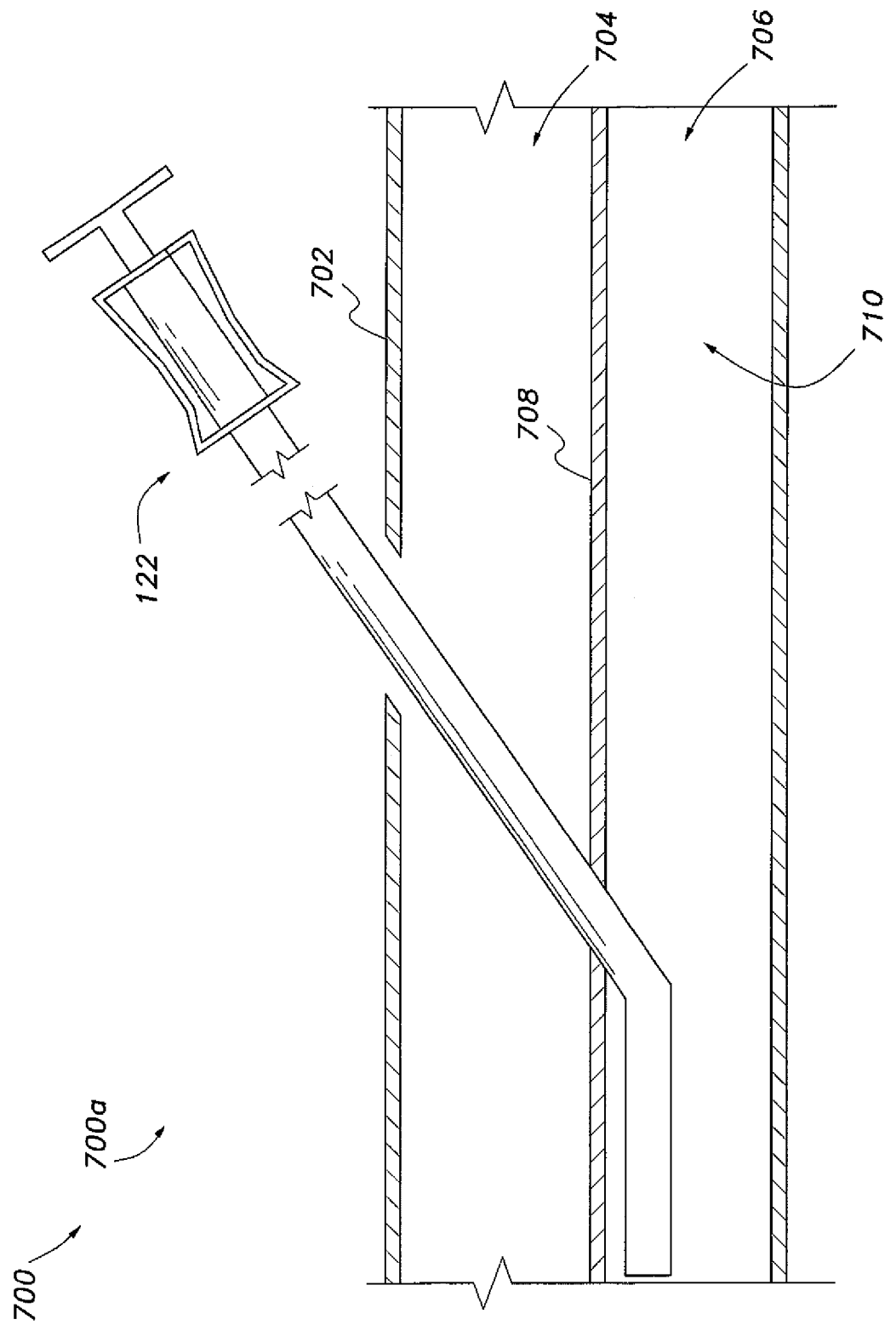
FIG. 7A is an environmental cross section of an embodiment of a first step of a method for sealing a puncture in a blood vessel using embodiments of a medical material delivery device according to the present invention.
Figure 7B:
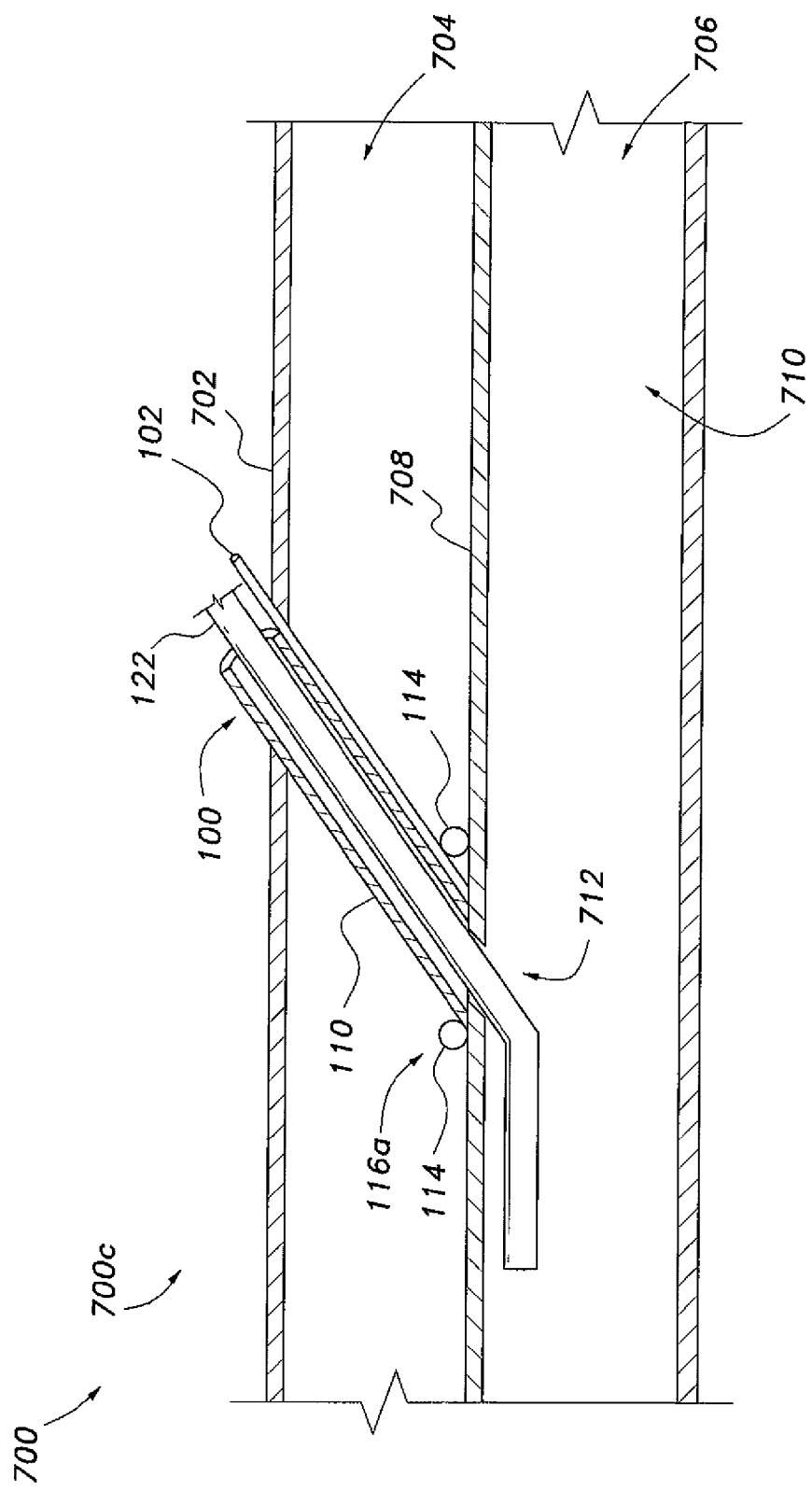
FIG. 7B is an environmental cross section of an embodiment of a second step of a method for sealing a puncture in a blood vessel using embodiments of a medical material delivery device according to the present invention.

The guide 110 of the medical material delivery device 100 is positioned at the distal end 106 of the shaft 102 and is adapted for positioning in conjunction with a blood vessel, as an example of a bodily part, as shown in FIGS. 7A-7F. The guide 110 can also be adapted for positioning in conjunction with other bodily parts, such as vertebrae, depending on the particular needs or medical procedure to be performed. As shown in FIGS. 1A-2E, the guide 110 is configured in a generally ring shape and includes a channel 112 that is configured to receive a medical instrument 122 as shown in FIGS. 7A and 7B.

The channel 112 allows for the guide 110 to be placed in conjunction with the medical instrument 122, thereby allowing ease of use of the medical material delivery device 100 along with the medical instrument 122 during a medical procedure. The diameter of the channel 112 of the guide 110 can vary depending on the diameter of the medical instrument 122 that is being used in the medical procedure. For example, if the medical instrument 122 is a needle, then the diameter of the generally ring shape guide 110 will be less than if the medical instrument 122 was a scope. Other examples of a medical instrument 122 that can be used with medical material delivery device 100 include a trocar, a cannula, a guide wire, a scalpel, sheath, catheter or any other common medical instrument that is used for invasive medical procedures.

The expandable member 114 that is positioned in conjunction with the guide 110 is adapted for communication with a bodily part, such as a blood vessel, while the expandable member 114 is outside of the lumen 108 of the shaft 102. The expandable member 114 can be made from a suitable material, such as an elastic medical grade material, a plastic material or a textile material, for example, that can be deflated, inflated/expanded and, when appropriate, disrupted, such as by being burst, that can allow for the expansion of the expandable member 114, or can be made from other suitable material, such as depending upon the use or application, for example. By using an elastic material, as an example, the expandable member 114 can placed into at least three arrangements.

Figure 1B:
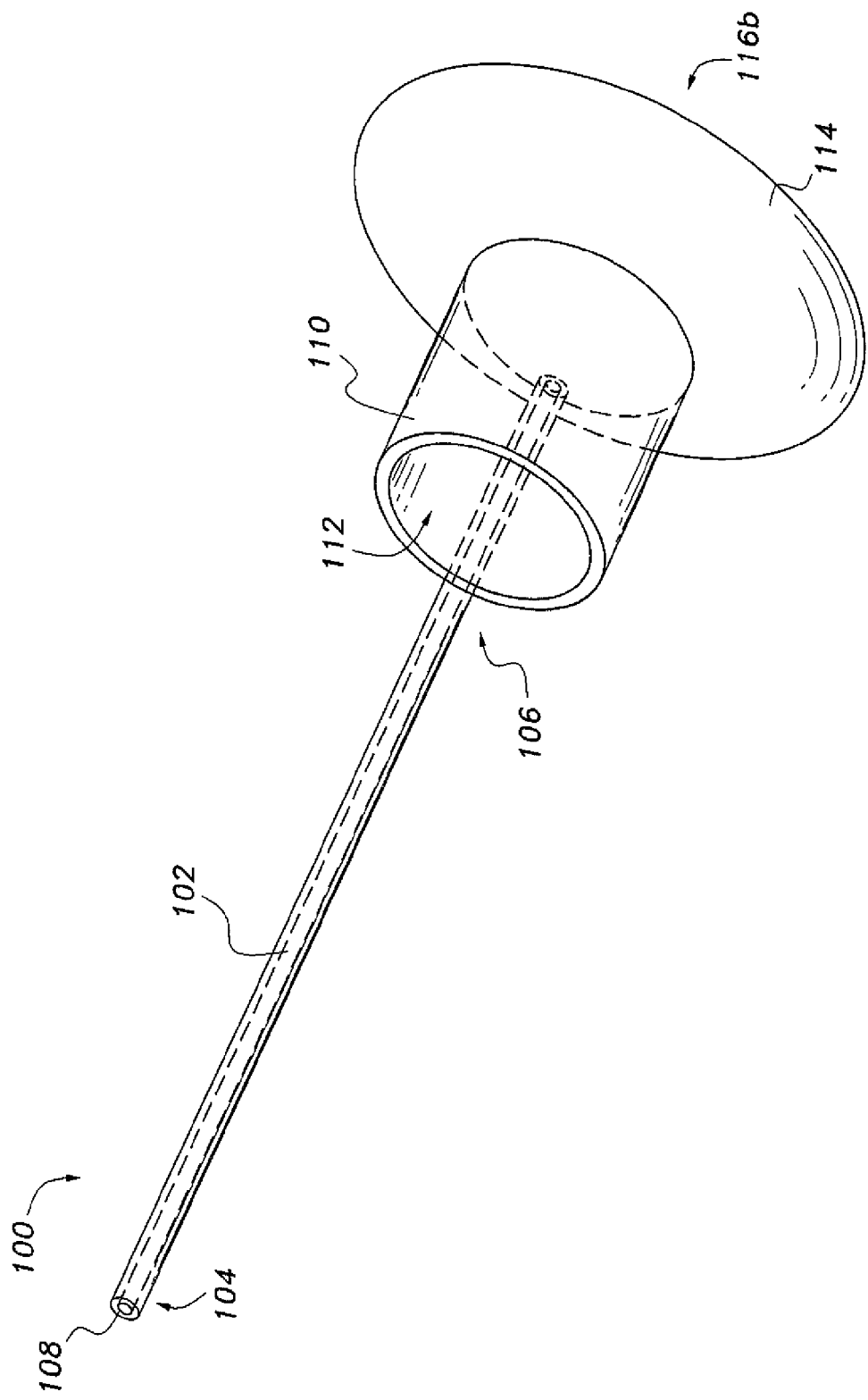
FIG. 1B is a perspective view of an embodiment of an inflated expandable member of embodiments of a medical material delivery device having a generally ring shape guide according to the present invention.

An unexpanded arrangement 116a is shown in FIG. 1A, where the therapeutic agent 124 has yet to be placed within the expandable member 114. The expandable member 114 can also be placed into an expanded arrangement 116b, as shown in FIG. 1B, where the expandable member 114 is filled with the therapeutic agent 124, or can be placed in other arrangements where the expandable member 114 is in one or more partially filled states, for example.

Figure 7C:
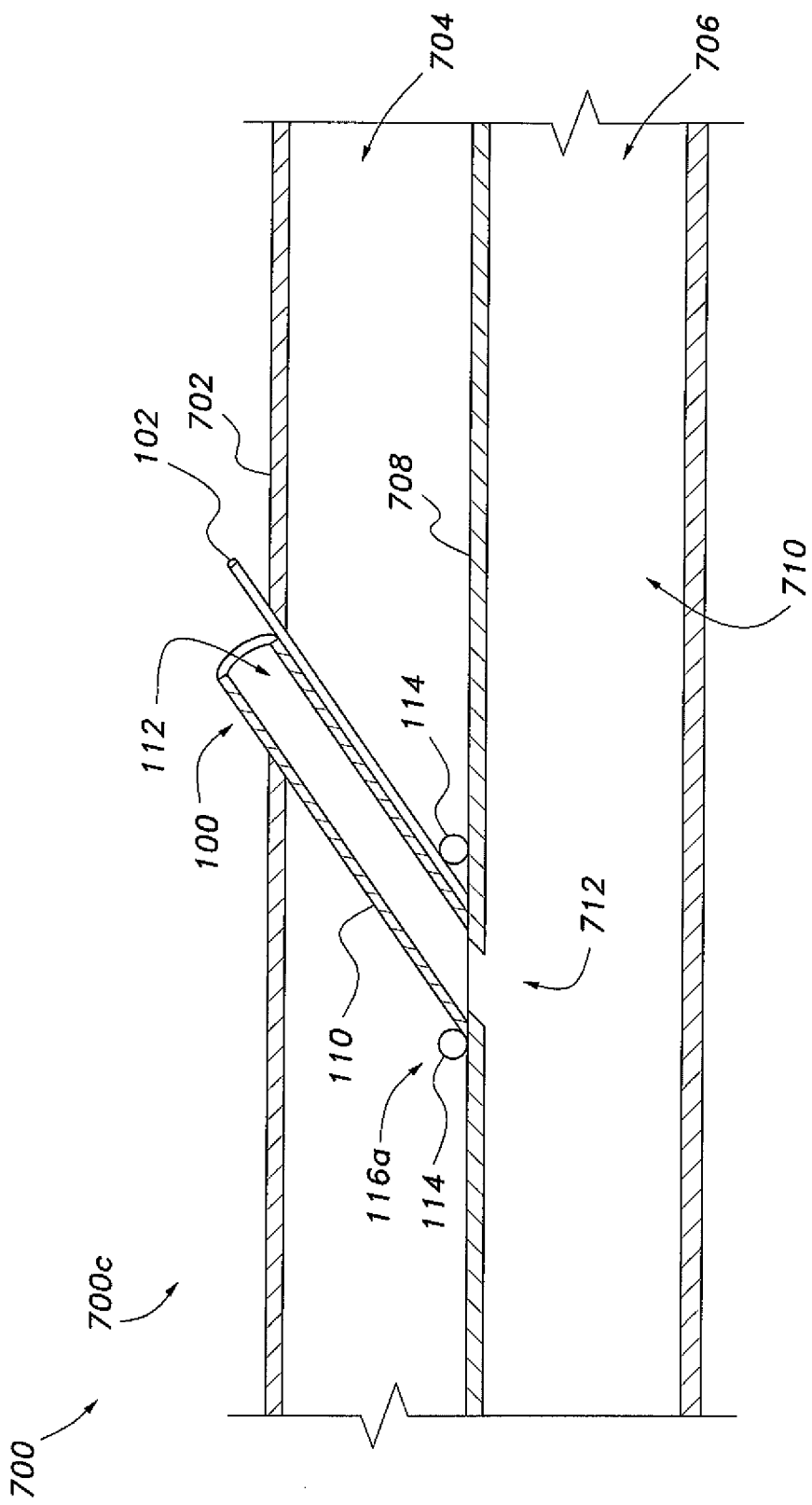
FIG. 7C is an environmental cross section of an embodiment of a third step of a method for sealing a puncture in a blood vessel using embodiments of a medical material delivery device according to the present invention.
Figure 7D:
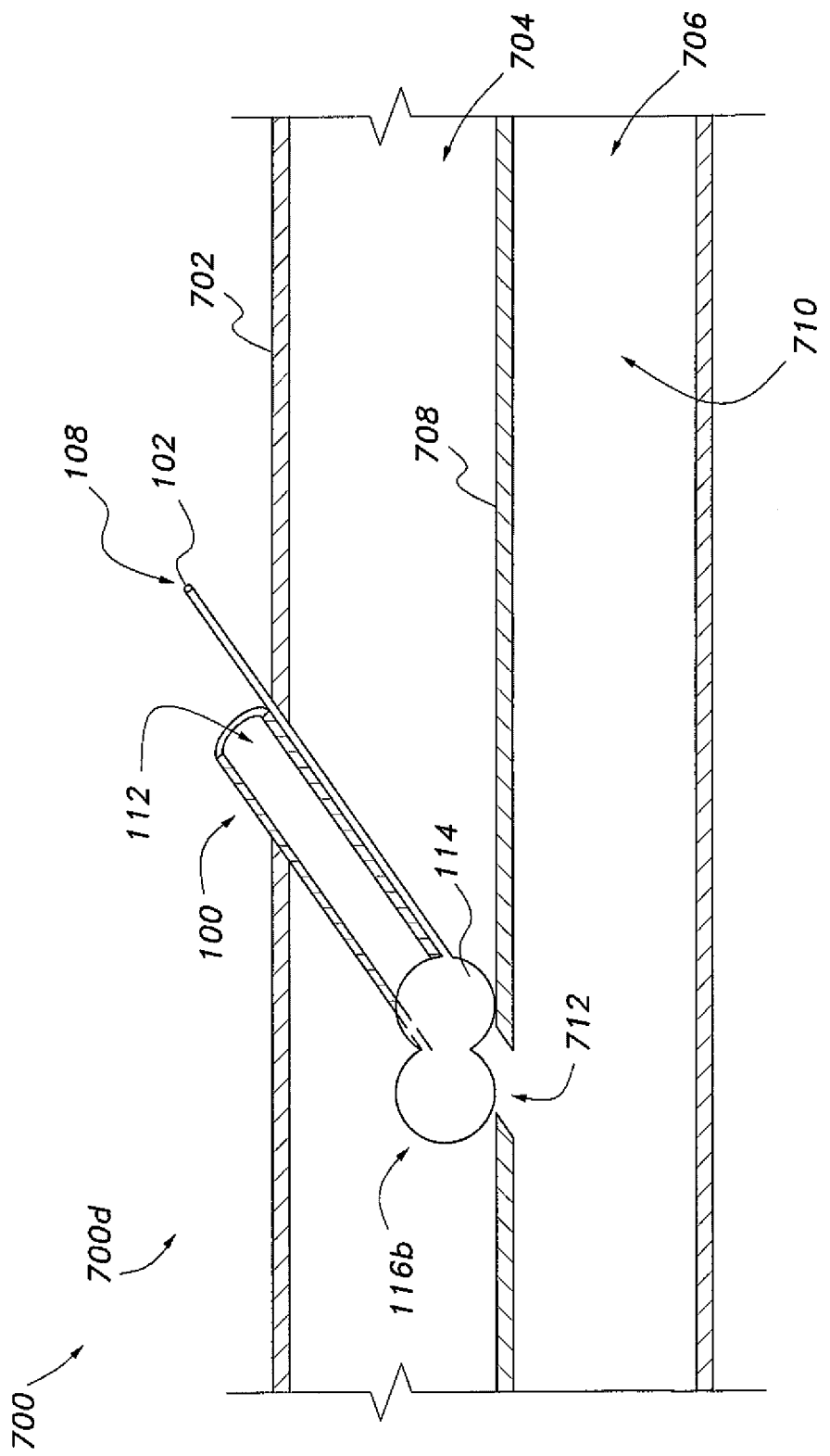
FIG. 7D is an environmental cross section of an embodiment of a fourth step of a method for sealing a puncture in a blood vessel using embodiments of a medical material delivery device according to the present invention.
Figure 7E:
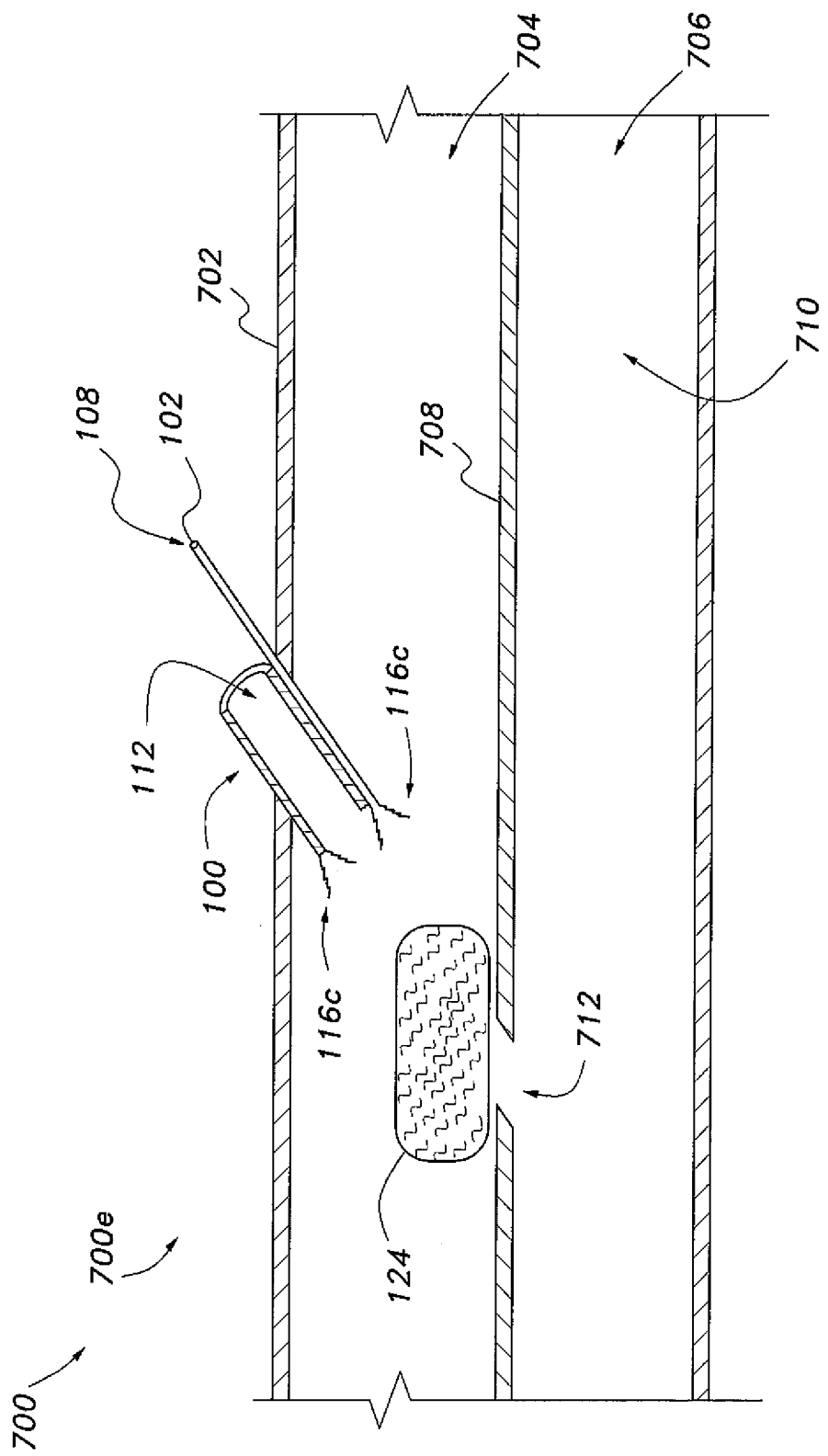
FIG. 7E is an environmental cross section of an embodiment of a fifth step of a method for sealing a puncture in a blood vessel using embodiments of a medical material delivery device according to the present invention.

The third arrangement of the expandable member 114 is a burst open arrangement 116c, as shown in FIG. 7E, where the expandable member 114 is disrupted by a disrupting mechanism 118. The disrupting mechanism 118 causes the expandable member 114 to at least one of burst, leak or become broken, depending on the use or application, for example, to deliver the therapeutic agent 124. Various embodiments of the disrupting mechanism 118 are provided in FIGS. 2A-2E. When the expandable member 114 is in the burst open arrangement 116c, the therapeutic agent 124 contained within the expandable member 114 is delivered to the targeted bodily part, such as a blood vessel wall, that is in communication with the expandable member 114.

Figure 2A:
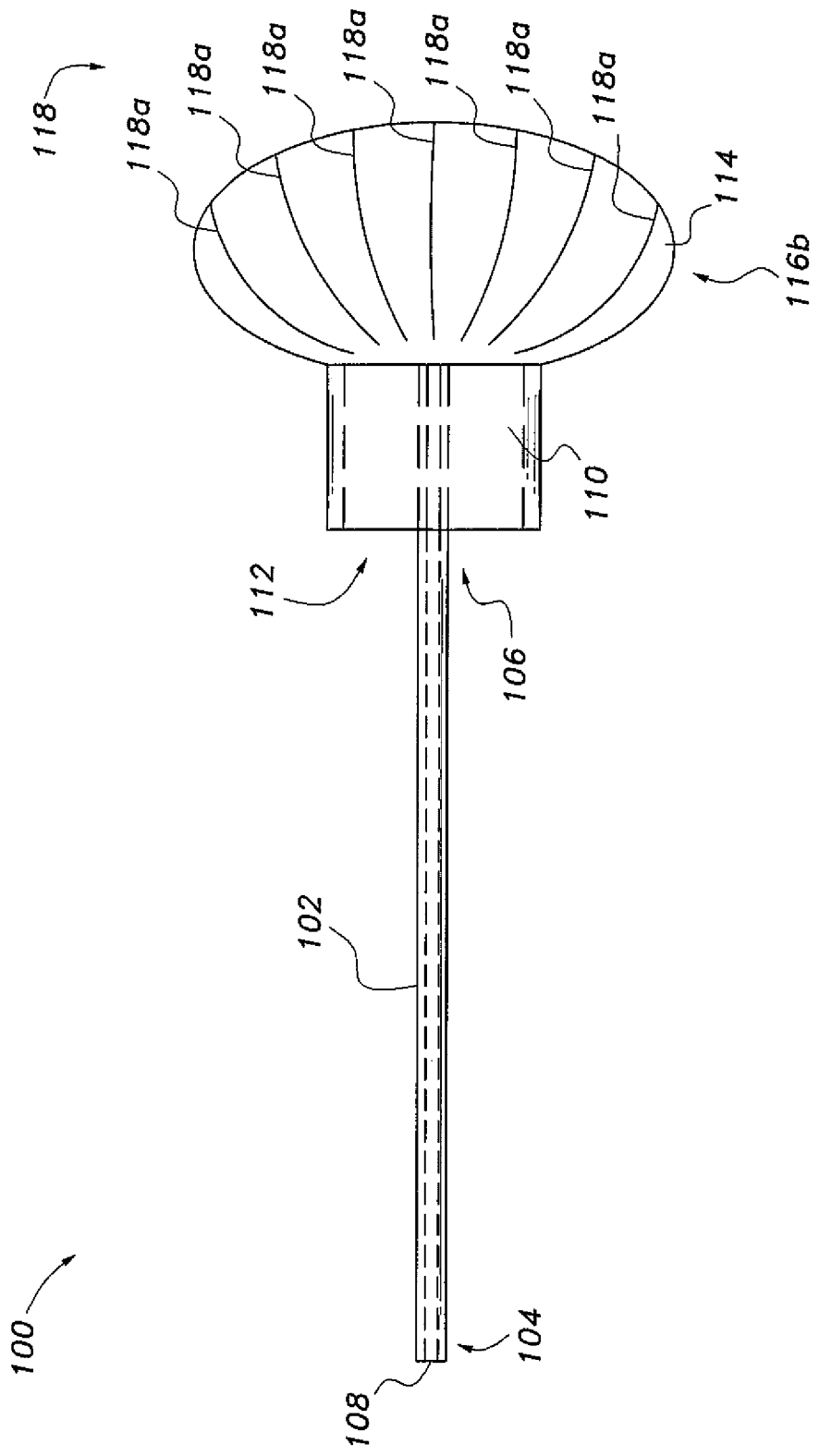
FIG. 2A is a top view of an embodiment of a disrupting mechanism having a plurality of longitudinal breakage lines included in the expandable member of embodiments of a medical material delivery device having a generally ring shape guide according to the present invention.

Referring to FIGS. 2A-2E, various disrupting mechanisms 118 are shown while the expandable member 114 is in the expanded arrangement 116b. As shown in FIG. 2A, the disrupting mechanism 118 can be one or more, desirably a plurality of, longitudinal breakage lines 118a included in the expandable member 114 that cause the expandable member 114 to be placed into the burst open arrangement 116c. The plurality of longitudinal breakage lines 118a are lines that traverse the expandable member 114 and provide a weakened area on the expandable member 114 so that when the expandable member 114 reaches a certain or predetermined volume when filled with the therapeutic agent 124, the plurality of longitudinal breakage lines 118a break and the expandable member 114 ruptures into the burst open arrangement 116c. Alternatively, instead of being volume susceptible, these breakage lines can be designed to be pressure, chemical, electric, temperature or mechanical force susceptible and rupture into at least one of a burst, leak or broken arrangement, depending on the use or application, for example, to deliver the therapeutic agent upon exposure to these triggers.

Figure 2B:
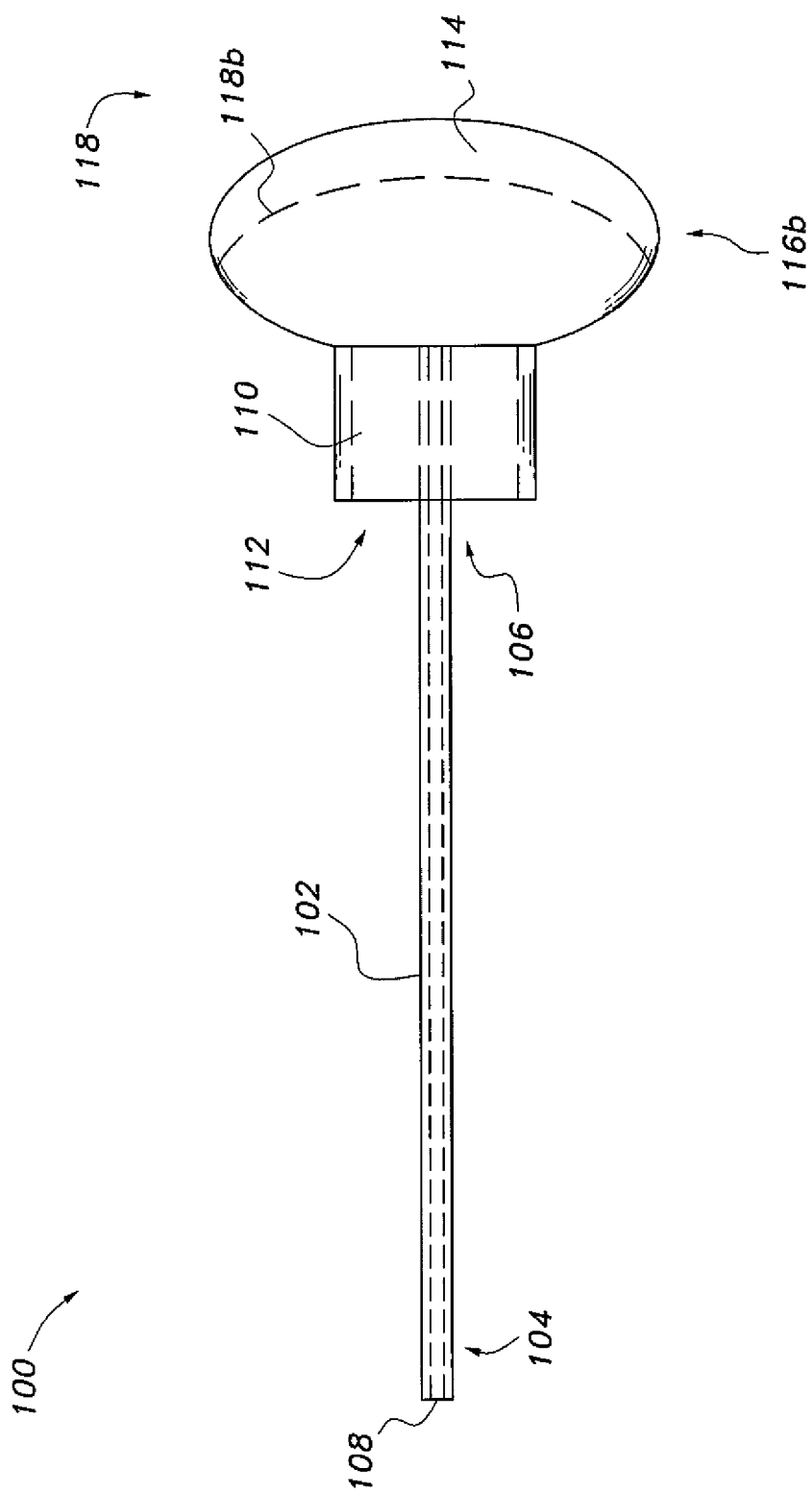
FIG. 2B is a top view of an embodiment of a disrupting mechanism having a generally circumferential breakage line included in the expandable member of embodiments of a medical material delivery device having a generally ring shape guide according to the present invention.

As shown in FIG. 2B, the disrupting mechanism 118 can also be a generally a least one circumferential breakage line 118b included in the expandable member 114. The generally circumferential breakage line 118b traverses generally the circumference of the expandable member 114 and, similar to the plurality of breakage lines 118a, provides for a weakened area on the expandable member 114 so that when the expandable member 114 reaches a certain or predetermined volume when filled with the therapeutic agent 124, the expandable member 114 ruptures into the burst open arrangement 116c. Alternatively, instead of being volume susceptible, these breakage lines can be designed to be pressure, chemical, electric, temperature or mechanical force susceptible and rupture into at least one of a burst, leak or broken arrangement, depending on the use or application, for example, to deliver the therapeutic agent upon exposure to these triggers.

Figure 2C:
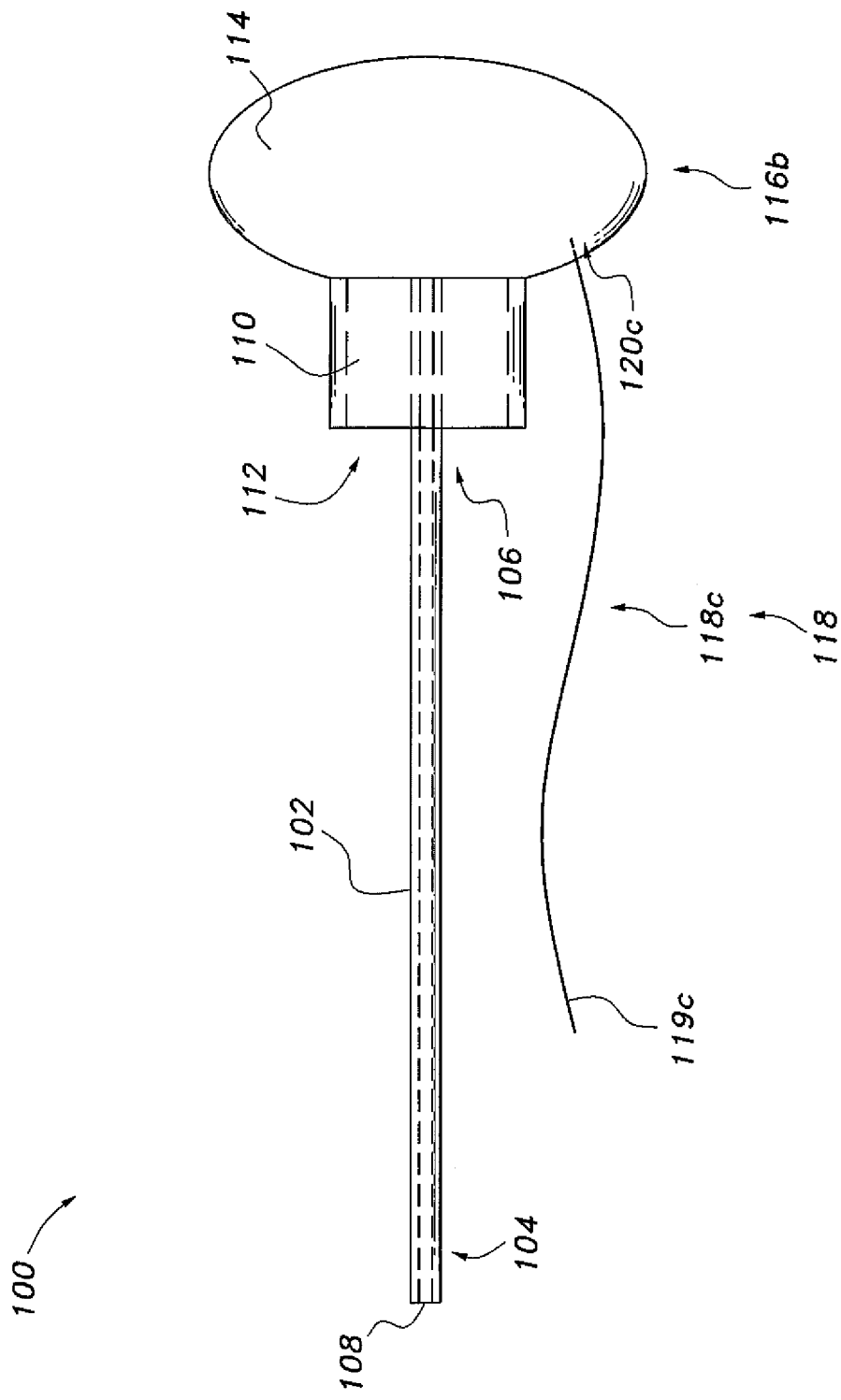
FIG. 2C is a top view of an embodiment of a disrupting mechanism having a string attached to the expandable member of embodiments of a medical material delivery device having a generally ring shape guide according to the present invention.

As shown in FIG. 2C, the disrupting mechanism 118 can be a string disrupting mechanism 118c, such as a string or a wire, for example. For this embodiment, the string 119c is attached to the expandable member 114 at a breakage point 120c. When the user pulls the string 119c, the string 119c will pull apart the breakage point 120c, causing the expandable member 114 to rupture into the burst open arrangement 116c. This rupturing can be assisted by relatively high pressure escaping from the now opened breakage point 120c into the surrounding area outside the expandable member 114.

Figure 2D:
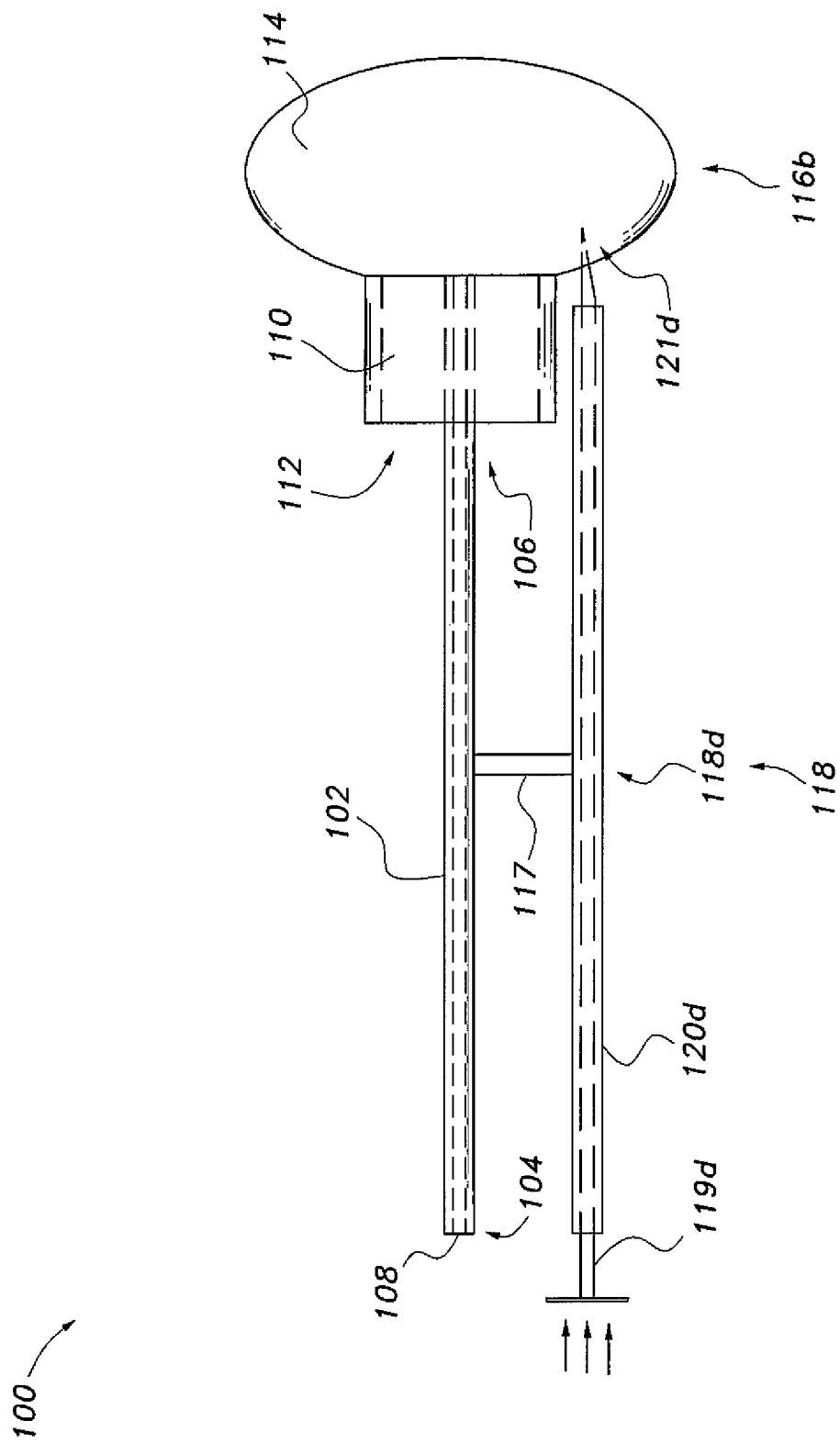
FIG. 2D is a top view of an embodiment of a disrupting mechanism having a needle positioned in communication with the expandable member of embodiments of a medical material delivery device having a generally ring shape guide according to the present invention.

As shown in FIG. 2D, another embodiment has the disrupting mechanism 118 as a needle disrupting mechanism 118d. The needle disrupting mechanism 118d includes a needle 119d and a needle guide 120d that allows for the tip of the needle 119d to pierce the expandable member 114 at a piercing point 121d. When the user directs the needle 119d through the needle guide 120d and pushes the tip of the needle 119d into the piercing point 121d, the expandable member 114 ruptures into the burst open arrangement 116c. The needle disrupting mechanism 118d can be connected to the shaft 102 of the medical material delivery device 100 by a bracket 117, as shown in FIG. 2D.

Similar to the process of rupturing described above with the string disrupting mechanism 118c, the expandable member rupture can be assisted by the relatively high pressure escaping quickly through the hole caused by the needle 119d piercing the expandable member 114. As shown in FIG. 2E, the disrupting mechanism 118 can also be a chemical disrupting mechanism 118e that involves a chemical 119e, such as a solvent or a chemical solvent, applied directly to the expandable member 114. The chemical 119e can react with the expandable member 114 to erode the expandable member 114 until the expandable member 114 at least one of bursts, leaks or becomes broken, such as ruptures into the burst open arrangement 116c. The solvent can be any common or suitable solvent that is safe for use internally with a human patient, for example. Also the disrupting mechanism can include the application of heat, an electric current, a mechanical force, radiofrequency energy, microwave energy, ultrasound, laser, coblation plasma field or other suitable disrupting triggers to the expandable member, for example.

Figure 3A:
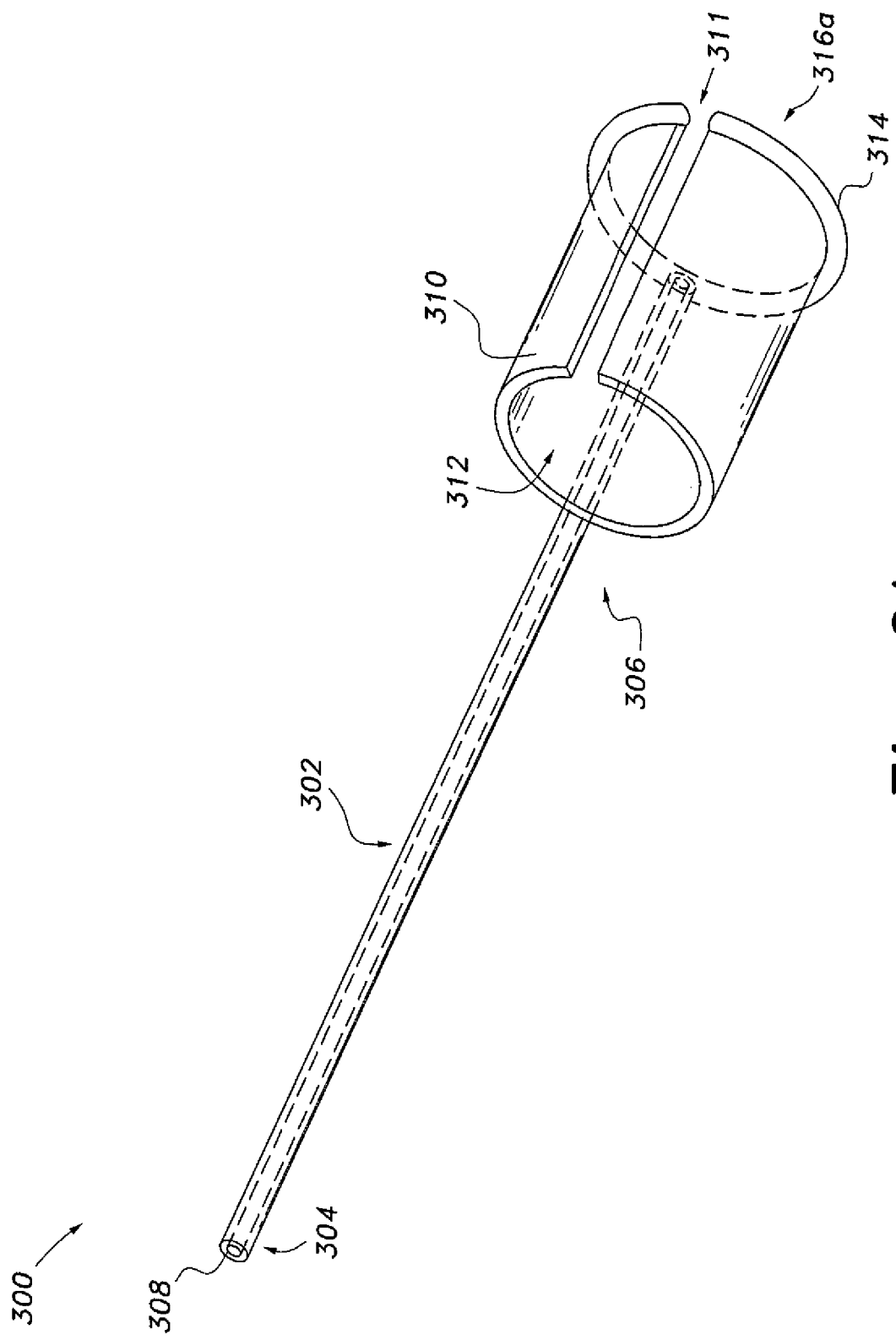
FIG. 3A is a perspective view of an embodiment of a medical material delivery device having a generally split ring shape guide according to the present invention.
Figure 3B:
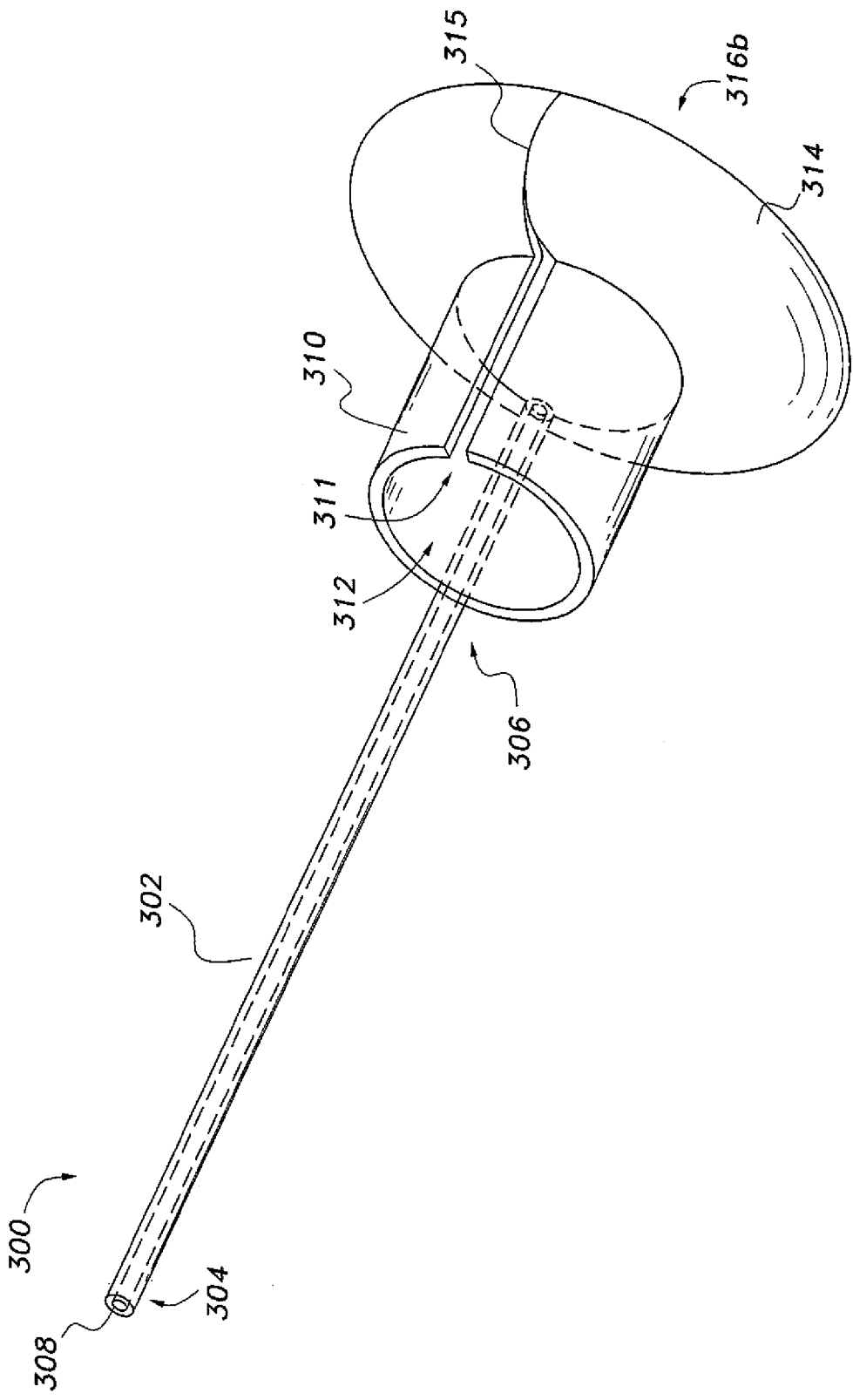
FIG. 3B is a perspective view of an embodiment of an inflated expandable member of embodiments of a medical material delivery device having a generally split ring shape guide according to the present invention.

Another embodiment of a medical material delivery device 300 is provided in FIGS. 3A and 3B. Similar to the medical material delivery device 100, the medical material delivery device 300 includes a shaft 302 that has an open ended lumen 308 that traverses the length of the shaft 302. One open end of the lumen 308 is at the proximal end 304 of the shaft 302 and the other open end is located at the distal end 306 of the shaft 302. This open end of the lumen 308 located at the distal end 306 inserts into and empties into an expandable member 314.

The expandable member 314 is positioned in conjunction with a guide 310 and expands when filled by a therapeutic agent that is delivered by the lumen 308. Similar to therapeutic agent 124 of the medical material delivery device 100, the therapeutic agent used with medical material delivery device 300 can be, for example, the patient's own clotted blood, thrombin, fibrin, a liquid embolic material, a lipid based sealing material, a common coagulation or embolization material, a phase changeable material such as acrylic bone cement, or any other common or suitable implantable medical material.

The guide 310 is positioned at the distal end 306 of the shaft 302 and is adapted for positioning in conjunction with a bodily part, such as a blood vessel. As shown in FIGS. 3A and 3B, the guide 310 is configured in a generally split ring shape and includes a slit 311 and a channel 312 that can accommodate a medical instrument, for example. The diameter of the generally split ring shape of the guide 310 can be adjusted because of the generally split ring shape, allowing for an increased diameter if needed. For example, if a user was initially using a needle as the medical instrument, and wanted to switch to a different medical instrument, such as a cannula, which typically has a larger diameter than a needle, the user would simply remove the needle from the channel 312 of the guide 310 and replace it with the cannula, and the guide 310 can adjust to a relatively the larger diameter of the cannula since the generally split ring shape of the guide 310 can be of a size to allow for an increase of diameter.

Therefore, a user likely would not have to replace the guide 310 during a procedure to accept another medical instrument. Further, the guide 310 can be made from a suitable material, such as a medical grade memory shape material, an example of such material being nitinol, that can allow for the generally split ring shape guide 310 to adapt around a medical instrument and to also allow for the generally split ring shape guide 310 to return to its original diameter once the medical instrument has been removed from the channel 312.

The expandable member 314 is similar to expandable member 114 of the medical material delivery device 100, and, similarly, is adapted to be in communication with a bodily part. The expandable member 314 and the expandable member 114, as well as other expandable members described herein, can be made from various suitable materials, such as an elastic medical grade material, a plastic material or a textile material, for example, that can allow for the expandable member, such as the expandable member 314 and the expandable member 114, to be deflated, inflated/expanded and, when appropriate, disrupted, such as by being burst. Further, expandable member 314 can be placed into at least three separate arrangements, such as an unexpanded arrangement 316a shown in FIG. 3A and an expanded arrangement 316b as shown in FIG. 3B, or can be placed in other arrangements where the expandable member 314 is in one or more partially filled states, for example.

The expandable member 314 can have a slit 315 when the expandable member 314 is in the expanded arrangement 316b because of the generally split ring shape of the guide 310. The third arrangement is a burst open arrangement where the expandable member 314 is ruptured and the therapeutic agent, such as the therapeutic agent 124, contained within the expandable member 314 is delivered to the bodily part that is in communication with the expandable member 314, similar to the burst open arrangement 116c of FIG. 7E.

Figure 4A:
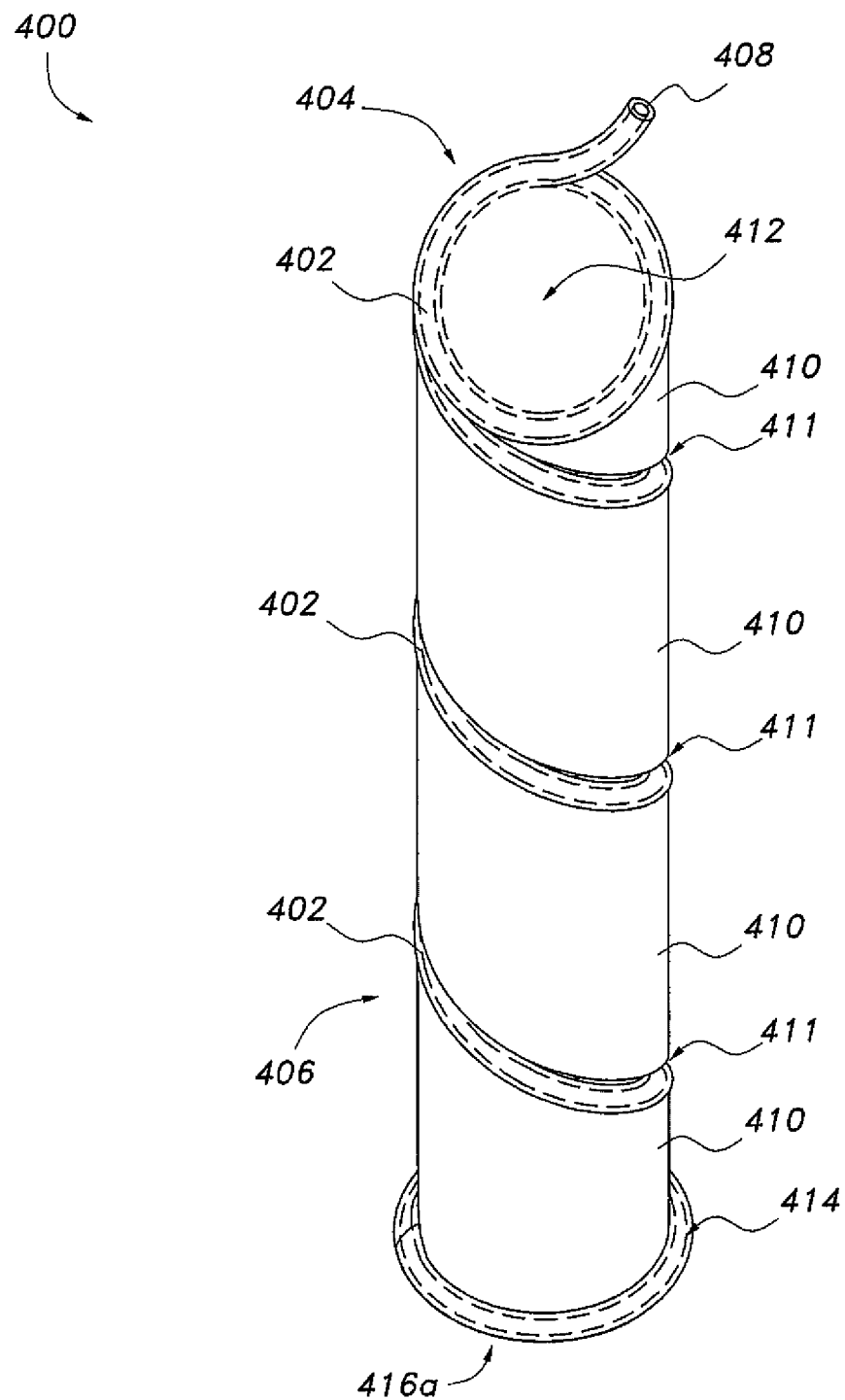
FIG. 4A is a front view of an embodiment of a medical material delivery device having a guide as a sheath configured to wrap onto a medical instrument according to the present invention.
Figure 4B:
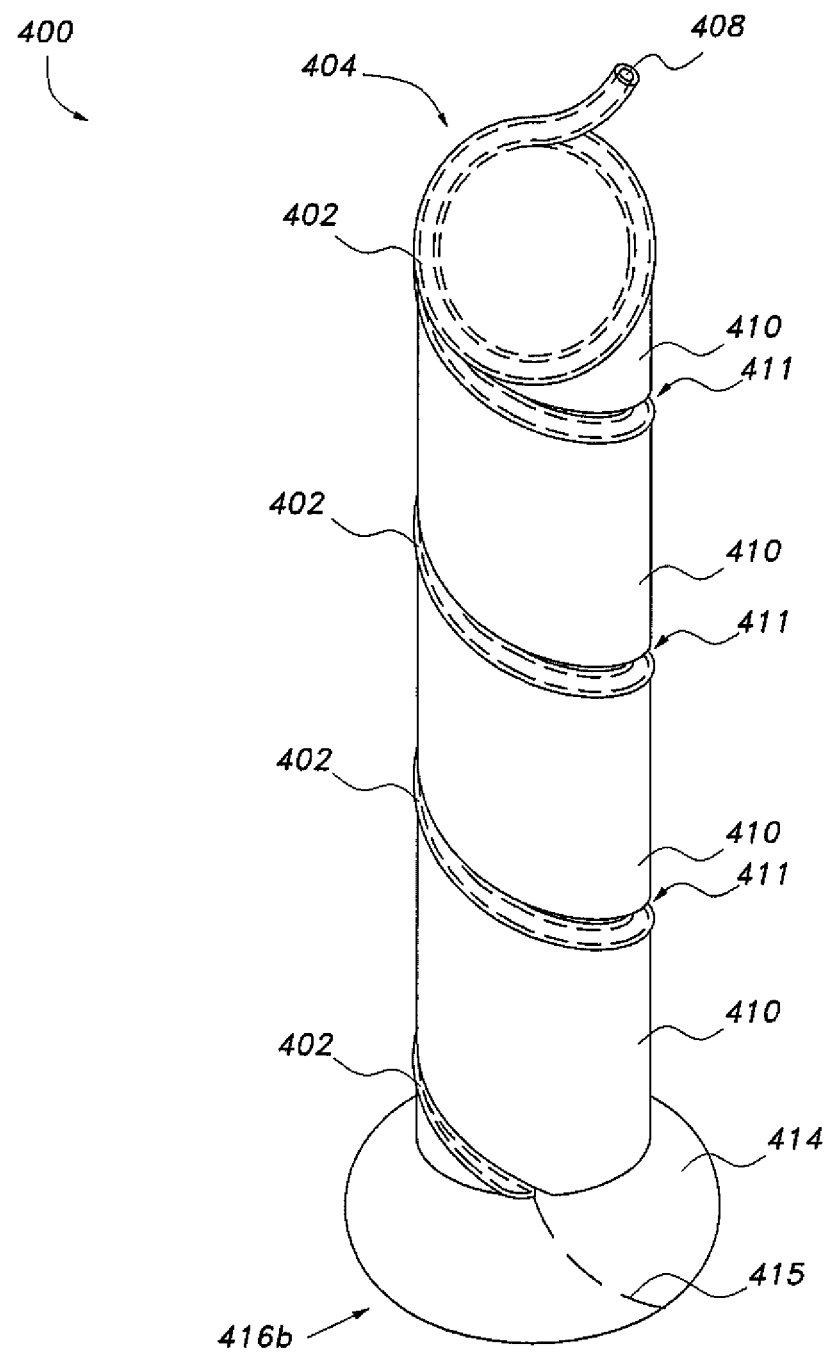
FIG. 4B is a perspective view of an embodiment of an inflated expandable member of embodiments of a medical material delivery device having a guide as a sheath configured to wrap onto a medical instrument according to the present invention.

Another embodiment of a medical material delivery device 400 is provided in FIGS. 4A and 4B. Medical material delivery device 400 includes a shaft 402 having a proximal end 404 and a distal end 406. An open ended lumen 408 traverses the length of the shaft 402 and, similar to medical material delivery devices 100 and 300, one open end is at the proximal end 404 of the shaft 402 and the other open end is located at the distal end 406 of the shaft 402. This open end of the lumen 408 located at the distal end 406 inserts into and empties into an expandable member 414.

The expandable member 414 is positioned in conjunction with a guide 410 and expands when filled by a therapeutic agent, such as the therapeutic agent 124, that is delivered by the lumen 408. Similar to the therapeutic agent 124 of medical material delivery device 100, the therapeutic agent used with medical material delivery device 400 can be the patient's own clotted blood, thrombin, fibrin, a liquid embolic material, a lipid based sealing material, a common coagulation or embolization material, a phase changeable material such as acrylic bone cement, or any other suitable or common implantable medical material, for example. As shown in FIGS. 4A and 4B, the guide 410 can be a flexible sheath that can be configured to wrap onto a medical instrument. The channel 412 of the guide 410 is formed once the guide 410 is wrapped onto the medical instrument.

Further, the shaft 402 can be integrally configured in the sheath forming the guide 410 so that the shaft 402 and the guide 410 can be integrally wrapped together onto the medical instrument. Or, depending on the particular needs or application, the shaft 402 can be separate from guide 410 and can be simply wrapped around the guide 410 while the guide 410 is wrapped onto the medical instrument, for example. When the guide 410 is wrapped onto the medical instrument, a plurality of slits 411 are formed from an edge of the sheath being adjacent to another edge of the sheath forming the guide 410, for example.

The expandable member 414 is similar to expandable members 114 and 314, including being in communication with a bodily part and being made from an elastic medical grade material, or other suitable material, that can allow for expansion. Expandable member 414 can also be placed into at least three separate arrangements, such as an unexpanded arrangement 416a shown in FIG. 4A and an expanded arrangement 416b as shown in FIG. 4B, or can be placed in other arrangements where the expandable member 414 is in one or more partially filled states, for example.

The expandable member 414 can have a slit 415 when the expandable member 414 is in the expanded arrangement 416b, the slit 415 typically being included in the expandable member 414, particularly when the guide 410 is a sheath that wraps onto the medical instrument, for example. The third arrangement is a burst open arrangement, similar to the burst open arrangement 116c of FIG. 7E, where the expandable member 414 is ruptured and the therapeutic agent, such as the therapeutic agent 124, contained within the expandable member 414 is delivered to the bodily part that is in communication with the expandable member 414.

Another embodiment of a medical material delivery device 500 is provided in FIGS. 5A-5F. Medical material delivery device 500 is similar to medical material delivery device 100, but also includes a medical instrument 522 and a bodily fluid locator 523, such as a vascular locator. Similar to medical material delivery devices 100, 300 and 400, medical material delivery device 500 has a shaft 502 having a proximal end 504 and a distal end 506, and an open ended lumen 508 that traverses the length of the shaft 502. One of the open ends of the lumen 508 is located at the proximal end 504 and the other open end is located at the distal end 506, with this open end inserting into and emptying into an expandable member 514.

The expandable member 514 is positioned in conjunction with a guide 510 and expands when filled by a therapeutic agent, such as therapeutic agent 124, that is delivered by the lumen 508. Similar to therapeutic agent 124 of medical material delivery device 100, the therapeutic agent used with medical material delivery device 500 can be the patient's own clotted blood, thrombin, fibrin, a liquid embolic material, a lipid based sealing material, a common coagulation or embolization material, a phase changeable material such as acrylic bone cement, or any other suitable or common implantable medical material, for example.

Figure 5A:
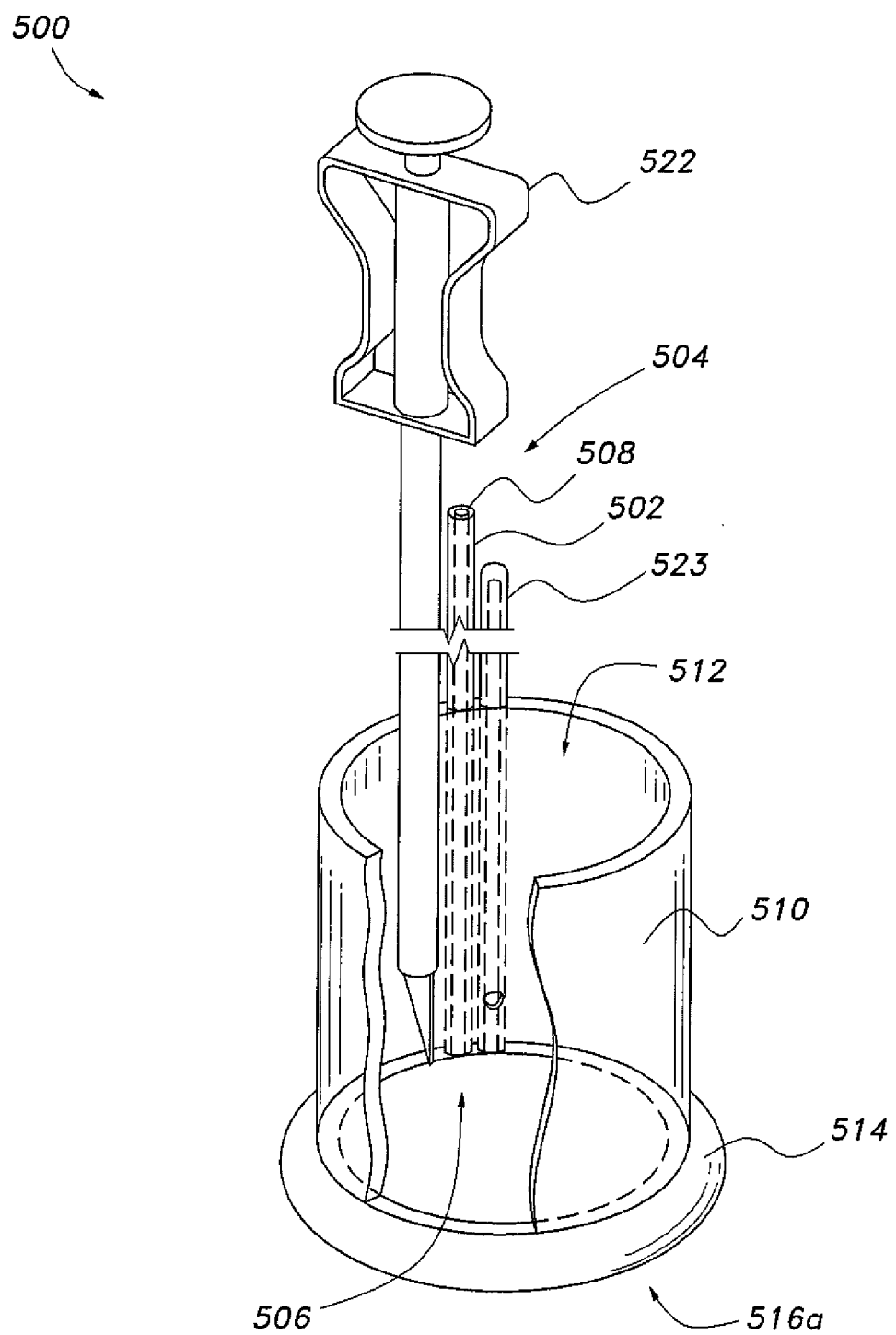
FIG. 5A is a front view of an embodiment of a medical material delivery device having a medical instrument and a bodily fluid locator, such as a vascular locator, according to the present invention.
Figure 5B:
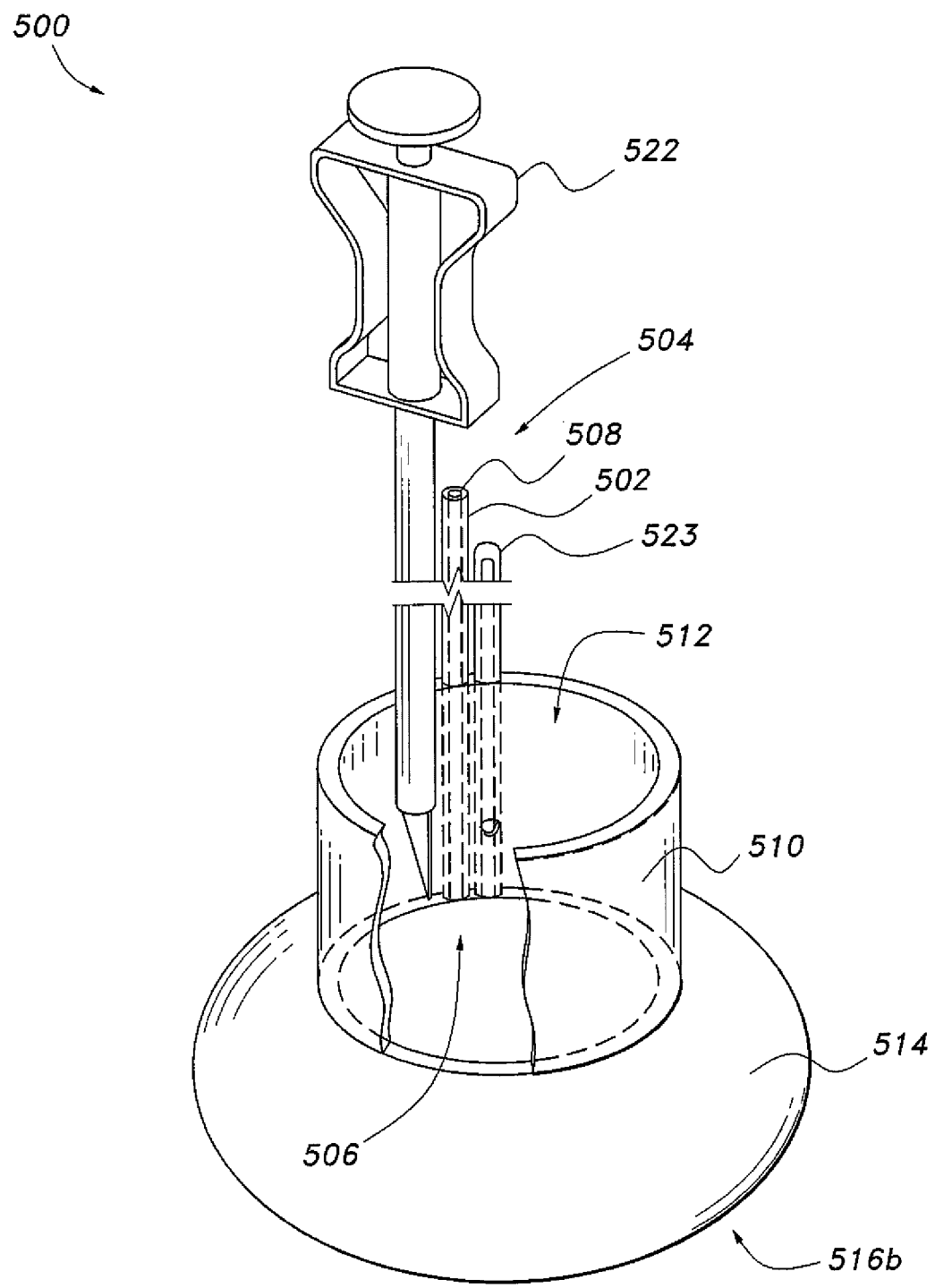
FIG. 5B is a perspective view of an embodiment of an inflated expandable member of embodiments of a medical material delivery device having a medical instrument and a bodily fluid locator, such as a vascular locator, according to the present invention.

The guide 510 is positioned at the distal end 506 of the shaft 502 and is adapted for positioning in conjunction with a bodily part, such as a blood vessel. As shown in FIGS. 5A and 5B, the guide 510 is configured in a generally ring shape and includes a channel 512 that accommodates the medical instrument 522. The medical instrument 522 is adapted for insertion into a bodily part, such as a blood vessel, and can be attached directly to the shaft 502 or the guide 510 or the channel 512 of the guide 510, depending on the particular need or application. Similar to medical material delivery devices 100, 300 and 400, the medical instrument 522 can be a number of different instruments, including a trocar as shown in FIGS. 5A and 5B, a cannula, a guide wire, a scalpel, or any other suitable or common medical instrument that is used for invasive medical procedures, for example.

In addition to the medical instrument 522, the bodily fluid locator 523, such as a vascular locator, is positioned in conjunction with the shaft 502. The bodily fluid locator 523 can be a clear tube having a closed end located at the proximal end 504 of the shaft 502 and an open end located at the distal end 506 of the shaft 502. The open end of the bodily fluid locator 523 is in communication with a bodily part, such as a blood vessel, and visually indicates to a user that the bodily part, such as a blood vessel, has been located and punctured by the presence of blood or other bodily fluid in the bodily fluid locator 523, and the bodily fluid locator 523 can also indicate location of the bodily part by a tactile sensation or response, or both, for example.

When the bodily part, such as the blood vessel, is punctured, blood, or a corresponding bodily fluid, will flow out from the bodily part, such as the blood vessel, and into the open end of the bodily fluid locator 523. As the blood, or other bodily fluid, flows into the bodily fluid locator 523, it will be visible to the user through the clear tubing, notifying the user that the blood vessel or other bodily part has been found and punctured and that the medical material delivery device 500 is in communication with the blood vessel wall or other bodily part.

Figure 5C:
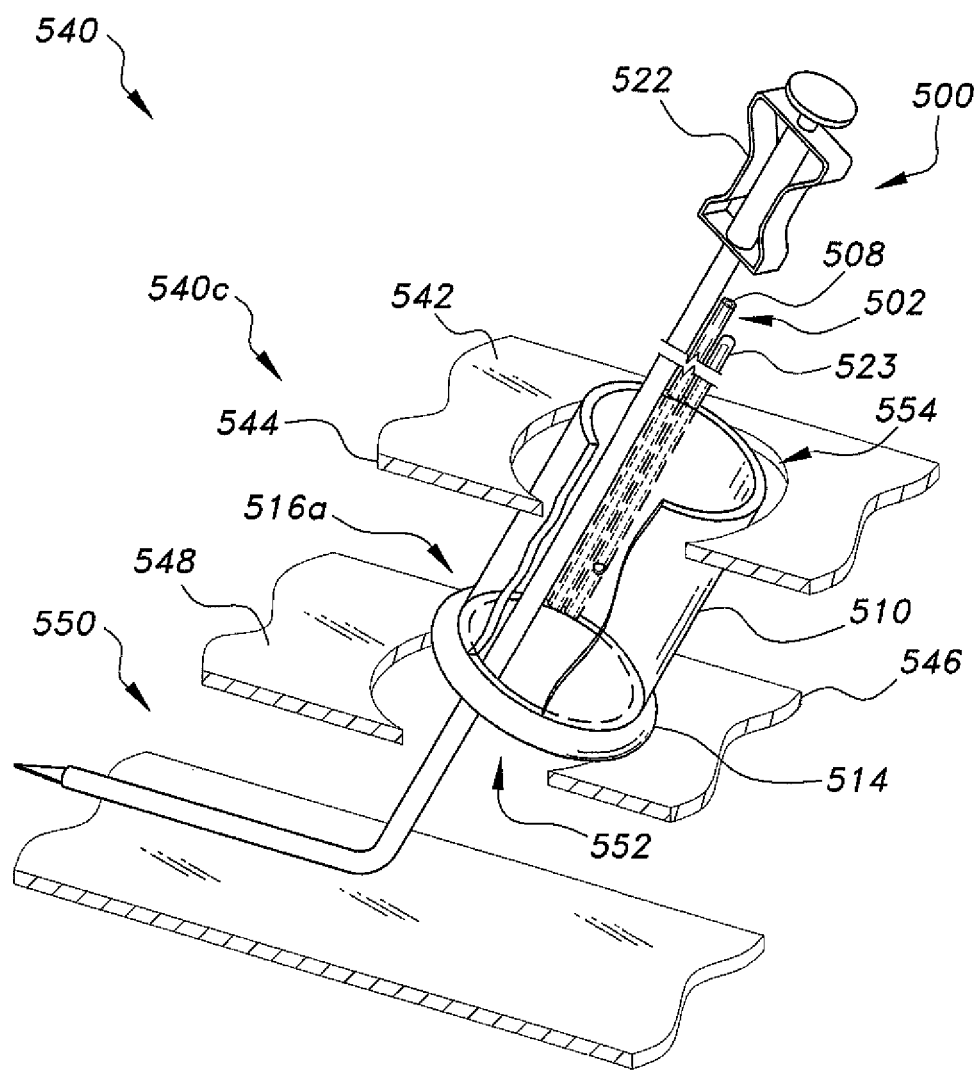
FIG. 5C is an environmental view of an embodiment of a first step of a method for sealing a puncture in a blood vessel using the embodiments of the medical material delivery device of FIGS. 5A-5B according to the present invention.
Figure 5D:
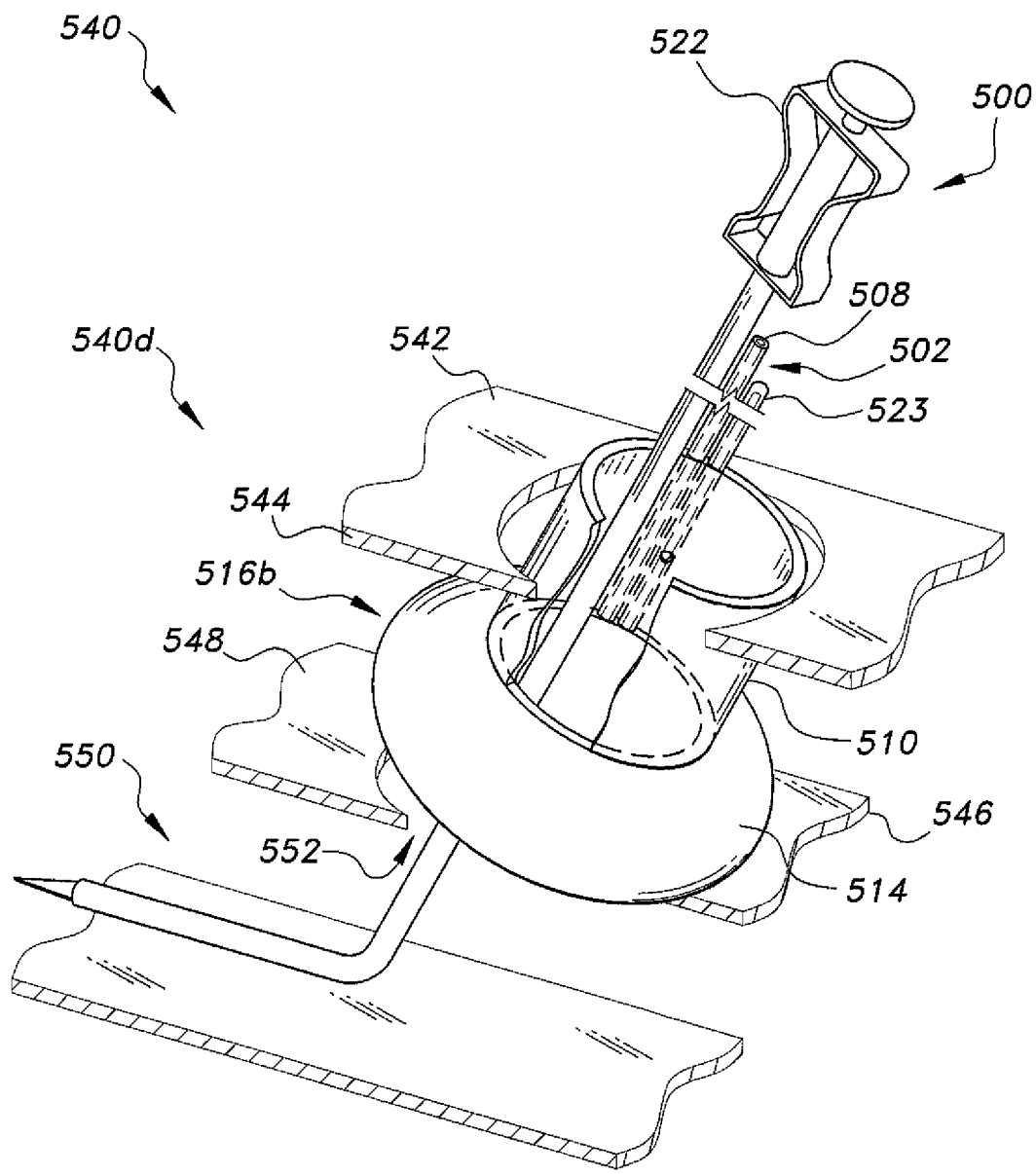
FIG. 5D is an environmental view of an embodiment of a second step of a method for sealing a puncture in a blood vessel using the embodiments of the medical material delivery device of FIGS. 5A-5B according to the present invention.
Figure 5E:
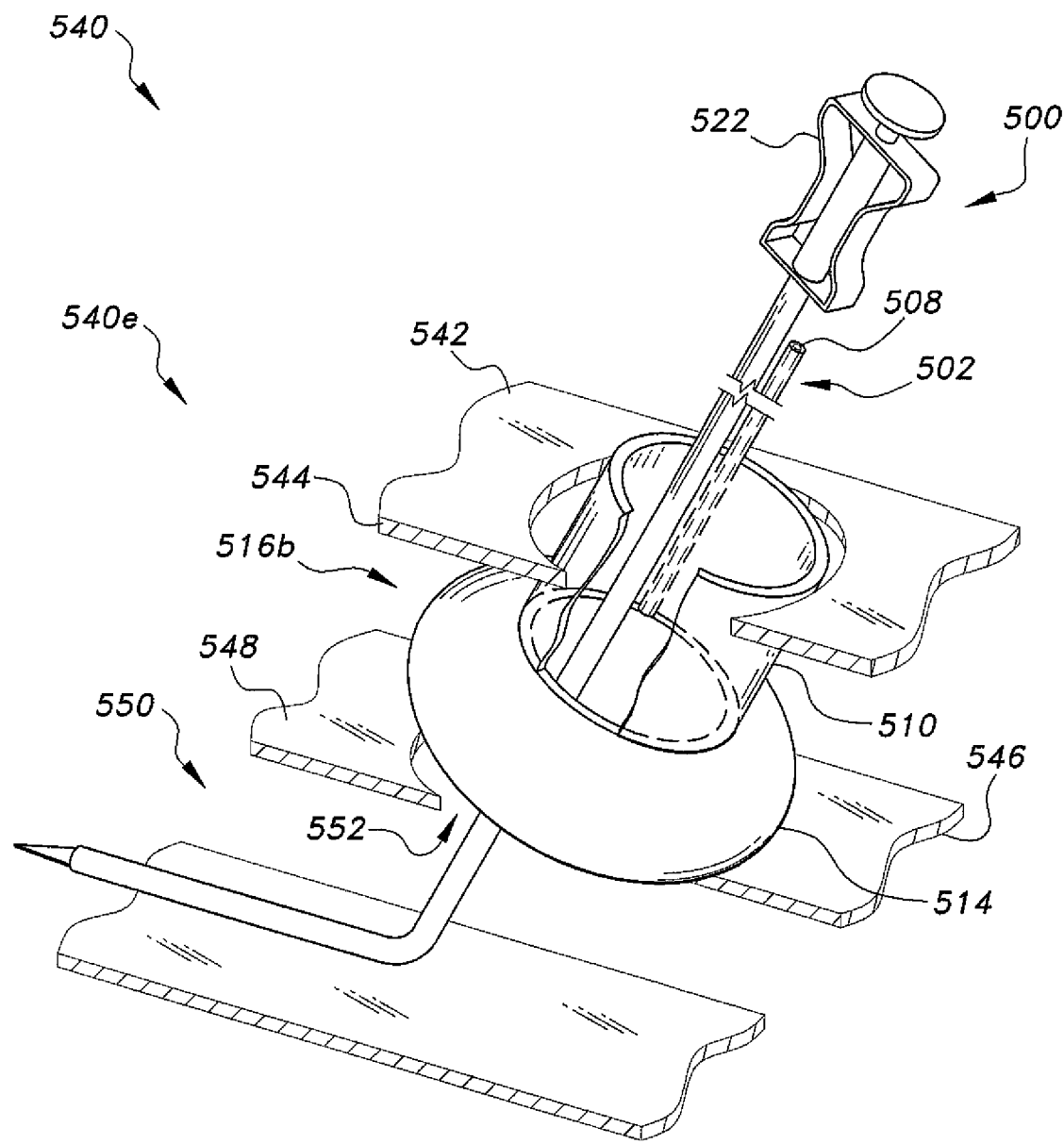
FIG. 5E is an environmental view of an embodiment of a third step of a method for sealing a puncture in a blood vessel using the embodiments of the medical material delivery device of FIGS. 5A-5B according to the present invention.
Figure 5F:
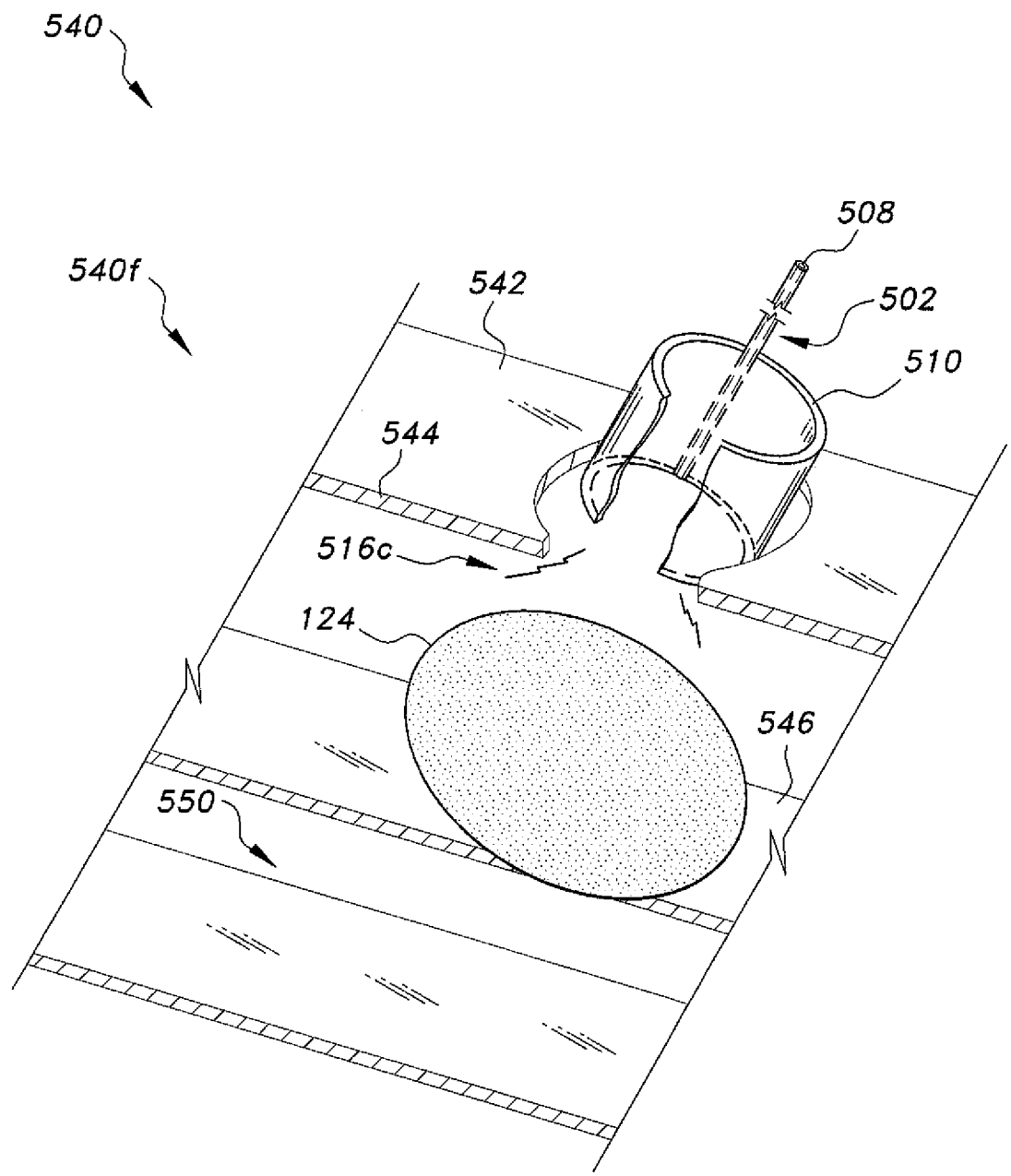
FIG. 5F is an environmental view of an embodiment of a fourth step of a method for sealing a puncture in a blood vessel using the embodiments of the medical material delivery device of FIGS. 5A-5B according to the present invention.

Referring to FIGS. 5C-5F, a method 540 of sealing a blood vessel 546 is shown. The first step 540c of the method 540 is to position the medical material delivery device 500 in conjunction with a blood vessel 546 by passing the medical material delivery device 500 through the skin 542 and through the skin layer 544. When the medical material delivery device 500 is passed through the skin 542 and the skin layer 544, a skin puncture site 554 is formed. Further, as shown in FIGS. 5C-5E, the medical instrument 522 of the medical material delivery device 500 punctures the blood vessel 546 and enters the interior area 550 through a blood vessel puncture site 552 through an exterior surface 548 of the blood vessel 546. The user can be notified that the medical instrument 522 has punctured the blood vessel 546 and that the medical material delivery device 500 is positioned in conjunction with the blood vessel by the visual indication of blood flowing through the bodily fluid locator 523. During the first step 540c of the method 540, the expandable member 514 remains in an unexpanded arrangement 516a.

A second step 540d of the method 540 includes placing the expandable member 514 of the medical material delivery device 500 in an expanded arrangement 516b from the unexpanded arrangement 516a so that the expandable member 514 covers at least a portion of the blood vessel puncture site 552 and can also cover a portion of the exterior surface 548 of the blood vessel 546, as shown in FIG. 5D. The user can continue to be notified that the expendable member 514 now in the expanded arrangement 516b is positioned in conjunction with at least a portion of the blood vessel puncture site 552 by visual indication of the continued flow of blood through the bodily fluid locator 523.

A third step 540e of the method 540 involves removing the bodily fluid locator 523 from the medical material delivery device 500 since the user has already been notified in the previous steps 540c and 540d that the medical material delivery device 500 is in communication with the blood vessel 546. However, if the user so desires, the user can continue to have the bodily fluid locator 523 remain attached to the medical material delivery device 500. A fourth step 540f of the method 540 involves the expandable member 514 being placed from the expanded arrangement 516b into the burst open arrangement 516c. By placing the expandable member 514 into the burst open arrangement 516c, a therapeutic agent, such as therapeutic agent 124, can be delivered to the blood vessel puncture site 552.

Figure 6A:
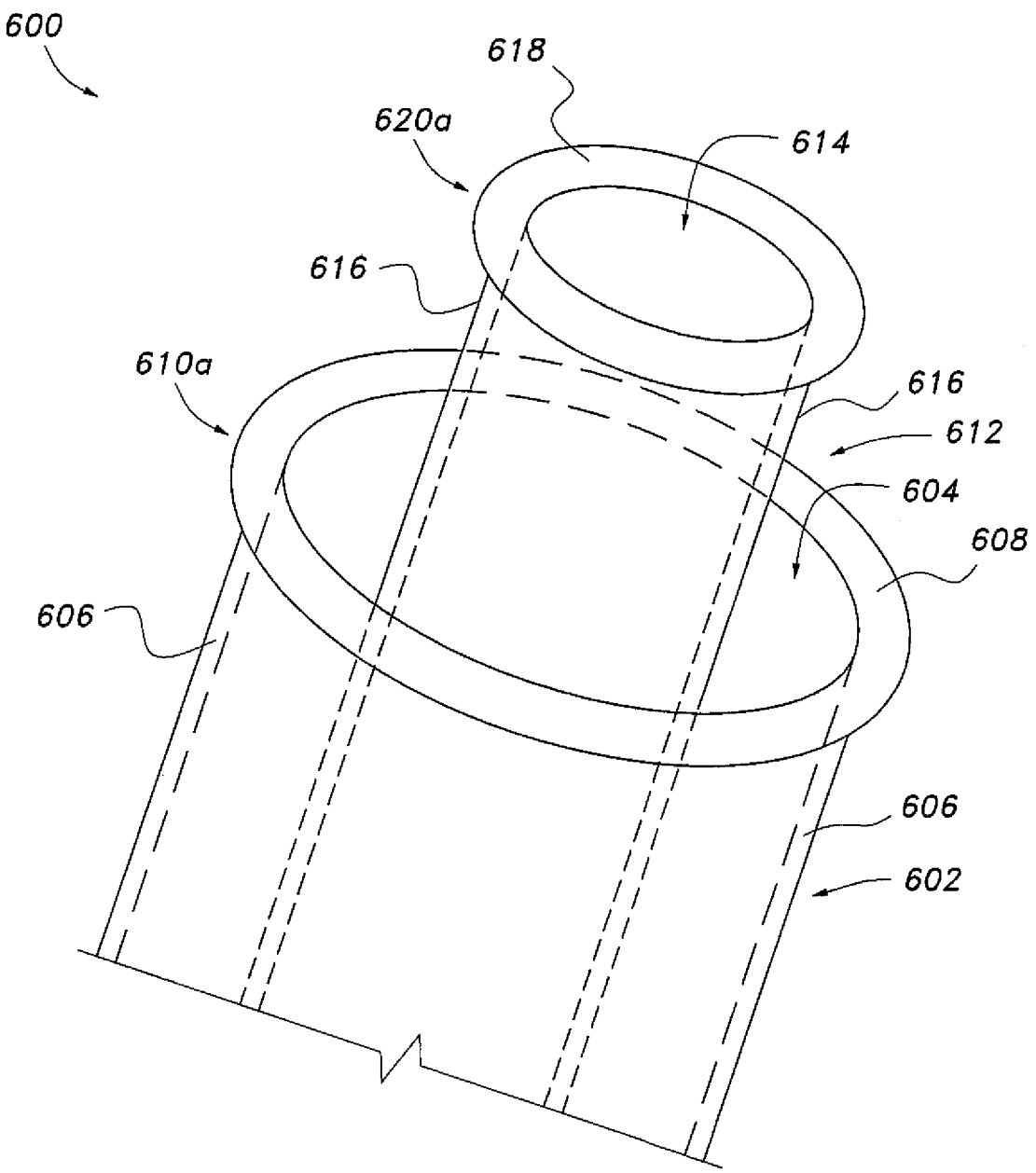
FIG. 6A is a sectional view of an embodiment of a medical material delivery device having an inner shaft with an expandable member positioned within an outer shaft having an expandable member according to the present invention.
Figure 6B:
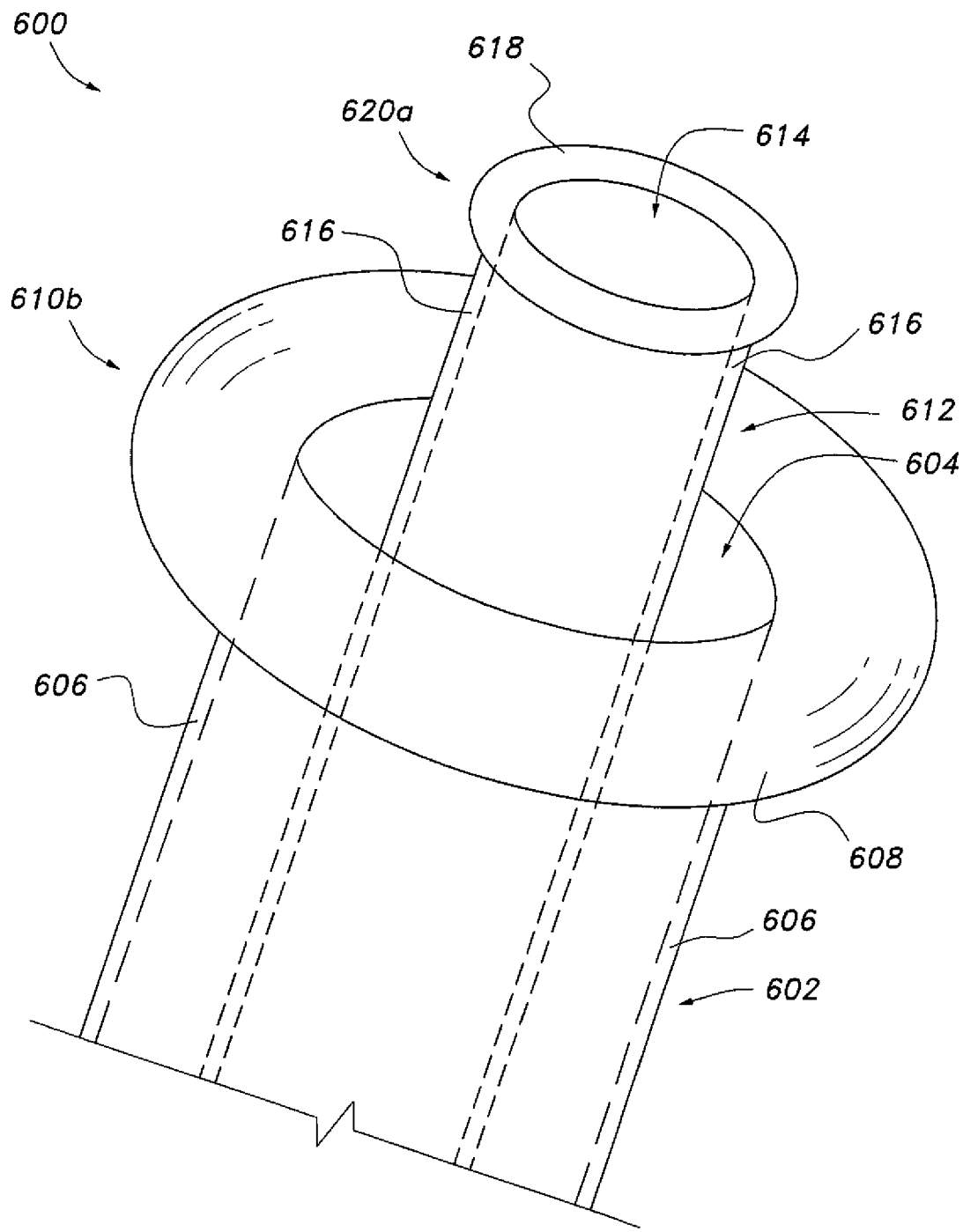
FIG. 6B is a sectional view of an embodiment of an inflated expandable member of the outer shaft of embodiments of a medical material delivery device having an inner shaft with an expandable member positioned within an outer shaft having an expandable member according to the present invention.
Figure 6C:
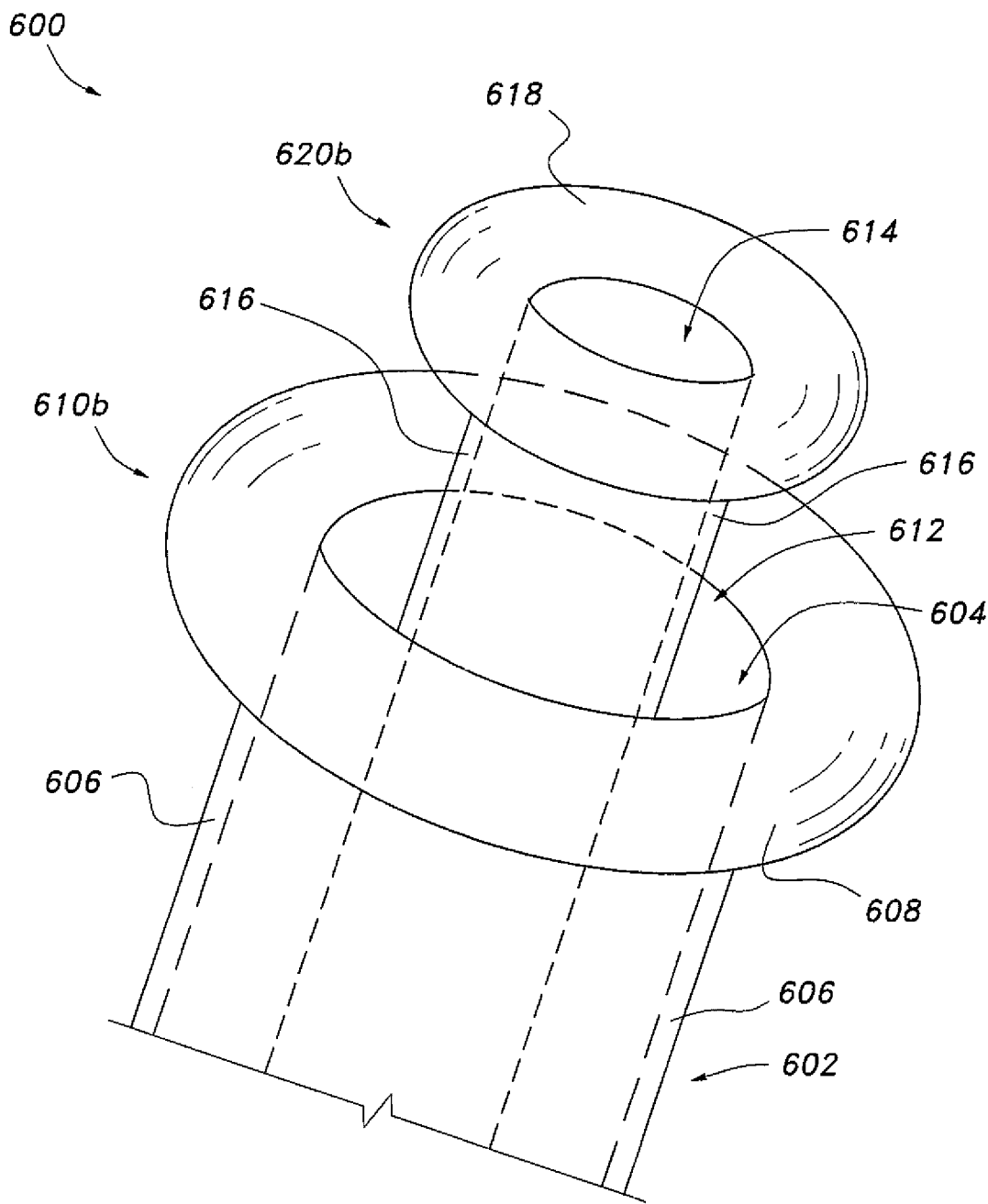
FIG. 6C is a sectional view of an embodiment of an inflated expandable member of the outer shaft and an inflated expandable member of the inner shaft of embodiments of a medical material delivery device having an inner shaft with an expandable member positioned within an outer shaft having an expandable member according to the present invention.

Another embodiment of a medical material delivery device 600 is provided for in FIGS. 6A-6C. The medical material delivery device 600 has an outer shaft 602 that has a first lumen 604 that is configured to accept an inner shaft 612. The outer shaft 602 and the inner shaft 612 each have an expandable member made from an elastic medical grade material that are positioned on the exterior of the respective shaft. Also, the outer shaft 602 and the inner shaft 612 can be arranged in a telescoping relation to each other, such as illustrated in FIGS. 6A-6C, for example.

The first expandable member 608 is positioned on the exterior of the outer shaft 602 and is filled for expansion by a therapeutic agent 624 that is delivered to the first expandable member 608 through a first delivery member 606. The first delivery member 606 is positioned in association with the outer shaft 602 and can be located inside the lumen 604 of the outer shaft 602 or can be positioned on the exterior of the outer shaft 602, depending on the particular needs or application, as long as the first delivery member 606 remains in communication with the first expandable member 608 so that the therapeutic agent 624 can be delivered into the first expandable member 608.

Figure 8A:
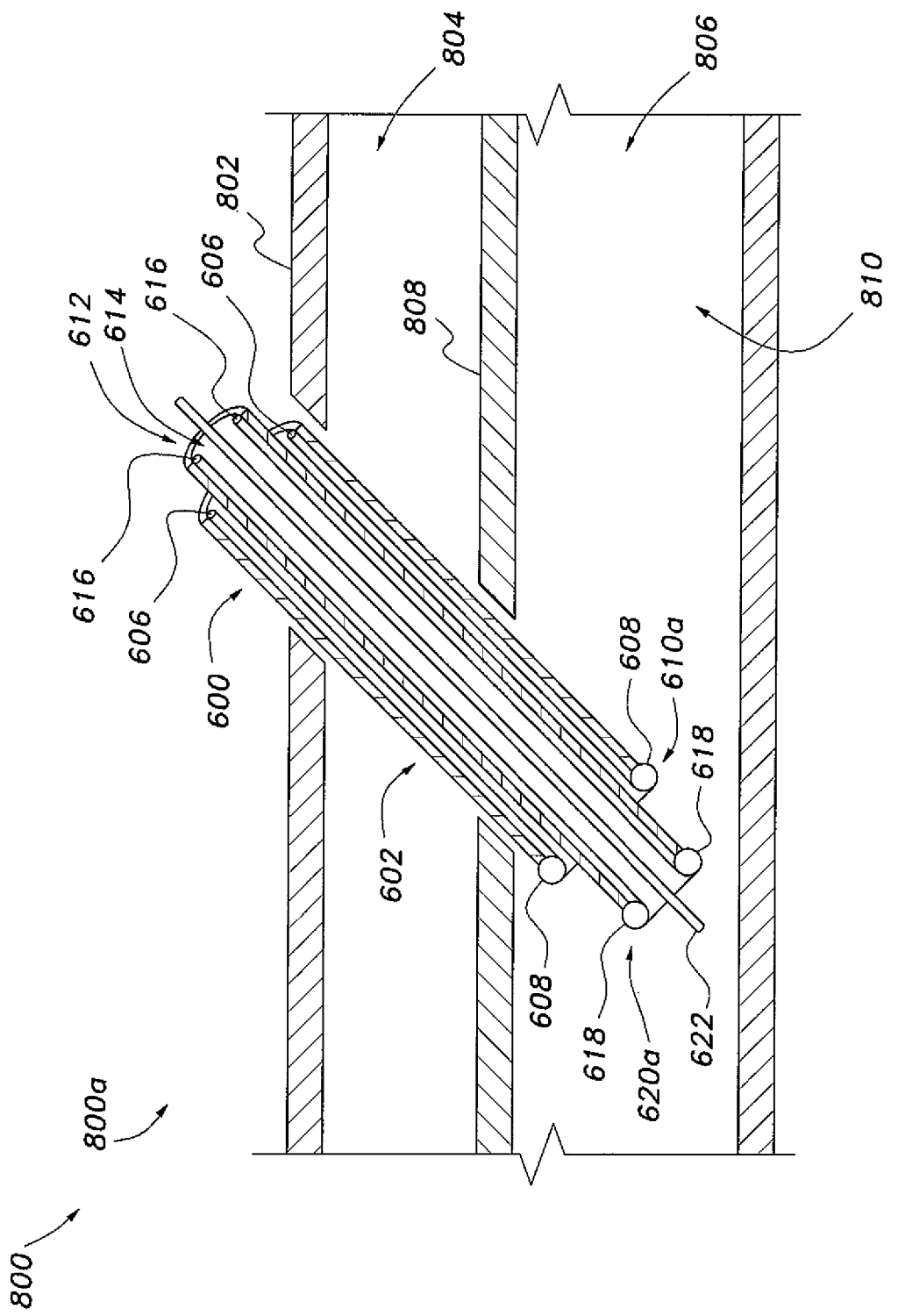
FIG. 8A is an environmental cross section of an embodiment of a first step of another method for sealing a puncture in a blood vessel using embodiments of a medical material delivery device according to the present invention.

When the therapeutic agent 624 is delivered through the first delivery member 606 and into the first expandable member 608, the first expandable member 608 will expand in the same manner and arrangements as expandable members 114, 314, 414 and 514 of medical material delivery devices 100, 300, 400 and 500 respectively. Also, the expandable members 114, 314, 414, 514 and 614 of medical material delivery devices 100, 300, 400, 500 and 600 can be of various suitable shapes and sizes, as, for example, a sphere, sphere like, teardrop or ring like shape. The first expandable member 608 can be positioned into an unexpanded arrangement 610a as shown in FIG. 6A, an expanded arrangement 610b as shown in FIG. 6B, and a burst open arrangement 610c as shown in FIG. 8F. When the first expandable member 608 is in the burst open arrangement 610c, the therapeutic agent 624 can be delivered to a blood vessel puncture site 812, shown in FIGS. 8F-8G, for example.

Figure 8B:
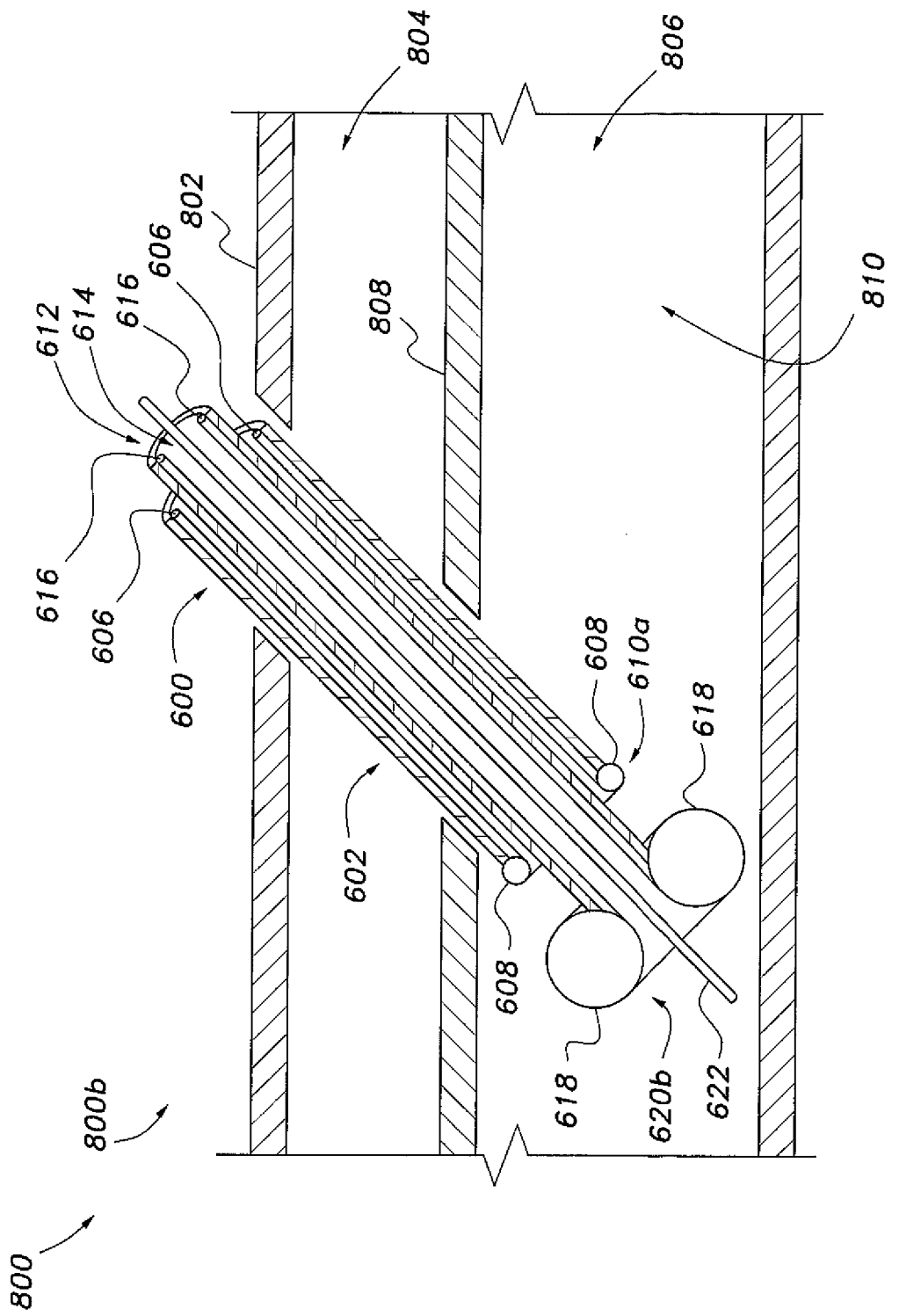
FIG. 8B is an environmental cross section of an embodiment of a second step of another method for sealing a puncture in a blood vessel using embodiments of a medical material delivery device according to the present invention.
Figure 8C:
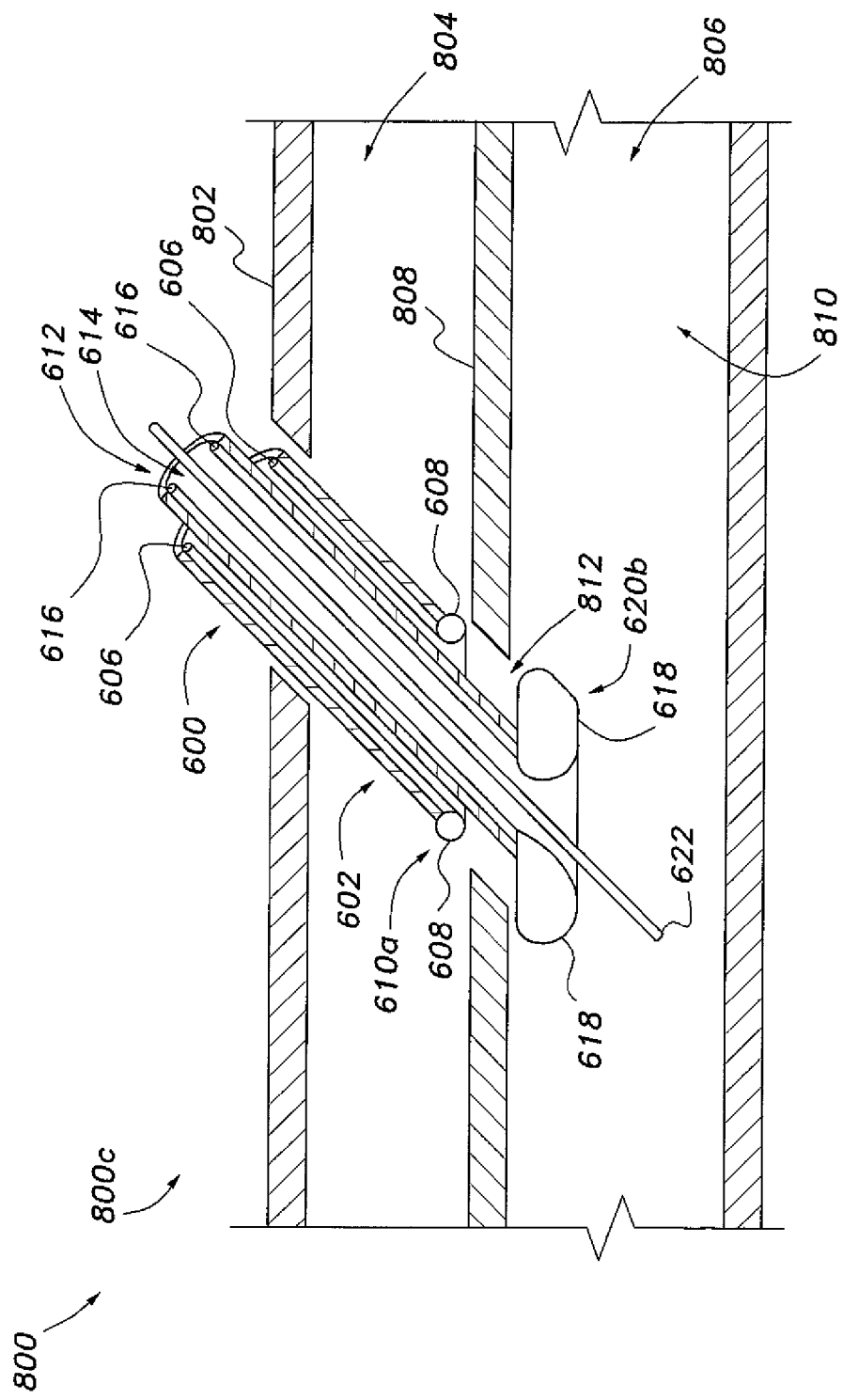
FIG. 8C is an environmental cross section of an embodiment of a third step of another method for sealing a puncture in a blood vessel using embodiments of a medical material delivery device according to the present invention.
Figure 8D:
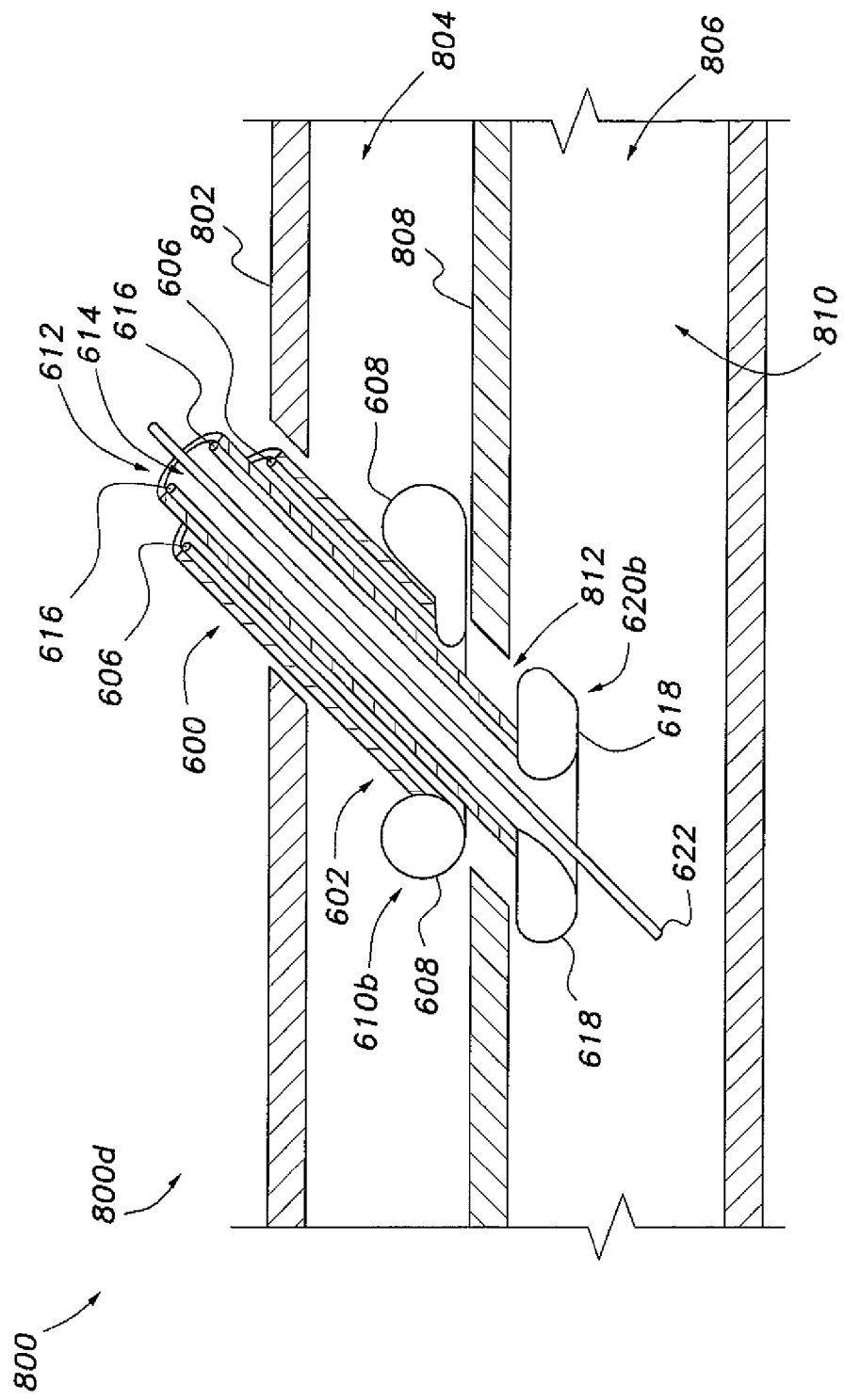
FIG. 8D is an environmental cross section of an embodiment of a fourth step of another method for sealing a puncture in a blood vessel using embodiments of a medical material delivery device according to the present invention.

A second expandable member 618 as can also be of various suitable shapes and sizes, as, for example, a sphere, sphere like, teardrop like or ring like shape, is positioned on the exterior of the inner shaft 612 and is filled for expansion by a suitable fluid or material to expand the second expandable member 618, as can include an aqueous solution, e.g. water, or a gas, e.g., air, for example, as shown in FIGS. 8B-8D, that is delivered to the second expandable member 618 through a second delivery member 616.

The second delivery member 616 is positioned in association with the inner shaft 612 and can be located inside the lumen 614 of the inner shaft 612 or can be positioned on the exterior of the inner shaft 612, depending on the particular needs or application, as long as the second delivery member 616 remains in communication with the second expandable member 618 so that a suitable material or fluid, such as a suitable liquid or gas, can be delivered into the second expandable member 618.

Similar to the first expandable member 608 and expandable members 114, 314, 414 and 514 of medical material delivery devices 100, 300, 400 and 500 respectively, the second expandable member 618 expands when a suitable fluid or material to expand the second expandable member 618, as can include an aqueous solution, e.g. water, or a gas, e.g., air, for example, fills the interior of the second expandable member 618 and can be arranged into at least three separate arrangements. The second expandable member 618 can be made of a suitable material, such as an elastic medical grade material, a plastic material or a textile material, for example, that can be deflated or inflated/expanded that can allow for the expansion of the expandable member 618, or can be made from other suitable material, such as depending upon the use or application, for example.

The second expandable member 618 can be arranged into an unexpanded arrangement 620a as shown in FIG. 6A, an expanded arrangement 620b as shown in FIG. 6C, or can be placed in other arrangements, such as a deflated arrangement, where the second expandable member 618 is in one or more partially filled states, for example. When the second expandable member 618 is placed in the expanded arrangement 620b, the second expandable member 618 can be placed into contact with the inner wall of a blood vessel, thereby preventing further withdrawal of the medical material delivery device 600 and also allowing for localization of the puncture site, for example a localization of an arteriotomy, as shown in FIGS. 8C-8D.

Figure 8E:
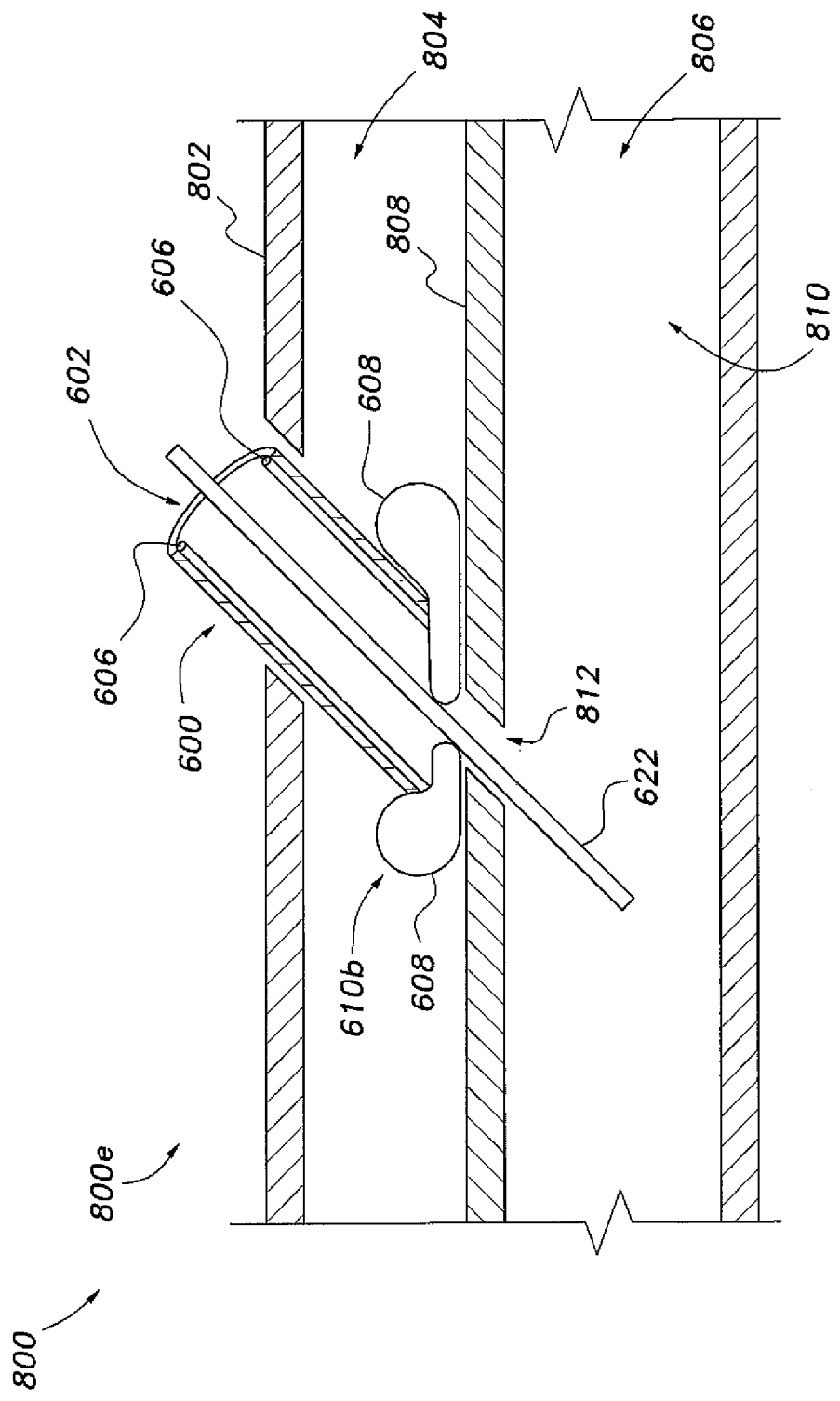
FIG. 8E is an environmental cross section of an embodiment of a fifth step of another method for sealing a puncture in a blood vessel using embodiments of a medical material delivery device according to the present invention.
Figure 8F:
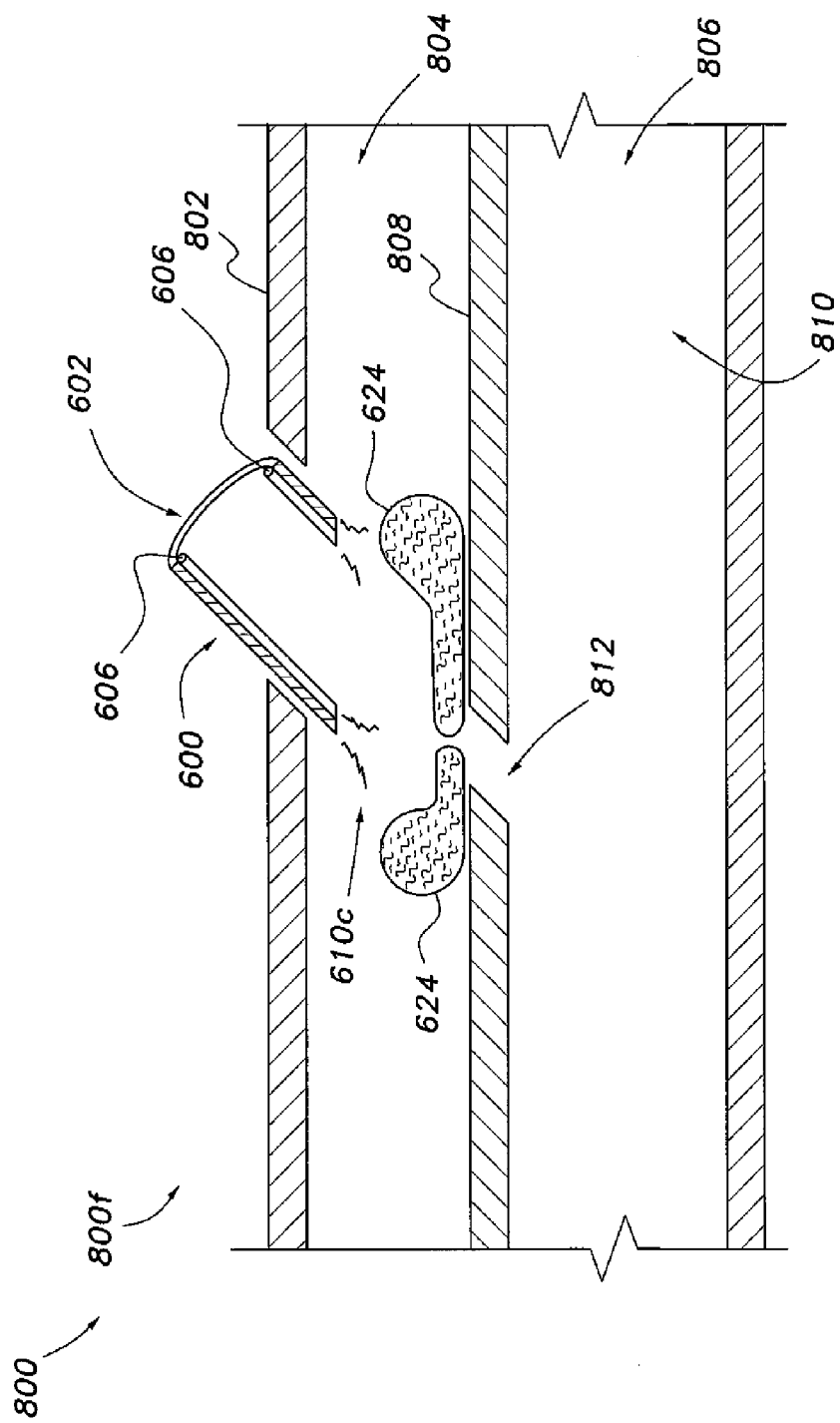
FIG. 8F is an environmental cross section of an embodiment of a sixth step of another method for sealing a puncture in a blood vessel using embodiments of a medical material delivery device according to the present invention.

The second expandable member 618 can also be arranged into a deflated arrangement. When the second expandable member 618 is in the deflated arrangement, the inner shaft 612 can be removed from the lumen 604 of the outer shaft 602, as shown in FIG. 8E. The first expandable members 114, 314, 414, 514 and 608 and the second expandable member 618 of medical material delivery devices 100, 300, 400, 500 and 600, respectively, can be any of various suitable fillable objects, such as a balloon, a bag, a sac or other hollow fillable objects and can be of various sizes and shapes, and, therefore, should not be construed in a limiting sense.

The second lumen 614 of the inner shaft 612 is adapted to receive a medical instrument 622, as shown in FIGS. 8A-8D. Further, the first lumen 604 of the outer shaft 602 is also adapted to receive the medical instrument 622 as shown in FIG. 8E or additional medical instruments, depending on the particular needs or application. The medical instrument 622 can be a guide wire, as shown in FIGS. 8A-8E, or other instruments used in invasive medical procedures, such as a trocar, a cannula, or a scalpel, among others. The expandable members 608 and 618 can be expanded together at the same time, or the first expandable member 608 can be expanded first before the expansion of the second expandable member 618, or the second expandable member 618 can be expanded before the expansion of the first expandable member 608. The order of expansion of the expandable members 608 and 618 can depend on the particular needs or application, for example.

Similar to the expandable member 114 of the medical material delivery device 100, the expandable members 314, 414, 514, and 608, of the medical material delivery devices 300, 400, 500 and 600, can be disrupted so as to at least one of burst, leak or become broken, for example, to deliver the therapeutic agent by any of various embodiments of disrupting mechanisms, such as by the various disrupting mechanisms 118a-118e provided for and illustrated in FIGS. 2A-2E, as can depend on the particular needs or application. For example, the plurality of longitudinal breakage lines 118a, the generally circumferential breakage line 118b, the string disrupting mechanism 118c, the needle disrupting mechanism 118d, and the chemical disrupting mechanism 118e can all be used as a disrupting mechanism for the expandable members 314, 414, 514, and 608, of the medical material delivery devices 300, 400, 500 and 600, and should not be construed in a limiting sense.

Regarding the materials that can be used for medical material delivery devices 100, 300, 400, 500 and 600, as stated previously, the expandable members 114, 314, 414, 514, 608 and 618 of the medical material delivery devices 100, 300, 400, 500 and 600 can be made from an elastic medical grade material or other suitable material, depending on the particular needs or application, for example. The remaining components of the medical material delivery devices 100, 300, 400, 500 and 600 can also be made from medical grade materials or other suitable materials, such as medical grade metals, plastics, or composites.

For example, the shafts 102, 302, 402, 502, 602 and 612 of the medical material delivery devices 100, 300, 400, 500 and 600 can be made from stainless steel or other suitable material. Also, for example, various components of the medical material delivery devices 100, 300, 400, 500 and 600 can be made from a medical grade memory shape material such as nitinol. The types of materials for the various components of the medical material delivery devices 100, 300, 400, 500 and 600 can be selected depending on the particular needs and application, for example, and should not be construed in a limiting sense.

Referring to FIGS. 7A-7F, an embodiment of a method 700 for sealing a puncture in a blood vessel of a patient using the medical material delivery device 100 is shown, the blood vessel being an example of a procedure involving a bodily part. A first step 700a of the method 700 involves sealing a puncture in a blood vessel during angiography through a blood vessel 706. A medical instrument 122, such as a trocar, punctures the surface of the skin 702 and goes through the skin layer 704 continuing past the surface 708 of the blood vessel 706 and into the interior 710 of the blood vessel 706.

A second step 700b of the method 700 for sealing a puncture in a blood vessel involves the placement of the medical material delivery device 100 in conjunction with the medical instrument 122. The medical material delivery device 100 is placed into position by a user manipulating the shaft 102 of the medical material delivery device 100 by either gripping by hand the shaft 102 or by gripping an attached structure such as a handle that is attached to the shaft 102. The user can place the medical material delivery device 100 in such a position so that the guide 110 is in conjunction with the blood vessel 706, as shown in FIGS. 7B-7C. The channel 112 of the guide 110 receives the medical instrument 122 that allows for the guide 110 to be placed in conjunction with the blood vessel 706 and for the expandable member 114 to be in communication with the blood vessel 706 and the surface 708 of the blood vessel 706.

Once a user has completed the angiographic study, the medical instrument 122 is removed from the patient, as shown in a third step 700c of the method 700 shown in FIG. 7C. The user can then expand the expandable member 114 as shown in a fourth step 700d of the method 700 of FIG. 7D by placing a therapeutic agent 124 in the lumen 108 of the shaft 102. As the therapeutic agent 124 travels through the lumen 108 of the shaft 102, the expandable member 114 can continue to expand, such as into the expanded arrangement 116b shown in FIG. 7D.

During a fifth step 700e of the method 700, the expandable member 114 will rupture into at least one of a burst, leak or broken arrangement, depending on the use or application, for example, to deliver the therapeutic agent, such as the burst open arrangement 116c, as shown in FIG. 7E. The expandable member 114 can rupture by any suitable disrupting mechanism 118, such as provided for and illustrated in FIGS. 2A-2E, such as the plurality of longitudinal breakage lines 118a, the generally circumferential breakage line 118b, the string disrupting mechanism 118c, the needle disrupting mechanism 118d, or the chemical disrupting mechanism 118e, for example.

When the expandable member 114 has been ruptured, the therapeutic agent 124 that was formerly contained in the expandable member 114 is now released into the patient. As shown in FIG. 7E, the therapeutic agent 124 can be positioned in relation to the blood vessel puncture site 712 that was formed when the medical instrument 122 went through the surface 708 of the blood vessel 706 and into the interior 710 of the blood vessel 706.

Figure 7F:
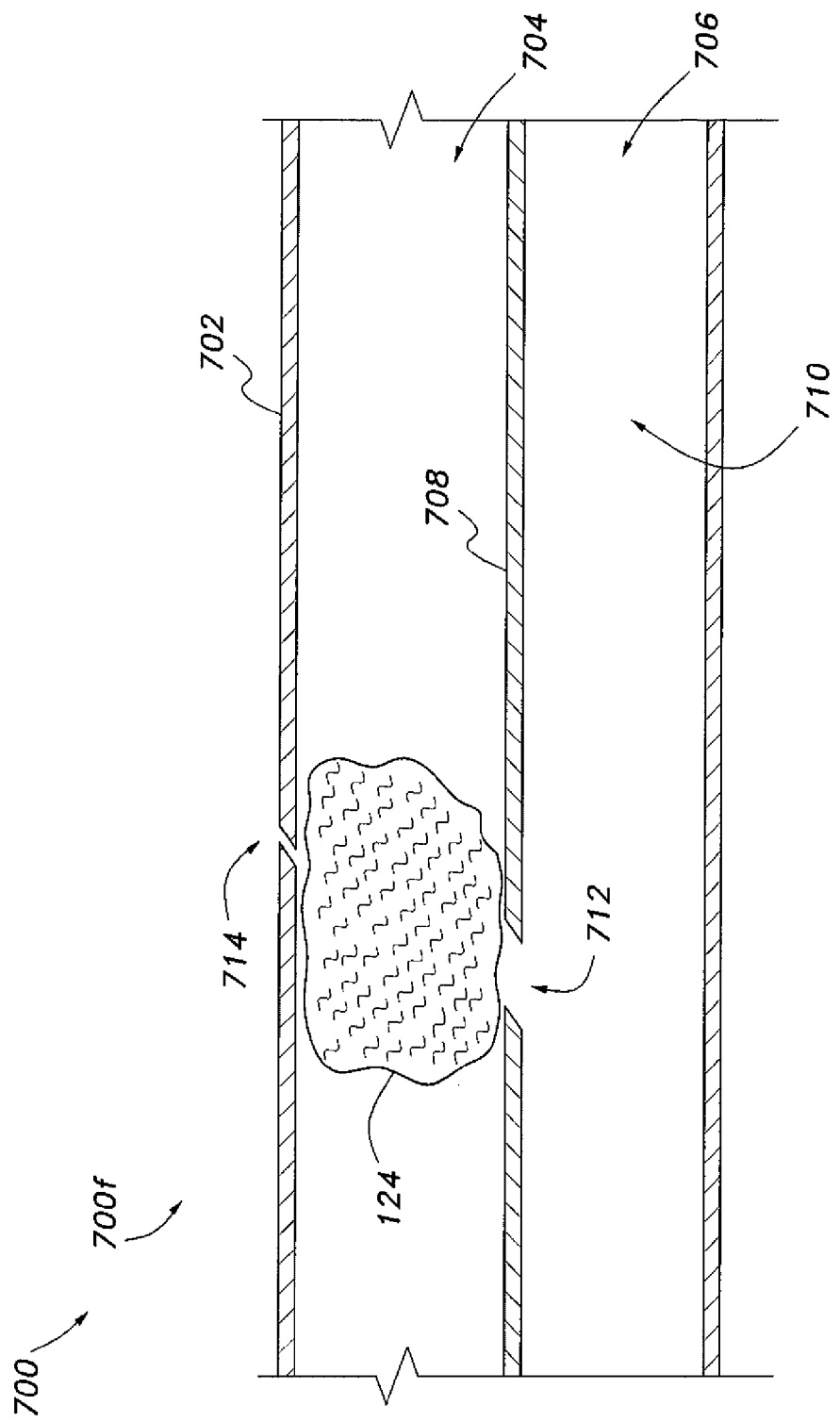
FIG. 7F is an environmental cross section of an embodiment of a sixth step of a method for sealing a puncture in a blood vessel using embodiments of a medical material delivery device according to the present invention.

The therapeutic agent 124, in the example illustrating the method 700, can be any suitable agent that can promote blood clotting, such as the patient's own clotted blood, thrombin, fibrin, a liquid embolic material, a lipid based sealing material, or any other common clotting agent, for example. A sixth step 700f of the method 700 can be to let the patient rest as the therapeutic agent 124 spreads and seals or substantially seals the blood vessel puncture site 712 and the skin puncture site 714, such as shown in FIG. 7F.

Referring to FIGS. 8A-8G, an embodiment of a method 800 for sealing a puncture in a blood vessel 806 of a patient using the medical material delivery device 600 is shown, the blood vessel being an example of a procedure involving a bodily part. A first step 800a of the method 800 as shown in FIG. 8A for sealing a puncture in a blood vessel 806 involves the placement of the medical material delivery device 600 in conjunction with a medical instrument 622. The medical instrument 622, for example a guide wire as shown in FIGS. 8A-8E, has been placed inside the patient by a user.

The medical material delivery device 600 is placed in conjunction with the medical instrument 622 so that the first expandable member 608 associated with the outer shaft 602 and the second expandable member 618 associated with the inner shaft 612 are in communication with the blood vessel 806. As shown in FIG. 8A, during a first step 800a of the method 800, the outer shaft 602 and the inner shaft 612 of the medical material delivery device 600 are placed through a surface 802 of the skin and skin layer 804, through a surface 808 of the blood vessel 806, and into an interior 810 of the blood vessel 806.

During a second step 800b of the method 800 shown in FIG. 8B, the user expands the second expandable member 618 associated with the inner shaft 612 into the expanded arrangement 620b while the second expandable member 618 is positioned in the interior 810 of the blood vessel 806 and away from the surface 808 of the blood vessel 806. The user expands the second expandable member 618 by placing a suitable material or fluid, such as a suitable liquid or gas, to expand the second expandable member 618, as can include an aqueous solution, e.g. water, or a gas, e.g., air, for example, into the second delivery member 616. The second expandable member 618 will then become inflated and be placed into the expanded arrangement 620b as shown in FIGS. 8B-8D.

Further, during a third step 800c in the method 800, the user can position the expanded arrangement 620b of the second expandable member 618 in communication with the interior 810 of the blood vessel 806 and the surface 808 of the blood vessel 806. By placing the expanded arrangement 620b of the second expandable member 618 in communication with both the interior 810 of the blood vessel 806 and the surface 808 of the blood vessel 806, the second expandable member 618 can prevent further withdrawal of the medical material delivery device 600 and can also allow for localization of the puncture site, as shown in FIGS. 8B-8D.

When the expanded arrangement 620b of the second expandable member 618 is positioned in communication with a side of the blood vessel puncture site 812, the first expandable member 608 is then placed into the expanded arrangement 610b during a fourth step 800d of the method 800 for sealing a puncture in a blood vessel as shown in FIG. 8D. The user expands the first expandable member 608 by placing a therapeutic agent 624 into the first delivery member 606. The first delivery member 606 can carry and deposit the therapeutic agent 624 into the interior of the first expandable member 608. The therapeutic agent 624, in the example illustrating the method 800, can be any suitable agent that would promote blood clotting, such as the patient's own clotted blood, thrombin, fibrin, a liquid embolic material, a lipid based sealing material, or any other common clotting agent, for example.

As shown in FIG. 8E, during a fifth step 800e of the method 800, the second expandable member 618 is deflated and is no longer in the expanded position 620b. When the second expandable member 618 is in the deflated arrangement, the inner shaft 612 including the second expandable member 618 can be removed from the blood vessel 806 by the user, as shown in FIG. 8E. The user can remove the inner shaft 612 while the medical instrument 622 and the outer shaft 602 including the first expandable member 608 remain positioned in conjunction with the blood vessel 806.

Figure 8G:
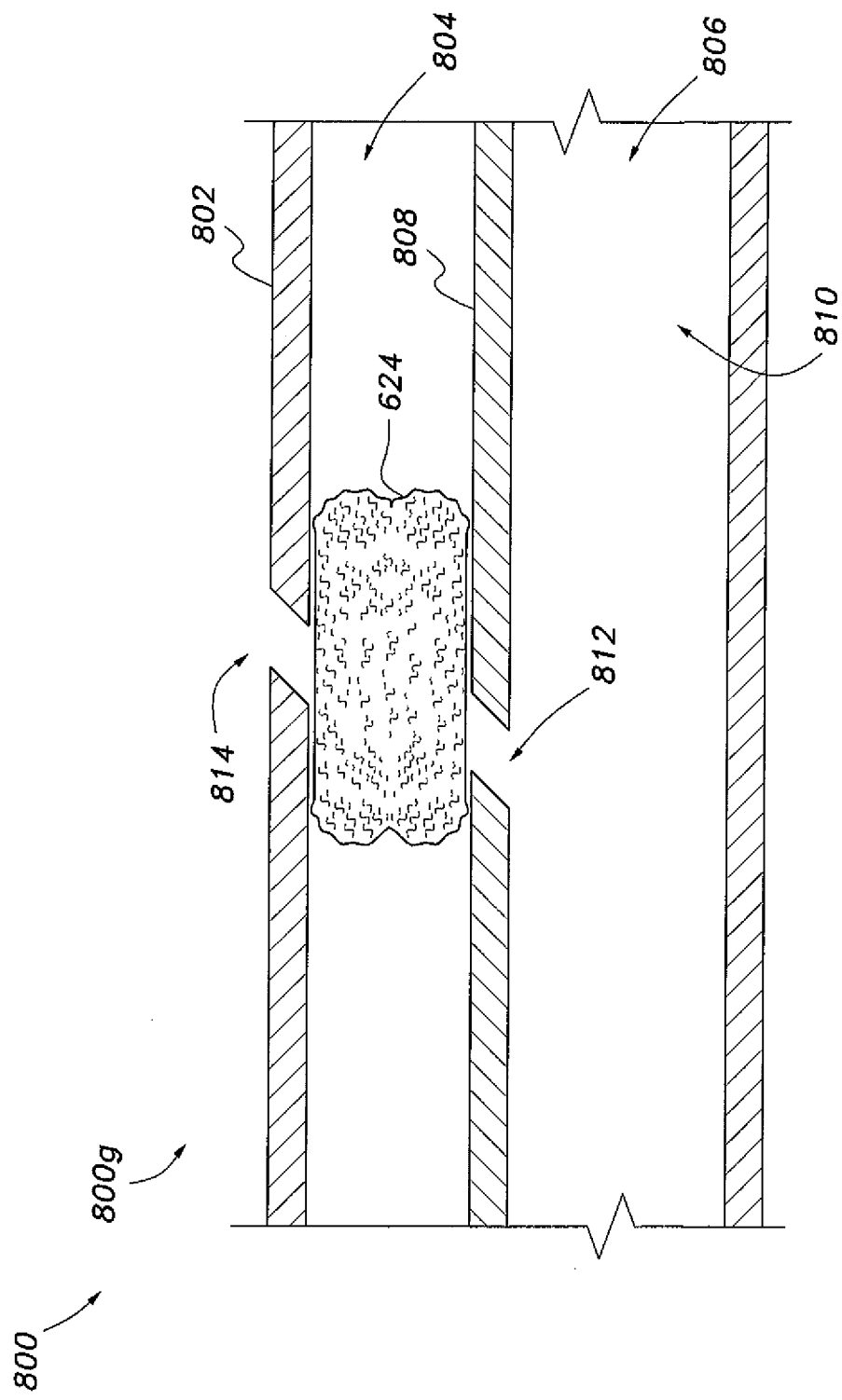
FIG. 8G is an environmental cross section of an embodiment of an seventh step of another method for sealing a puncture in a blood vessel using embodiments of a medical material delivery device according to the present invention.

During a sixth step 800f of the method 800 shown in FIG. 8F, the user can place the first expandable member 608 into the burst open arrangement 610c. When the first expandable member 608 is in the burst open arrangement 610c, the therapeutic agent 624 that was contained within the first expandable member 608 is delivered to the surface 808 of the blood vessel 806. A seventh step 800g of the method 800 as shown in FIG. 8G has the user remove the outer shaft 602 from the patient. The patient can rest as the therapeutic agent 624 spreads and seals or substantially seals a side of the blood vessel puncture site 812 and the skin puncture site 814.

As provided in the methods 700 and 800, the medical material delivery device 100 and the medical delivery device 600, for example, can be used to seal a puncture in a blood vessel. Medical material delivery device 100, and the remaining medical material delivery devices 300, 400, 500 and 600, which can be used to seal a puncture in a blood vessel, can also be used for other medical procedures that involve the delivery of various therapeutic agents, to a bodily part, such various therapeutic agents as can include water, a saline solution or contrast agents, for example.

For example, medical material delivery devices 100, 300, 400, 500 and 600 can be used for occlusion of fistulas, sealing bodily leaks, isolation of body compartments, occlusion of patent ductus arteriosis, occlusion of atrial septal defects, occlusion of ventricular septal defects, performing vertebroplasty, performing kyphoplasty, embolization, delivery of a radiotherapy agent, delivery of a chemotherapeutic agent, delivery of other therapeutic agents, delivery of a diagnostic agent, hernia repair, and aneurysm embolization, among other procedures, as can involve bodily parts, and should not be construed in a limiting sense.

Figure 9A:
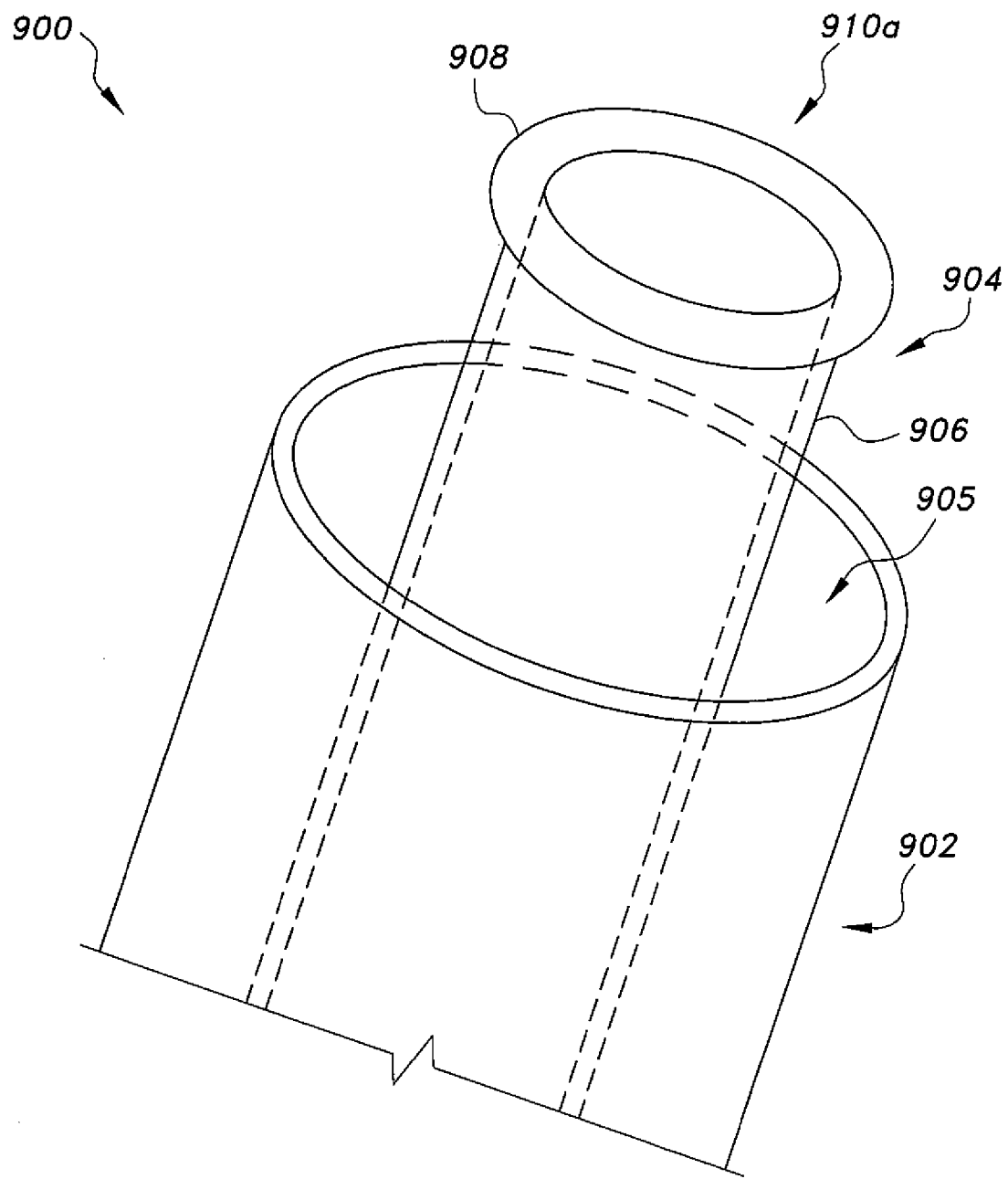
FIG. 9A is a sectional view of an embodiment of a medical material delivery device having a catheter with an expandable member positioned within an outer shaft according to the present invention.
Figure 9B:
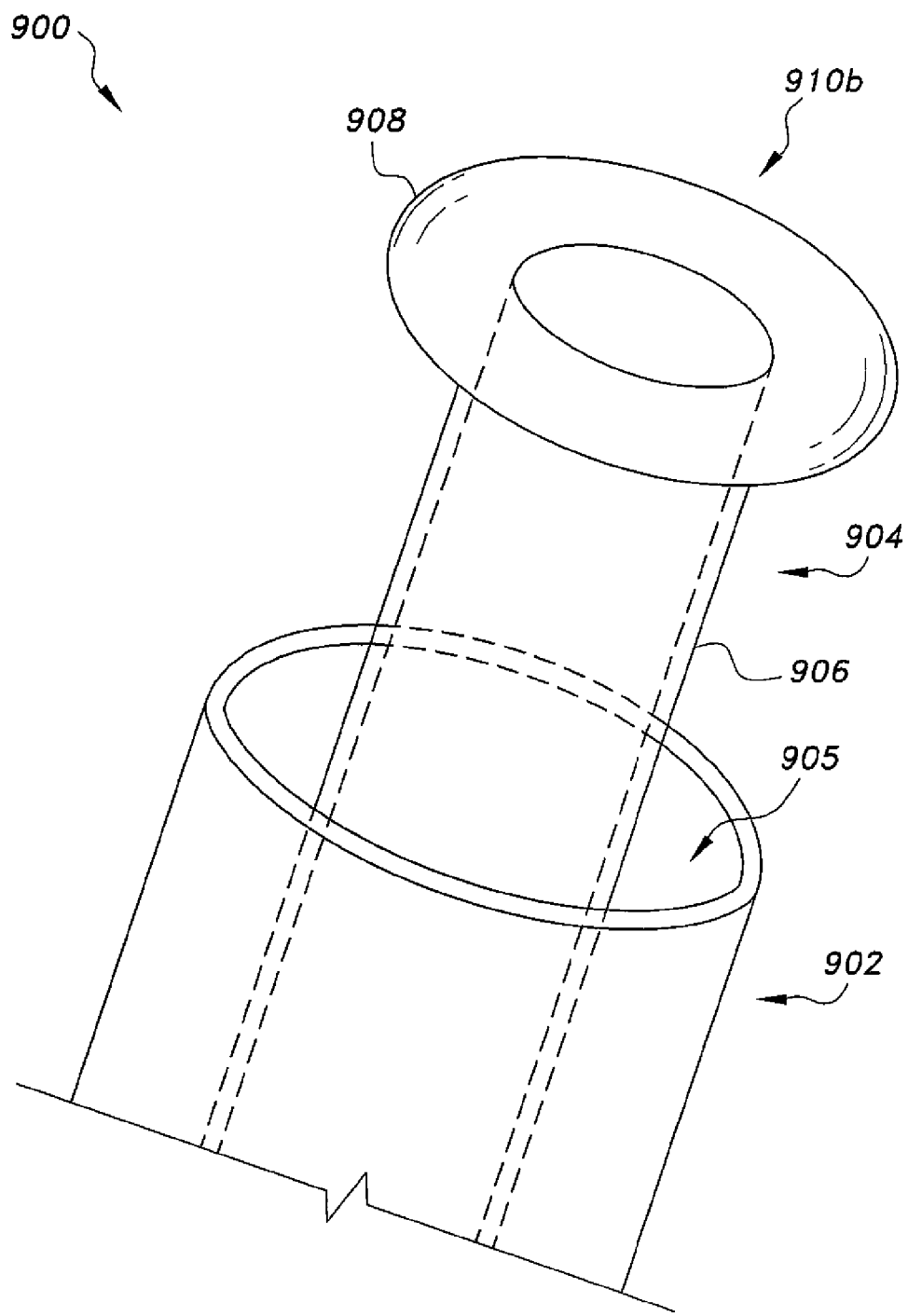
FIG. 9B is a sectional view of an embodiment of a medical material delivery device having a catheter with an inflated expandable member positioned within an outer shaft according to the present invention.

Referring to FIGS. 9A-9B, an embodiment of a medical material delivery device 900 is shown. The medical material delivery device 900 includes a shaft 902 having a lumen 905 with a catheter 904 positioned within the lumen 905 of the shaft 902. The catheter 904 includes an expandable member 908, similar to expandable members 114, 314, 414, 514, 608, and 618 of the medical material delivery devices 100, 300, 400, 500 and 600, and the expandable member 908 can be of various shapes and sizes, such as a sphere, sphere like, teardrop like or ring like shape, for example.

The expandable member 908 can be made of similar suitable materials, such as an elastic medical grade material, a plastic material or a textile material, or can be made from other suitable material, for example, that can be deflated, inflated/expanded and, when appropriate, disrupted, such as by being burst, such as depending upon the use or application, for example. The expandable member 908 can be filled with a therapeutic agent, such as therapeutic agent 124. The expandable member 908 can be filled with the therapeutic agent by a delivery member 906 that is in communication with the expandable member 908. Further, the expandable member can be placed into various arrangements, such as an unexpanded arrangement 910a, an expanded arrangement 910b, and a burst open arrangement 910c, for example.

The expandable member 908 can be placed into the at least one of a burst, leak or broken arrangement, depending on the use or application, for example, such as the burst open arrangement 910c, by being disrupted by a disrupting mechanism in which the therapeutic agent positioned within the expandable member 908 can be deposited near an appropriate bodily part, such as a blood vessel puncture site, for example.

The expandable member 908 can be disrupted by any of various embodiments of disrupting mechanisms, such as by the various disrupting mechanisms 118a-118e provided for and illustrated in FIGS. 2A-2E, as can depend on the particular needs or application. For example, the plurality of longitudinal breakage lines 118a, the generally circumferential breakage line 118b, the string disrupting mechanism 118c, the needle disrupting mechanism 118d, and the chemical disrupting mechanism 118e can all be used as a disrupting mechanism.

Figure 10B:
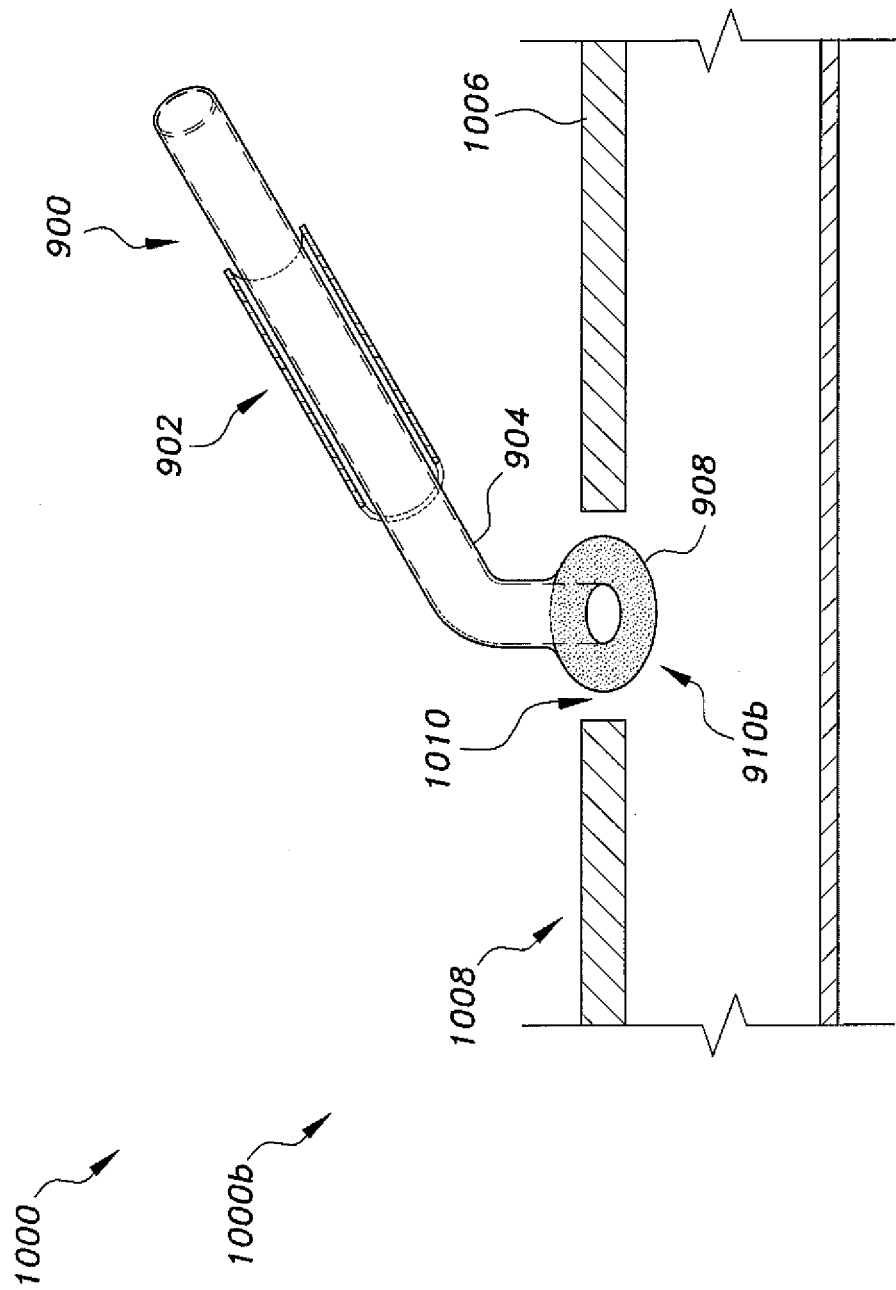
FIG. 10B is an environmental view of an embodiment of a second step of a method for correcting a fistula in a blood vessel using the embodiments of the medical material delivery device of FIGS. 9A-9B according to the present invention.
Figure 10C:
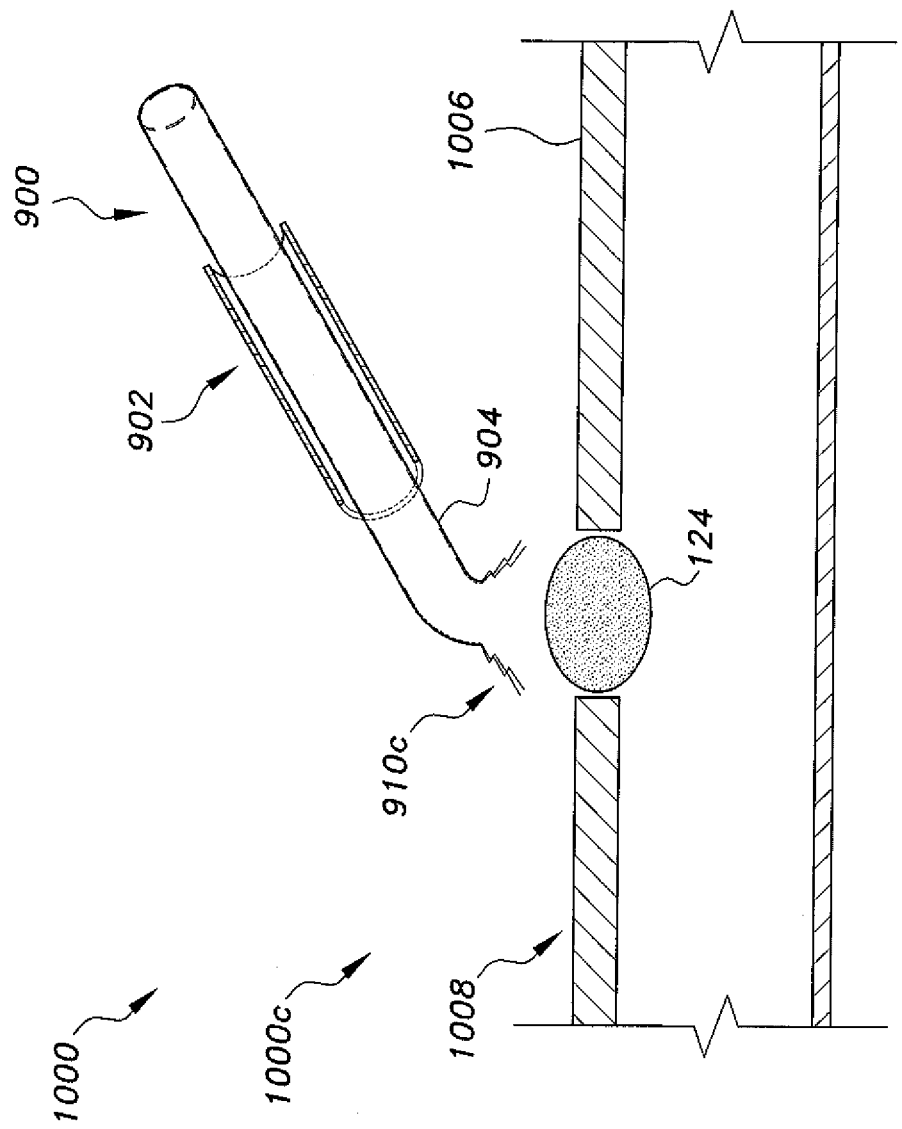
FIG. 10C is an environmental view of an embodiment of a third step of a method for correcting a fistula in a blood vessel using the embodiments of the medical material delivery device of FIGS. 9A-9B according to the present invention.

Referring to FIGS. 10A, 10B, and 10C, a method of sealing a fistula 1000 is shown using medical material delivery device 900. A first step 1000a of the method 1000, shown in FIG. 10A, includes the medical material delivery device 900 being placed in with an exterior surface 1008 of a blood vessel 1006 so that the medical material delivery device 900 is in communication with a fistula 1010 of the blood vessel 1006.

During the first step 1000a of the method 1000 the expandable member 908 of the medical material delivery device 900 remains in the unexpanded arrangement 910a during the first step 1000a. A second step 1000b of the method 1000 involves the placement of the expandable member 908 from the unexpanded arrangement 910a into the expanded arrangement 910b, as shown in FIG. 10B. As mentioned previously, the expandable member 908 can be placed into the expanded arrangement 910b by filling the expandable member 908 with a therapeutic agent 124 through the delivery member 906 of the catheter 904.

A third step 1000c of the method 1000 involves the expandable member 908 of the medical material delivery device 900 being placed from the expanded arrangement 910b into the burst open arrangement 910c, as shown in FIG. 10C. By placing the expandable member 908 into the burst open arrangement 910c, the therapeutic agent contained within the expandable member 908, such as the therapeutic agent 124, can treat the fistula 1010 of the blood vessel 1006.

Figure 11B:
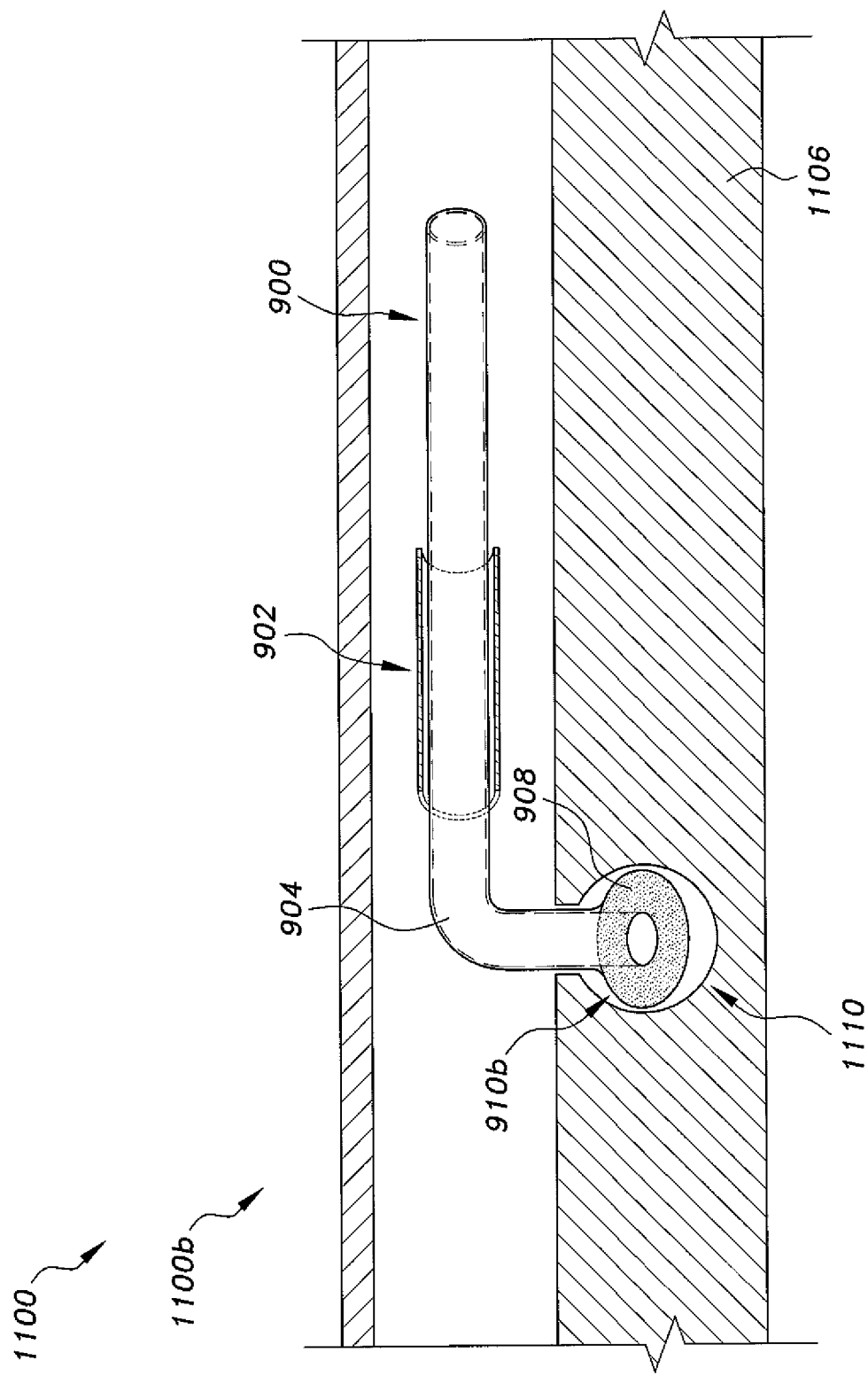
FIG. 11B is an environmental cross section view of an embodiment of a second step of a method for correcting an aneurysm using the embodiments of the medical material delivery device of FIGS. 9A-9B according to the present invention.
Figure 11C:
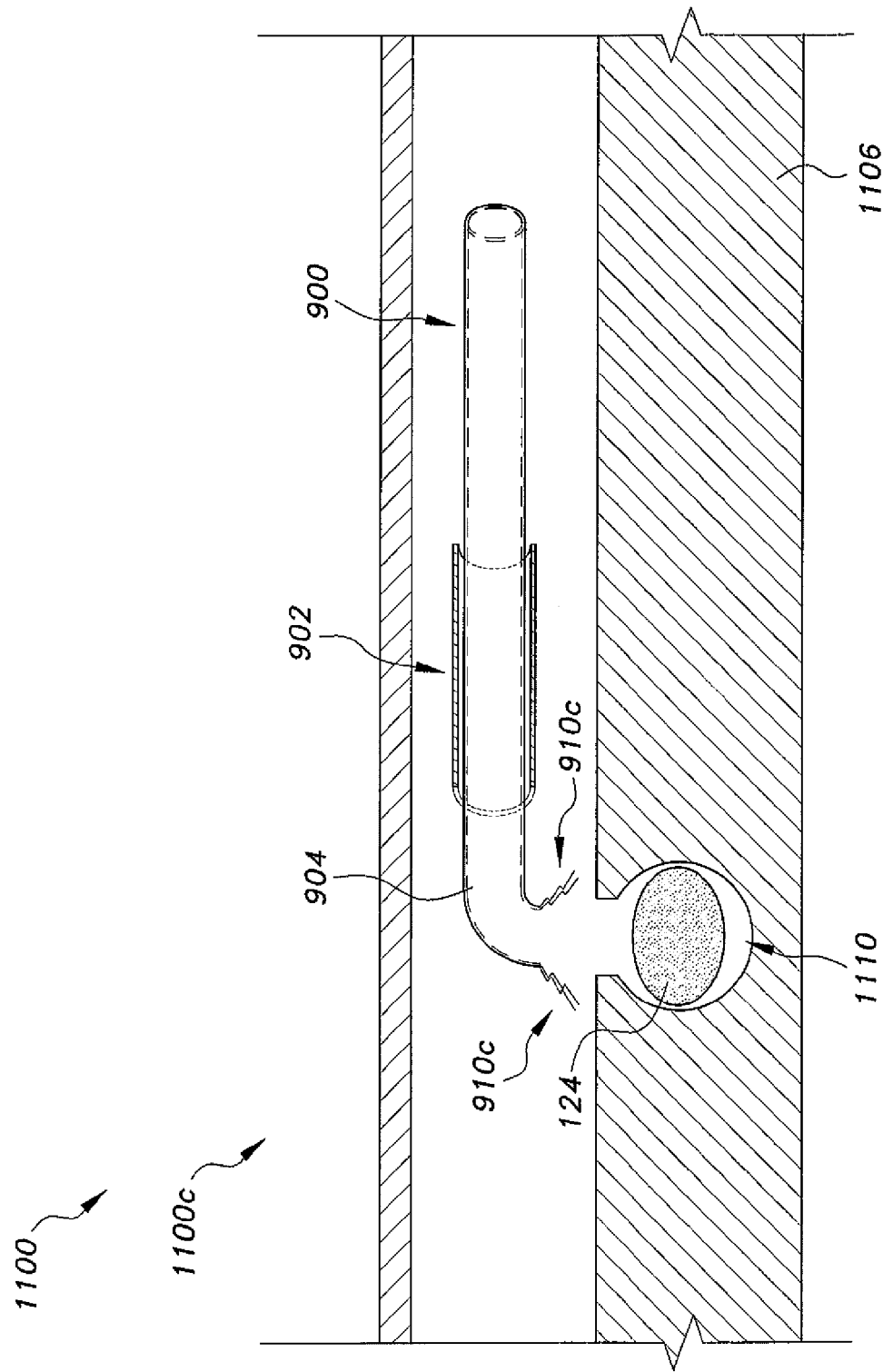
FIG. 11C is an environmental cross section view of an embodiment of a third step of a method for correcting an aneurysm using the embodiments of the medical material delivery device of FIGS. 9A-9B according to the present invention.

Referring to FIGS. 11A, 11B, and 11C, a method of embolizing an aneurysm 1100 using the medical material delivery device 900 is shown. A first step 1100a of the method 1100 is placing the medical material delivery device 900 in conjunction with an aneurysm 1110 of the blood vessel 1106. As shown in FIG. 11A, the expandable member 908 of the medical material delivery device 900 remains in the unexpanded arrangement 910a during the first step 1100a.

A second step 1100b of the method 1100 involves the placement of the expandable member 908 from the unexpanded arrangement 910a into the expanded arrangement 910b, as shown in FIG. 11B. A third step 1100c of the method 1100 involves the expandable member 908 of the medical material delivery device 900 being placed from the expanded arrangement 910b into the burst open arrangement 910c, as shown in FIG. 11C. By placing the expandable member 908 into the burst open arrangement 910c, the therapeutic agent contained within the expandable member 908, such as the therapeutic agent 124, can embolize the aneurysm 1110 of the blood vessel 1106.

Figure 12A:
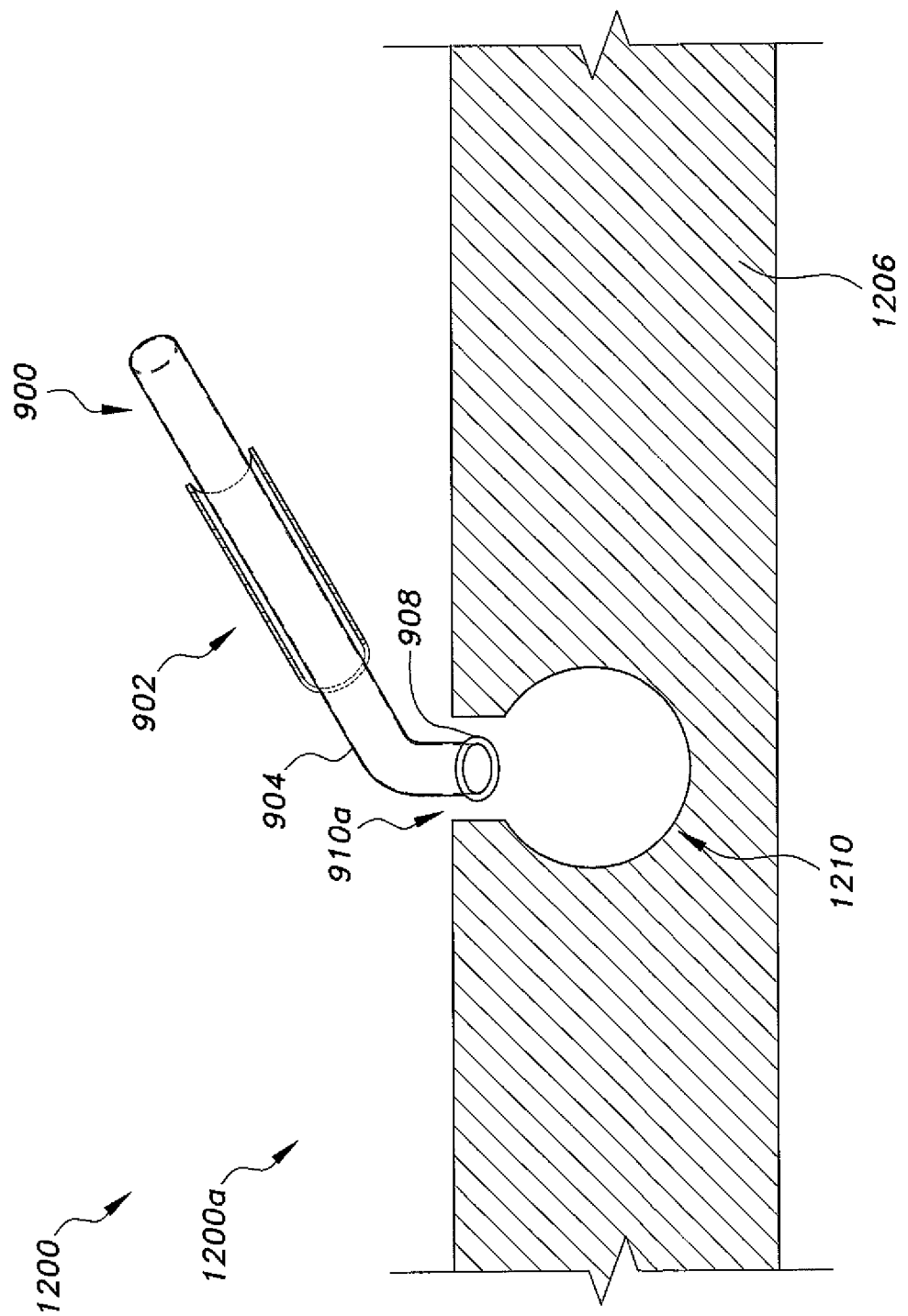
FIG. 12A is an environmental cross section view of an embodiment of a first step of a method for correcting a hernia using the embodiments of the medical material delivery device of FIGS. 9A-9B according to the present invention.
Figure 12B:
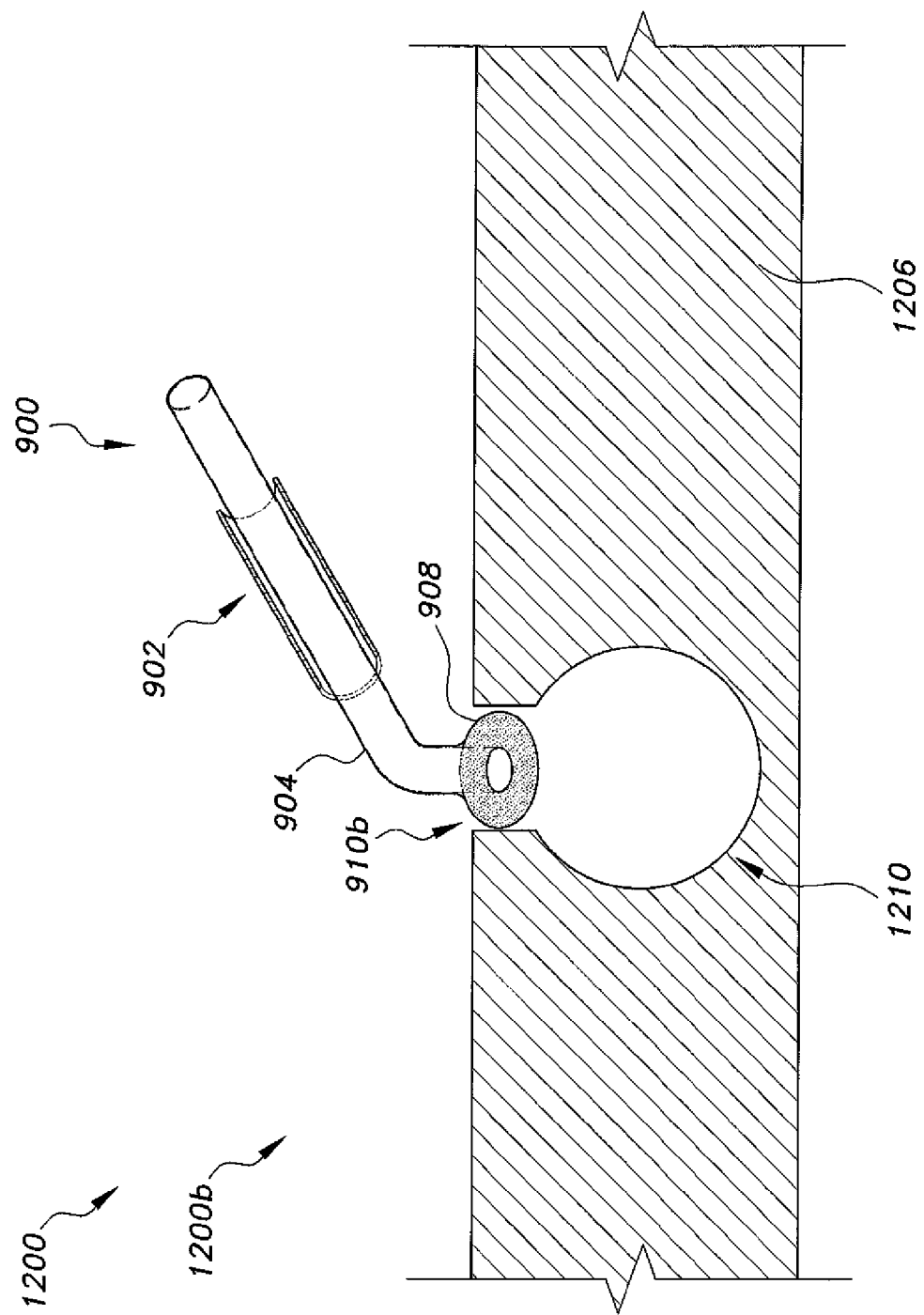
FIG. 12B is an environmental cross section view of an embodiment of a second step of a method for correcting a hernia using the embodiments of the medical material delivery device of FIGS. 9A-9B according to the present invention.

Referring to FIGS. 12A, 12B, and 12C, a method of repairing a hernia 1200 using the medical material delivery device 900 is shown. A first step 1200a of the method 1200 is placing the medical material delivery device 900 in conjunction with a hernia 1210 of a tissue 1206. As shown in FIG. 12A, the expandable member 908 of the medical material delivery device 900 remains in the unexpanded arrangement 910a during the first step 1200a.

A second step 1200b of the method 1200 involves the placement of the expandable member 908 from the unexpanded arrangement 910a into the expanded arrangement 910b, as shown in FIG. 12B. A third step 1200c of the method 1200 involves the expandable member 908 of the medical material delivery device 900 being placed from the expanded arrangement 910b into the burst open arrangement 910c, as shown in FIG. 12C. By placing the expandable member 908 into the burst open arrangement 910c, the therapeutic agent contained within the expandable member 908, such as the therapeutic agent 124, can repair the hernia 1210 of the tissue 1206.

Figure 13A:
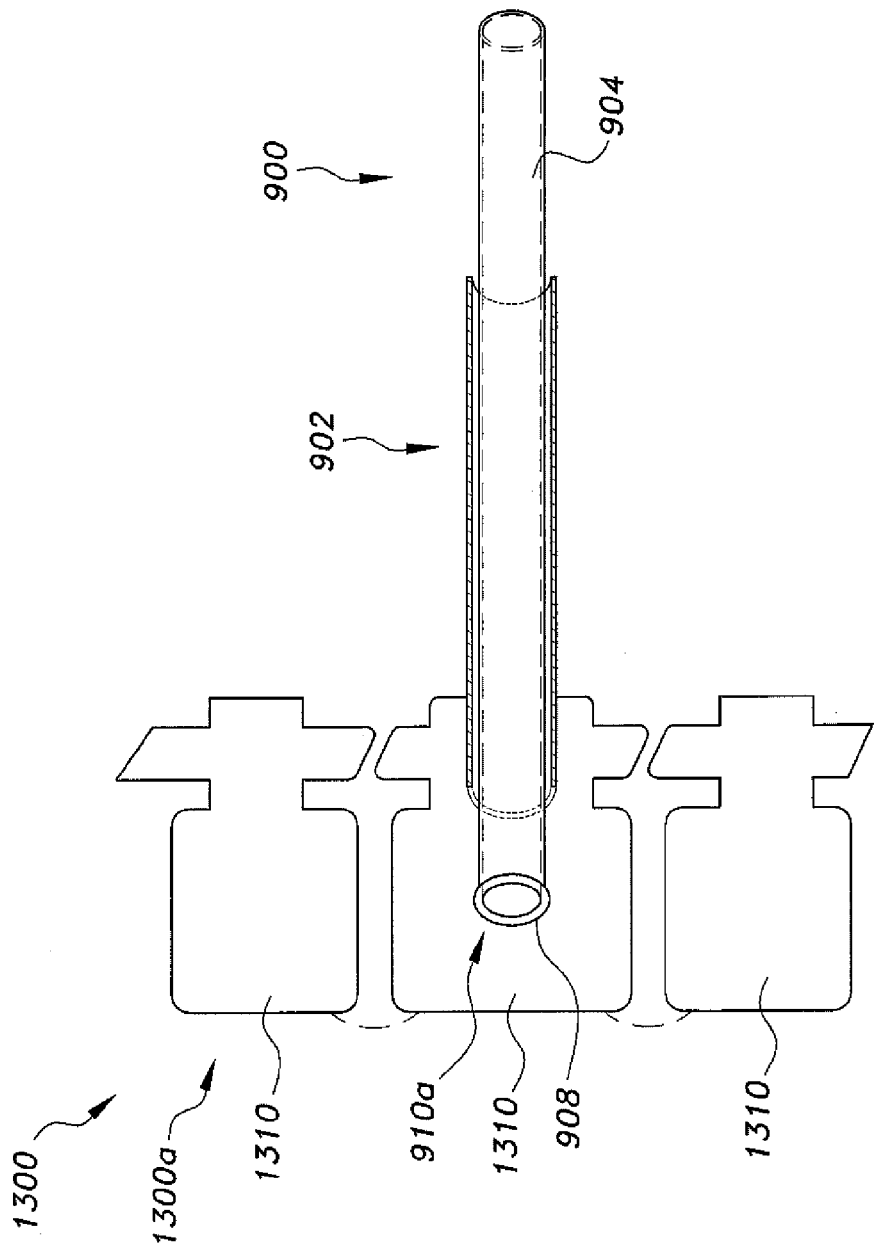
FIG. 13A is an environmental cross section view of an embodiment of a first step of a method for performing a vertebroplasty or a kyphoplasty using the embodiments of the medical material delivery device of FIGS. 9A-9B according to the present invention.
Figure 13B:
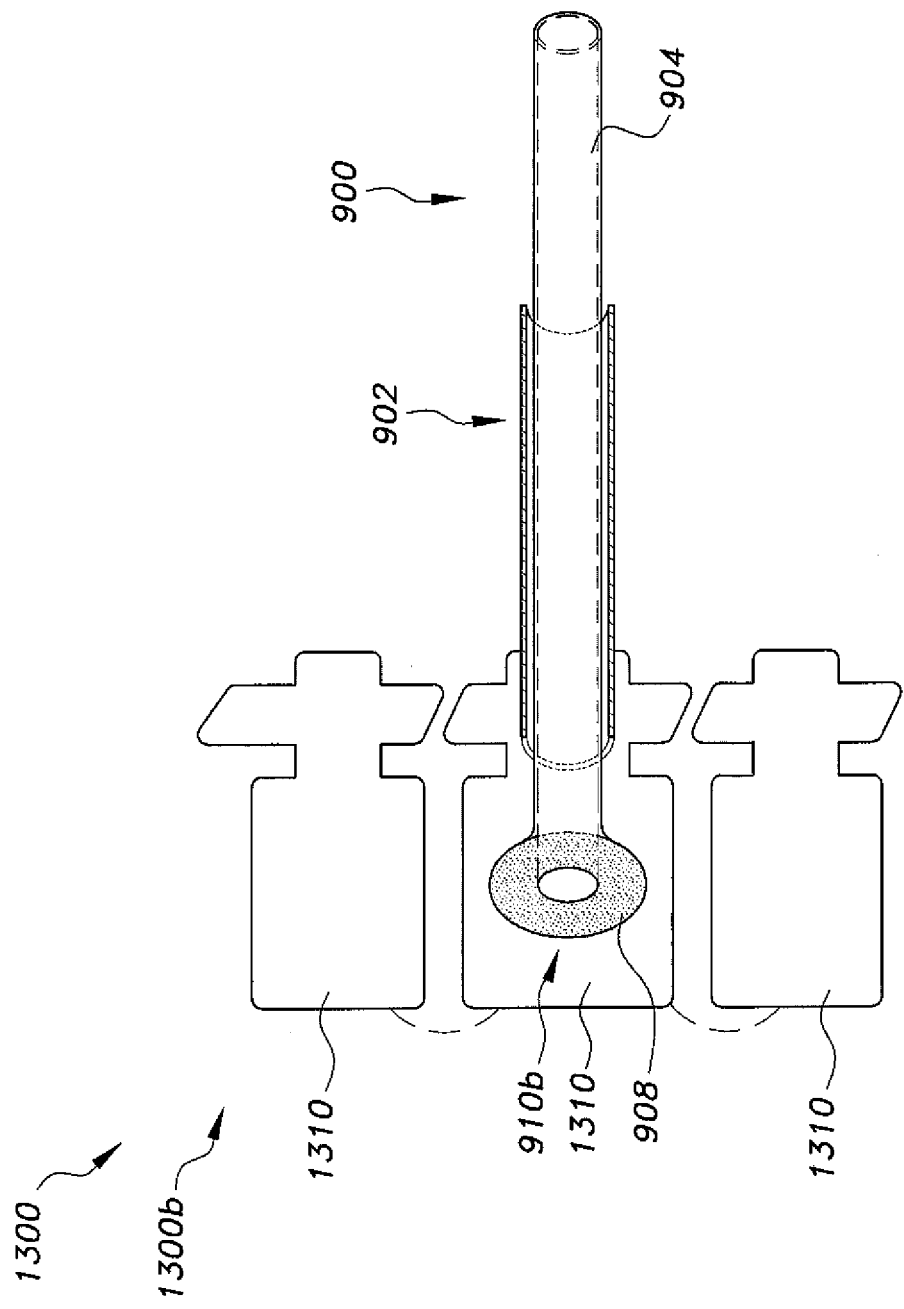
FIG. 13B is an environmental cross section view of an embodiment of a second step of a method for performing a vertebroplasty or a kyphoplasty using the embodiments of the medical material delivery device of FIGS. 9A-9B according to the present invention.
Figure 13C:
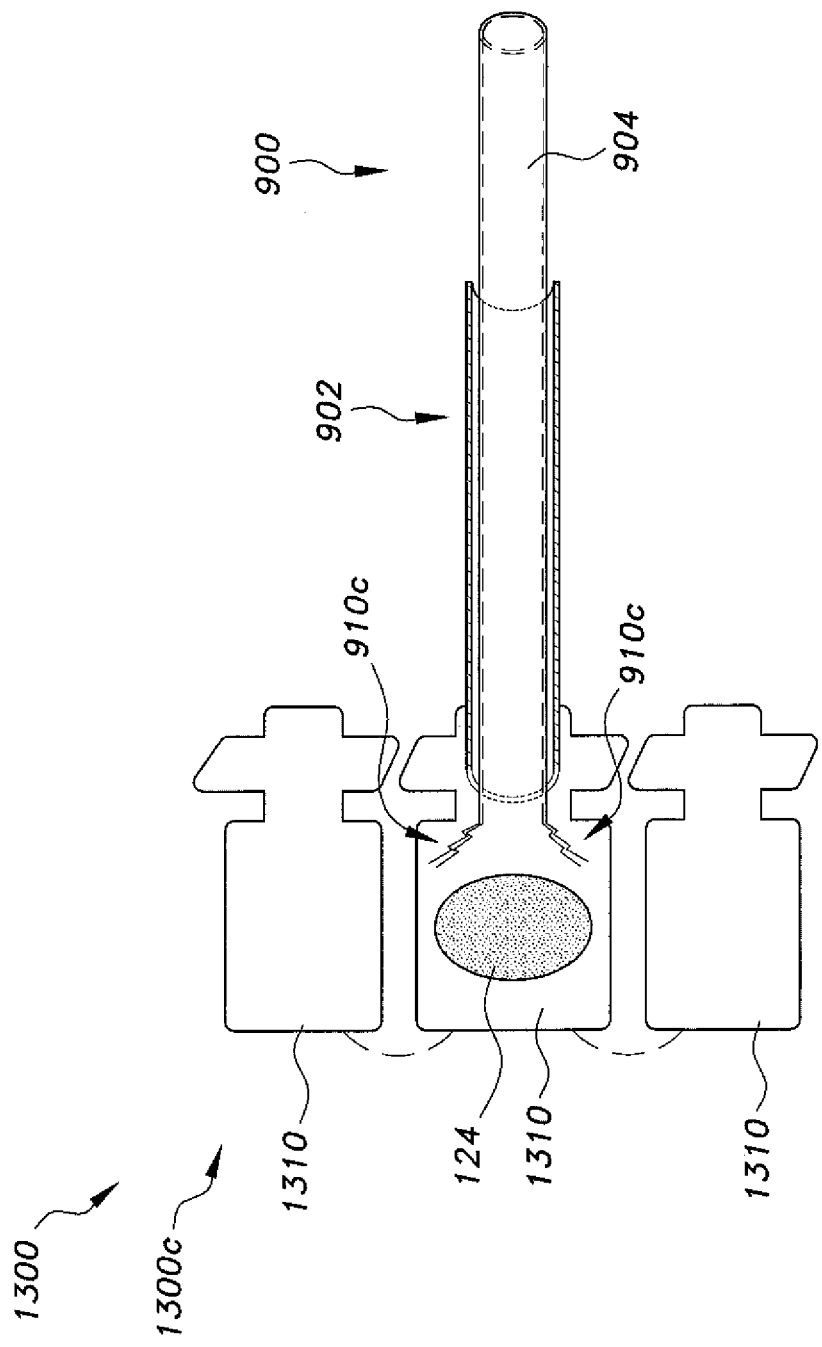
FIG. 13C is an environmental cross section view of an embodiment of a third step of a method for performing a vertebroplasty or a kyphoplasty using the embodiments of the medical material delivery device of FIGS. 9A-9B according to the present invention.

Referring to FIGS. 13A, 13B, and 13C, a method of performing a vertebroplasty or a kyphoplasty 1300 using the medical material delivery device 900 is shown. A first step 1300a of the method 1300 is placing the medical material delivery device 900 in conjunction with a vertebral body 1310. As shown in FIG. 13A, the expandable member 908 of the medical material delivery device 900 remains in the unexpanded arrangement 910a during the first step 1300a. A second step 1300b of the method 1300 involves the placement of the expandable member 908 from the unexpanded arrangement 910a into the expanded arrangement 910b, as shown in FIG. 13B.

A third step 1300c of the method 1300 involves the expandable member 908 of the medical material delivery device 900 being placed from the expanded arrangement 910b into the burst open arrangement 910c, as shown in FIG. 13C. By placing the expandable member 908 into the burst open arrangement 910c, the therapeutic agent contained within the expandable member 908, such as the therapeutic agent 124, can repair the vertebral body 1310. The therapeutic agent 124 can be a number of therapeutic agents commonly used in vertebroplasty or kyphoplasty procedures, such as bone cement.

Figure 14A:
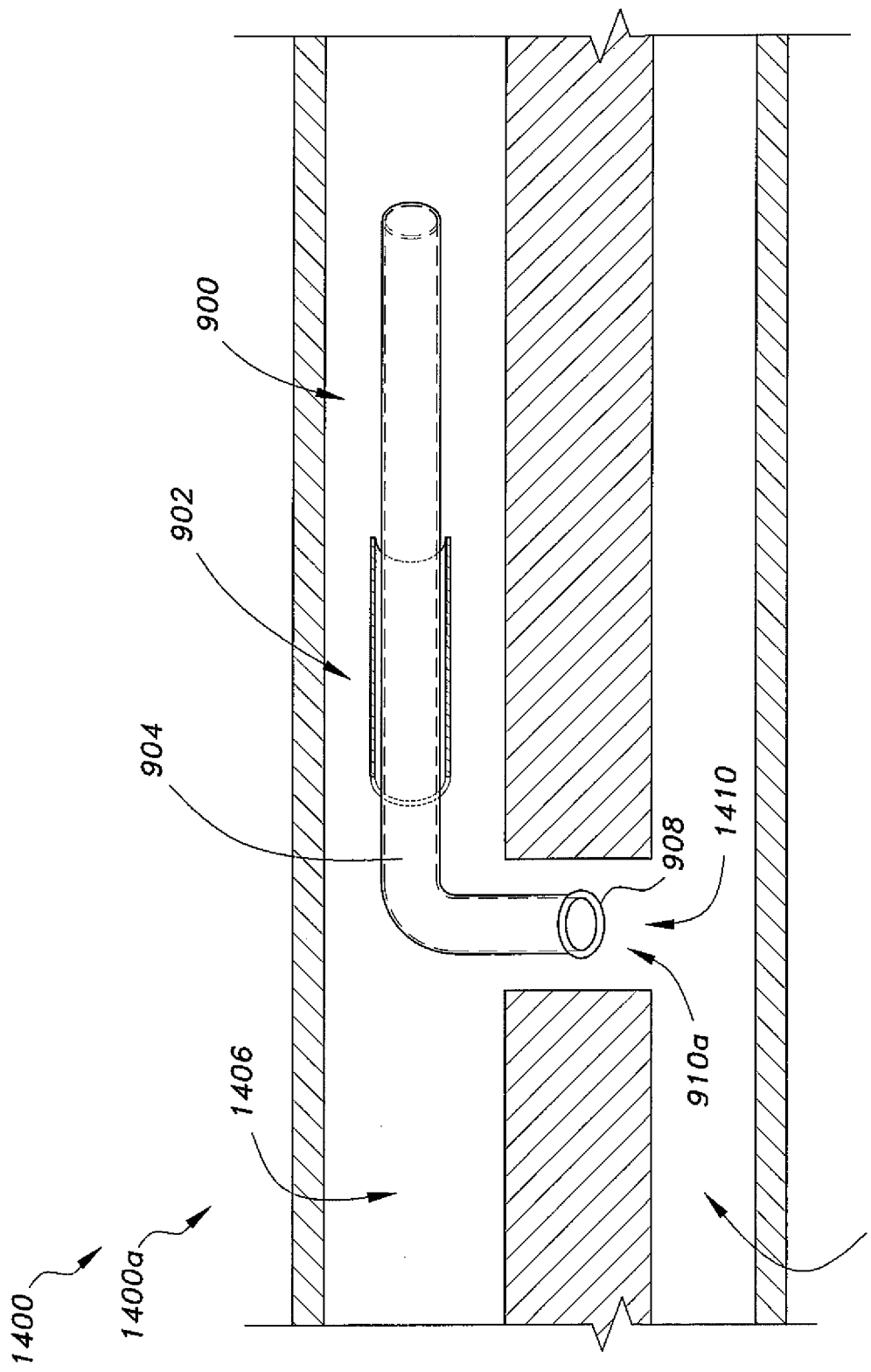
FIG. 14A is an environmental cross section view of an embodiment of a first step of a method for correcting a patent ductus arteriosus using the embodiments of the medical material delivery device of FIGS. 9A-9B according to the present invention.
Figure 14B:
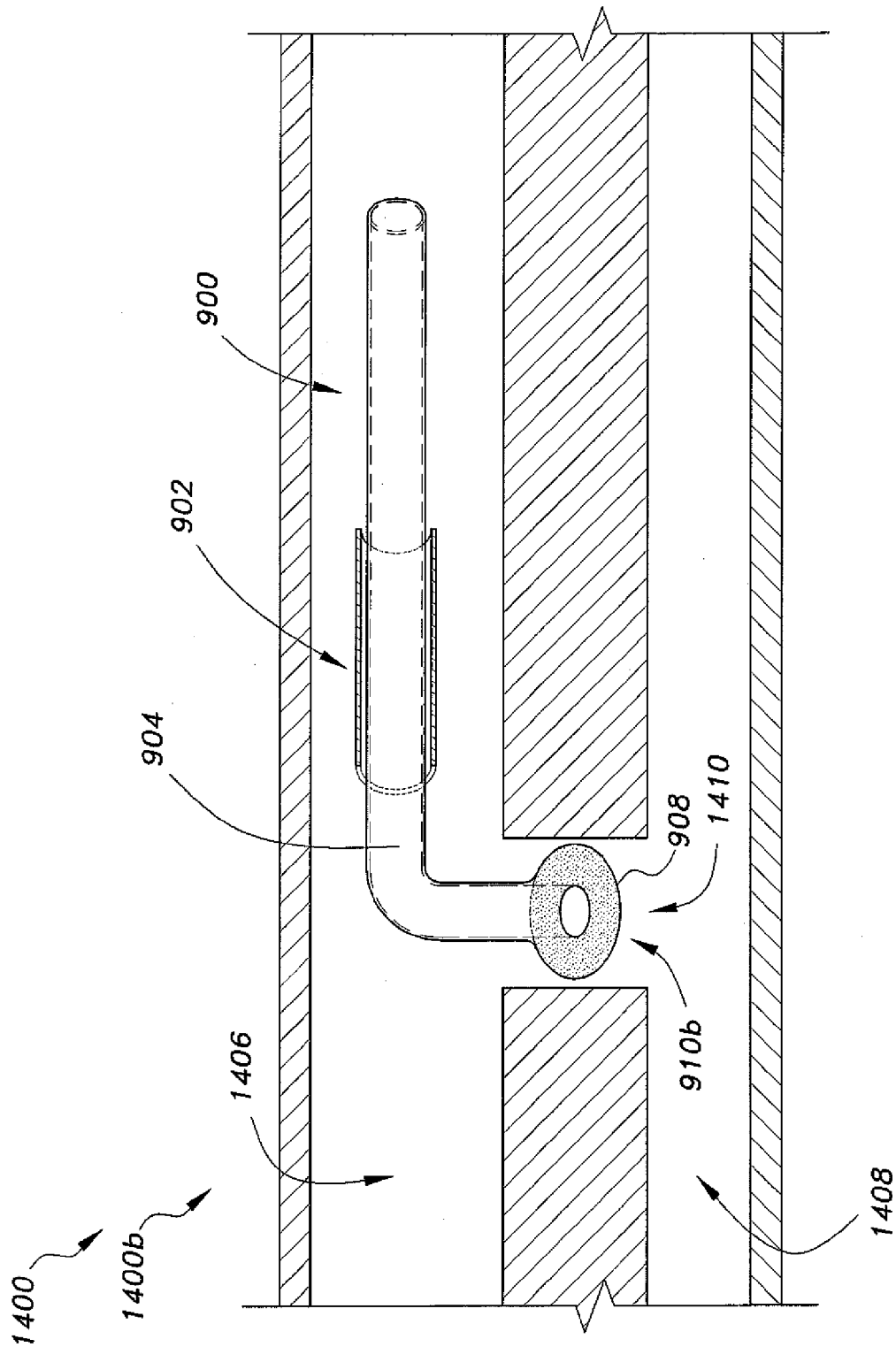
FIG. 14B is an environmental cross section view of an embodiment of a second step of a method for correcting a patent ductus arteriosus using the embodiments of the medical material delivery device of FIGS. 9A-9B according to the present invention.
Figure 14C:
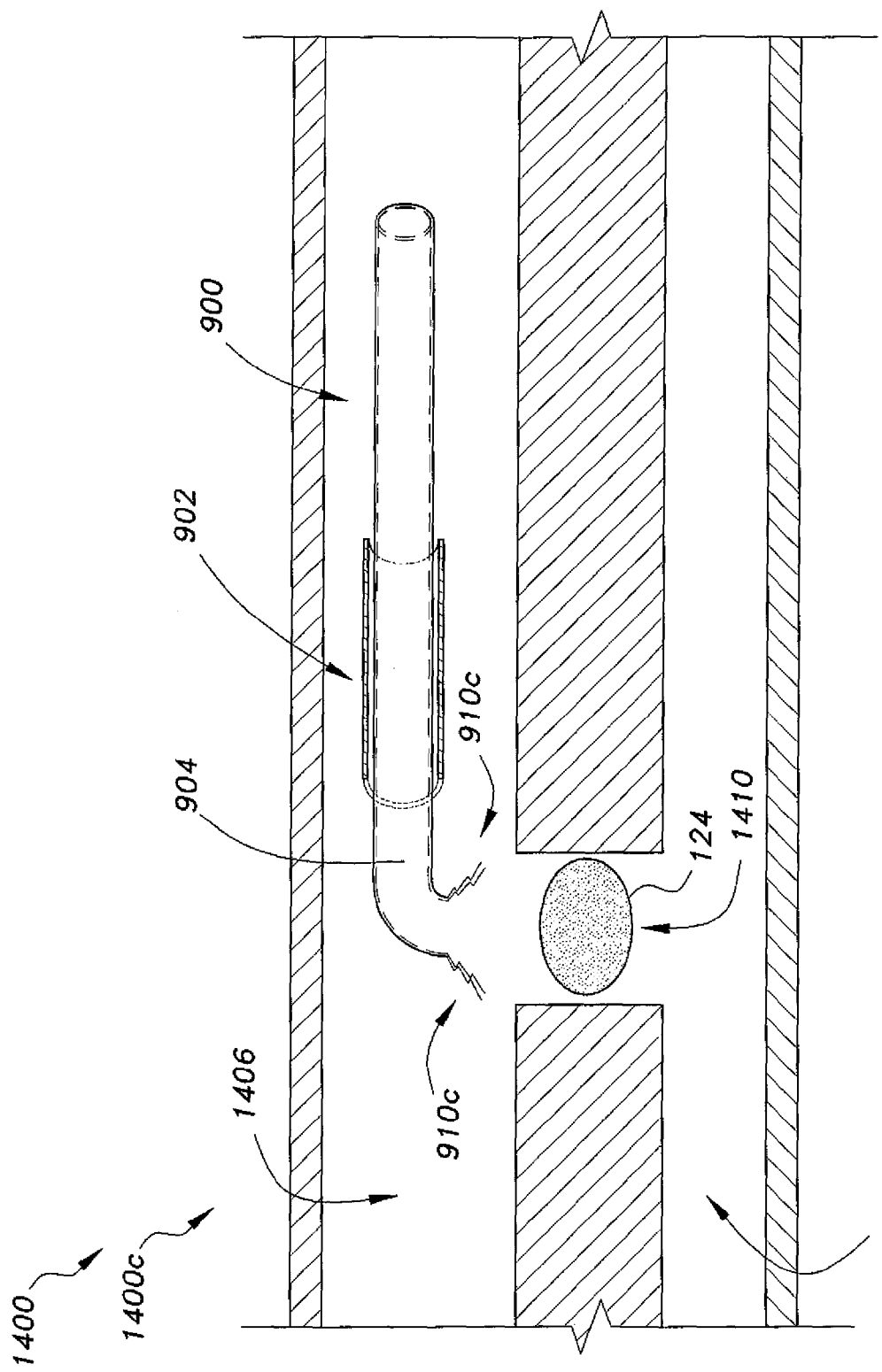
FIG. 14C is an environmental cross section view of an embodiment of a third step of a method for correcting a patent ductus arteriosus using the embodiments of the medical material delivery device of FIGS. 9A-9B according to the present invention.

Referring to FIGS. 14A, 14B, and 14C, a method of treating a patent ductus arteriosus 1400 using the medical material delivery device 900 is shown. A first step 1400a of the method 1400 is placing the medical material delivery device 900 in conjunction with a patent ductus arteriosus 1410 by placing the medical material delivery device in an aorta 1406 to be in communication with a pulmonary artery 1408 through the patent ductus arteriosus 1410. As shown in FIG. 14A, the expandable member 908 of the medical material delivery device 900 remains in the unexpanded arrangement 910a during the first step 1400a.

A second step 1400b of the method 1400 involves the placement of the expandable member 908 from the unexpanded arrangement 910a into the expanded arrangement 910b, as shown in FIG. 14B. A third step 1400c of the method 1400 involves the expandable member 908 of the medical material delivery device 900 being placed from the expanded arrangement 910b into the burst open arrangement 910c, as shown in FIG. 14C. By placing the expandable member 908 into the burst open arrangement 910c, the therapeutic agent contained within the expandable member 908, such as the therapeutic agent 124, can repair the patent ductus arteriosus 1410.

Figure 15A:
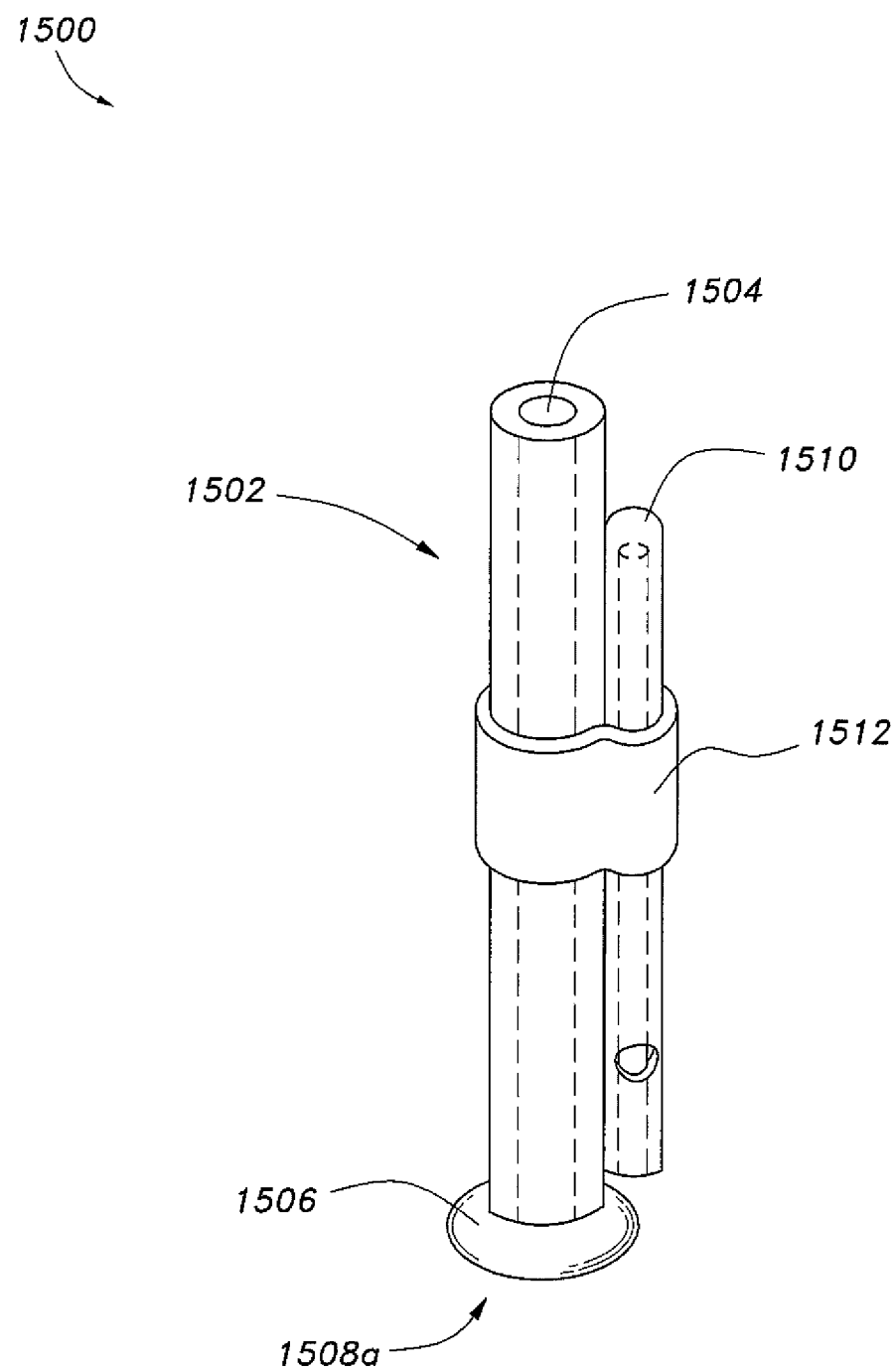
FIG. 15A is a perspective view of an embodiment of a medical material delivery device having a catheter with an expandable member and a bodily fluid locator according to the present invention.
Figure 15B:
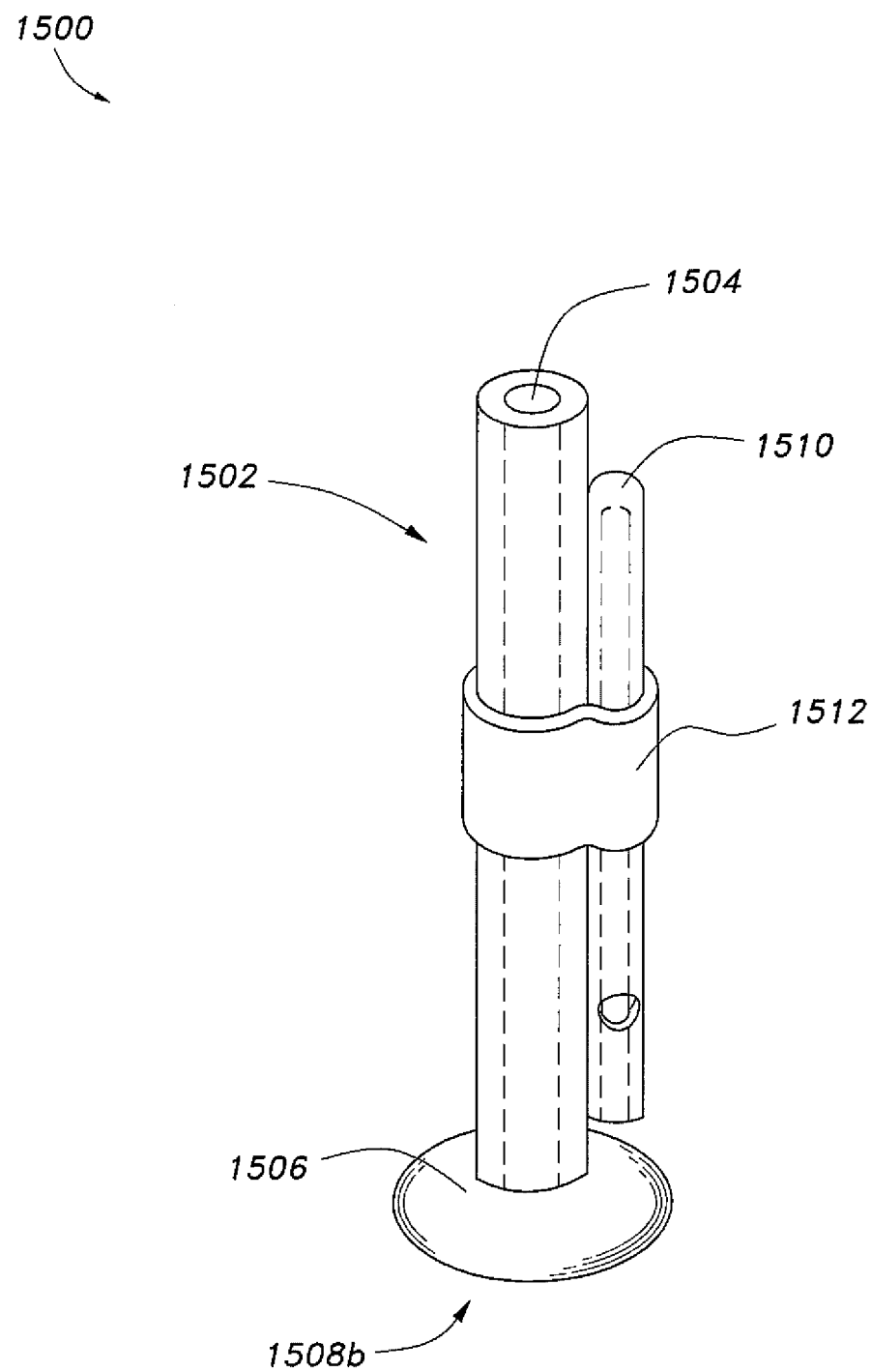
FIG. 15B is a perspective view of an embodiment of a medical material delivery device having a catheter with an inflated expandable member and a bodily fluid locator according to the present invention.

Referring to FIGS. 15A and 15B, an embodiment of a medical material delivery device 1500 is shown. The medical material delivery device 1500 includes a catheter 1502 having a lumen 1504. The catheter 1502 includes an expandable member 1506, similar to expandable members 114, 314, 414, 514, 608, and 618 of the medical material delivery devices 100, 300, 400, 500 and 600, respectively and can be made of similar suitable materials, as described, for example.

The expandable member 1506 can be placed into various arrangements, such as an unexpanded arrangement 1508a, as shown in FIG. 15A, or an expanded arrangement 1508b, as shown in FIG. 15B and be of various suitable shapes and sizes, such as a sphere, sphere like, teardrop like or ring like shape, for example. The expandable member 1506 can be made of similar suitable materials, such as an elastic medical grade material, a plastic material or a textile material, for example, that can be deflated, inflated/expanded and, when appropriate, disrupted, such as by being burst, that can allow for the expansion of the expandable member 1506, or can be made from other suitable material, such as depending upon the use or application, for example.

The expandable member 1506 can be placed into the unexpanded arrangement 1508a and expanded arrangement 1508b by having a therapeutic agent, such as therapeutic agent 124, placed within the expandable member 1506. The therapeutic agent, such as therapeutic agent 124, can be placed within the expandable member 1506 through the lumen 1504 of the catheter 1502. Further, the expandable member 1506 can be placed into at least one of a burst, leak or broken arrangement, depending on the use or application, for example, by being disrupted by a disrupting mechanism in which the therapeutic agent positioned within the expandable member can be deposited near an appropriate bodily part, such as a blood vessel puncture site, for example.

The expandable member 1506 can be disrupted by any of various embodiments of disrupting mechanisms, such as by the various disrupting mechanisms 118a-118e provided for and illustrated in FIGS. 2A-2E, as can depend on the particular needs or application. For example, the plurality of longitudinal breakage lines 118a, the generally circumferential breakage line 118b, the string disrupting mechanism 118c, the needle disrupting mechanism 118d, and the chemical disrupting mechanism 118e can all be used as a disrupting mechanism, for example, and should not be construed in a limiting sense.

The medical material delivery device 1500 further includes a bodily fluid locator 1510, as shown in FIGS. 15A and 15B. The bodily fluid locator 1510 is similar to the bodily fluid locator 523 of the medical material delivery device 500, and can allow for the user to be notified that the medical material delivery device 1500 is placed in a relative position with respect to a blood vessel or other bodily part. For example, if the medical material delivery device 1500 is placed near a blood vessel puncture site, bodily fluid such as blood can flow into the bodily fluid locator and can notify the user that the medical material delivery device 1500 is at an appropriate location relative to the blood vessel. The catheter 1502 and the bodily fluid locator 1510 can be placed in conjunction with one another and secured together through various mechanisms, such as a bracket 1512, as shown in FIGS. 15A and 15B.

Figure 16A:
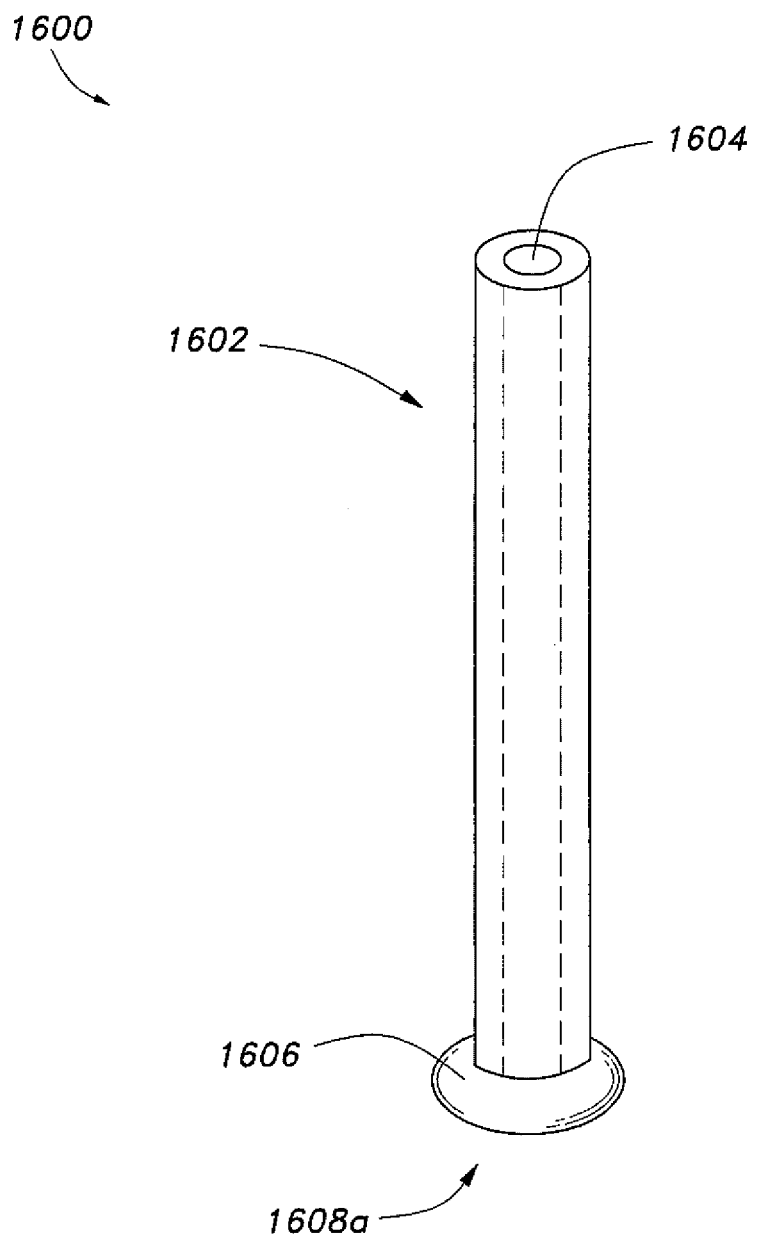
FIG. 16A is a perspective view of an embodiment of a medical material delivery device having a catheter with an expandable member according to the present invention.
Figure 16B:
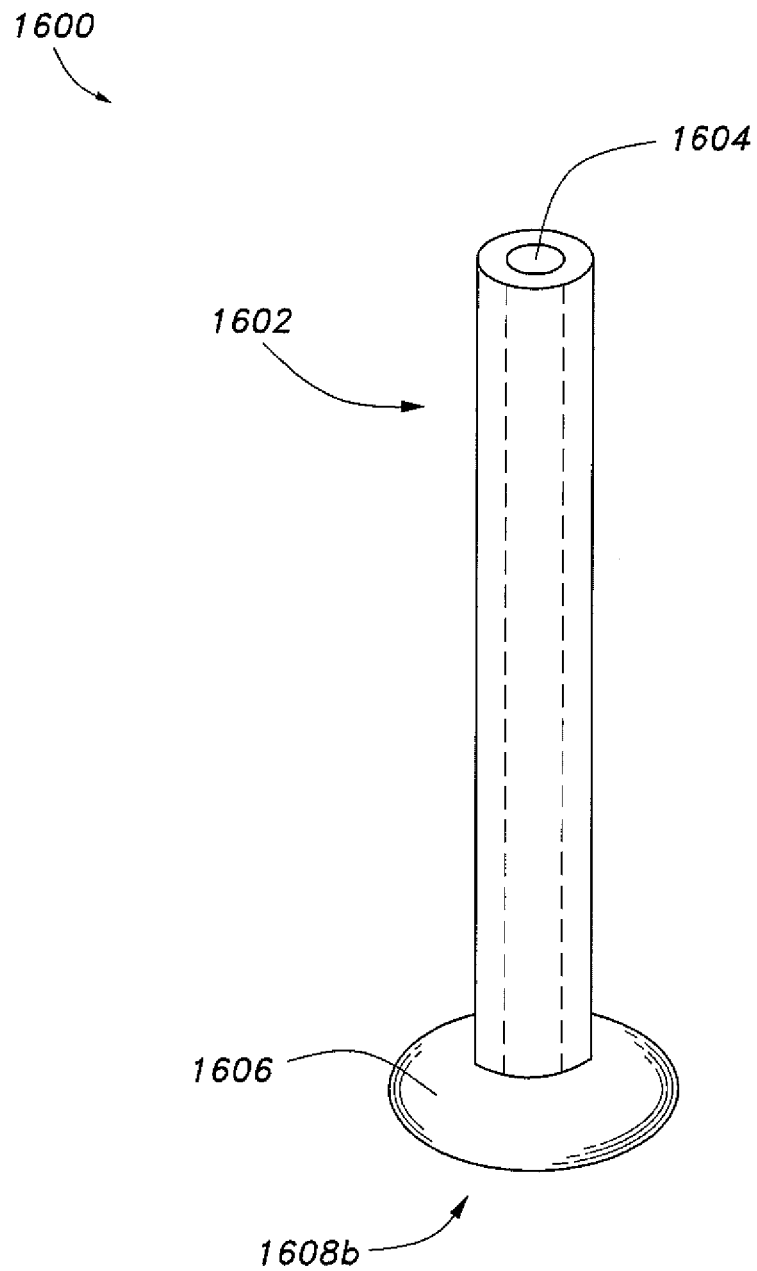
FIG. 16B is a perspective view of an embodiment of a medical material delivery device having a catheter with an inflated expandable member according to the present invention.

Referring to FIGS. 16A and 16B, a medical material delivery device 1600 is shown. The medical material delivery device 1600 includes a catheter 1602 having a lumen 1604. Positioned in conjunction with the catheter 1602 is an expandable member 1606, as shown in FIGS. 16A and 16B. The expandable member 1606 is similar to expandable members 114, 314, 414, 514, 608, 618, and 1506 and can be of various suitable shapes and sizes, such as a sphere, sphere like, teardrop like or ring like shape, for example.

Also the expandable member 1606 can be made of similar suitable materials, such as an elastic medical grade material, a plastic material or a textile material, for example, that can be deflated, inflated/expanded and, when appropriate, disrupted, such as by being burst, that can allow for the expansion of the expandable member 1606, or can be made from other suitable material, such as depending upon the use or application, for example. The expandable member 1606 can be placed into various arrangements, such as an unexpanded arrangement 1608a, as shown in FIG. 16A, and an expanded arrangement 1608b, as shown in FIG. 16B.

The expandable member 1606 can be placed into the unexpanded arrangement 1608a and the expanded arrangement 1608b by having a therapeutic agent, such as therapeutic agent 124, placed within the expandable member 1606. The therapeutic agent, such as therapeutic agent 124, can be placed within the expandable member 1606 through the lumen 1604 of the catheter 1602. Further, the expandable member 1606 can be placed into at least one of a burst, leak or broken arrangement, depending on the use or application, for example, by being disrupted by a disrupting mechanism in which the therapeutic agent positioned within the expandable member can be deposited near an appropriate bodily part, such as a blood vessel puncture site, for example.

The expandable member 1606 can be disrupted by any of various embodiments of disrupting mechanisms, such as by the various disrupting mechanisms 118a-118e provided for and illustrated in FIGS. 2A-2E, as can depend on the particular needs or application. For example, the plurality of longitudinal breakage lines 118a, the generally circumferential breakage line 118b, the string disrupting mechanism 118c, the needle disrupting mechanism 118d, and the chemical disrupting mechanism 118e can all be used as a disrupting mechanism, for example, and should not be construed in a limiting sense.

It is to be understood that the present invention is not limited to the embodiments described above, but encompasses any and all embodiments within the scope of the following claims.

I claim:
1. A medical material delivery device, comprising:
a shaft, the shaft having a proximal end and a distal end, the shaft having a lumen adapted for receiving a therapeutic agent;
a guide, the guide positioned at the distal end of the shaft and adapted for positioning in conjunction with a blood vessel or other bodily part, the guide having a channel configured to receive a medical instrument; and
an expandable member, the expandable member having an inner surface and an outer surface, the expandable member positioned in conjunction with the guide and in communication with the lumen of the shaft for expansion by the therapeutic agent when delivered through the lumen of the shaft, the expandable member adapted for communication with the blood vessel or other bodily part, the expandable member including a disrupting mechanism included in the outer surface of the expandable member thereby forming a weakened area thereat, whereby the expandable member can burst open to deliver the therapeutic agent to an area of the blood vessel or other bodily part in communication with the expandable member, wherein the disrupting mechanism includes at least one breakage line included in the outer surface of the expandable member, wherein the disrupting mechanism further includes a chemical solvent to react with the at least one breakage line included in the outer surface of the expandable member.

2. The medical material delivery device according to claim 1, wherein the guide and the expandable member are configured in a generally ring shape.

3. The medical material delivery device according to claim 1, wherein the guide and the expandable member are configured in a generally split ring shape.

4. The medical material delivery device according to claim 3, wherein the guide is comprised of memory shape material for adaptation around the medical instrument when the medical instrument is positioned within the generally split ring shape guide.

5. The medical material delivery device according to claim 1, wherein the guide is a sheath configured to wrap onto the medical instrument.

6. The medical material delivery device according to claim 1, wherein the shaft and the guide are integrally configured in a sheath to wrap onto the medical instrument.

7. A medical material delivery device, comprising:
a shaft, the shaft having a proximal end and a distal end, the shaft having a lumen adapted for receiving a therapeutic agent;
a guide, the guide positioned at the distal end of the shaft and adapted for positioning in conjunction with a blood vessel or other bodily part, the guide having a channel configured to receive a medical instrument; and
an expandable member, the expandable member having an inner surface and an outer surface, the expandable member positioned in conjunction with the guide and in communication with the lumen of the shaft for expansion by the therapeutic agent when delivered through the lumen of the shaft, the expandable member adapted for communication with the blood vessel or other bodily part, the expandable member including a disrupting mechanism arranged about the outer surface of the expandable member thereby forming a weakened area thereat for causing the expandable member to burst open to deliver the therapeutic agent to an area of the blood vessel or other bodily part in communication with the expandable member, wherein the disrupting mechanism includes at least one breakage line included in the outer surface of the expandable member, and wherein the disrupting mechanism further includes a chemical to erode the at least one breakage line included in the outer surface of the expandable member.

\* \* \* \* \*